(12) United States Patent
Sauer

(10) Patent No.: US 11,957,381 B2
(45) Date of Patent: Apr. 16, 2024

(54) MINIMALLY INVASIVE SPECIMEN RETRIEVAL SYSTEM AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 180 days.

(21) Appl. No.: 17/529,422

(22) Filed: Nov. 18, 2021

(65) Prior Publication Data

US 2022/0071661 A1    Mar. 10, 2022

Related U.S. Application Data

(63) Continuation of application No. 16/567,347, filed on Sep. 11, 2019, now Pat. No. 11,207,102.

(60) Provisional application No. 62/792,695, filed on Jan. 15, 2019, provisional application No. 62/730,429, filed on Sep. 12, 2018.

(51) Int. Cl.
*A61B 17/42* (2006.01)
*A61B 17/3207* (2006.01)

(52) U.S. Cl.
CPC ...... *A61B 17/42* (2013.01); *A61B 17/320758* (2013.01); *A61B 2017/4216* (2013.01)

(58) Field of Classification Search
CPC . A61B 17/29; A61B 17/2909; A61B 17/4241; A61B 17/32; A61B 17/32002; A61B 17/32075; A61B 17/320725; A61B 17/320758; A61B 2017/320024; A61B 2017/320775; A61B 2017/4216
See application file for complete search history.

(56) References Cited

U.S. PATENT DOCUMENTS

| | | | |
|---|---|---|---|
| 5,997,565 A | 12/1999 | Inoue | |
| 6,039,748 A * | 3/2000 | Savage | A61B 17/32002 606/107 |
| 8,082,925 B2 | 12/2011 | McCartney | |
| 8,192,444 B2 | 6/2012 | Dycus | |
| 8,603,105 B2 | 12/2013 | Sauer | |
| 9,649,130 B2 | 5/2017 | Parys | |
| 9,743,956 B2 | 8/2017 | Parys et al. | |

(Continued)

FOREIGN PATENT DOCUMENTS

| | | |
|---|---|---|
| EP | 1945111 | 3/2010 |
| WO | 2010137973 | 12/2010 |

(Continued)

*Primary Examiner* — Tuan V Nguyen
(74) *Attorney, Agent, or Firm* — Michael E. Coyne

(57) ABSTRACT

A specimen retrieval system is disclosed. The specimen retrieval system includes a first hollow tube including one or more cutting elements on a first end of the first hollow tube, a first gear on a second end of the first hollow tube, a second hollow tube movable relative to the first hollow tube a second gear on a first end of the second hollow tube, a rack coupled to the first gear and the second gear, and a first actuator coupled to the rack. A second end of the second hollow tube may include cutting elements. The specimen retrieval system also includes a rack coupled to the first gear on the first hollow tube and the second gear on the second hollow tube. The specimen retrieval system may also include a geared tenaculum disposed inside the first hollow tube, and a second actuator coupled to the geared tenaculum.

22 Claims, 42 Drawing Sheets

(56) References Cited

U.S. PATENT DOCUMENTS

| | | |
|---|---|---|
| 9,775,644 B2 | 10/2017 | Hess |
| 2008/0039883 A1 | 2/2008 | Nohilly |
| 2008/0255597 A1* | 10/2008 | Pravong ........... A61B 17/32002 606/171 |
| 2010/0204722 A1 | 8/2010 | Gilsdorf |
| 2014/0052018 A1 | 2/2014 | Hawkins |
| 2015/0018837 A1* | 1/2015 | Sartor ................ A61B 17/3205 606/114 |
| 2016/0100857 A1 | 4/2016 | Wachli et al. |

FOREIGN PATENT DOCUMENTS

| | | |
|---|---|---|
| WO | 2011140604 | 11/2011 |
| WO | 2016079752 | 5/2016 |
| WO | 2017189442 | 11/2017 |

* cited by examiner

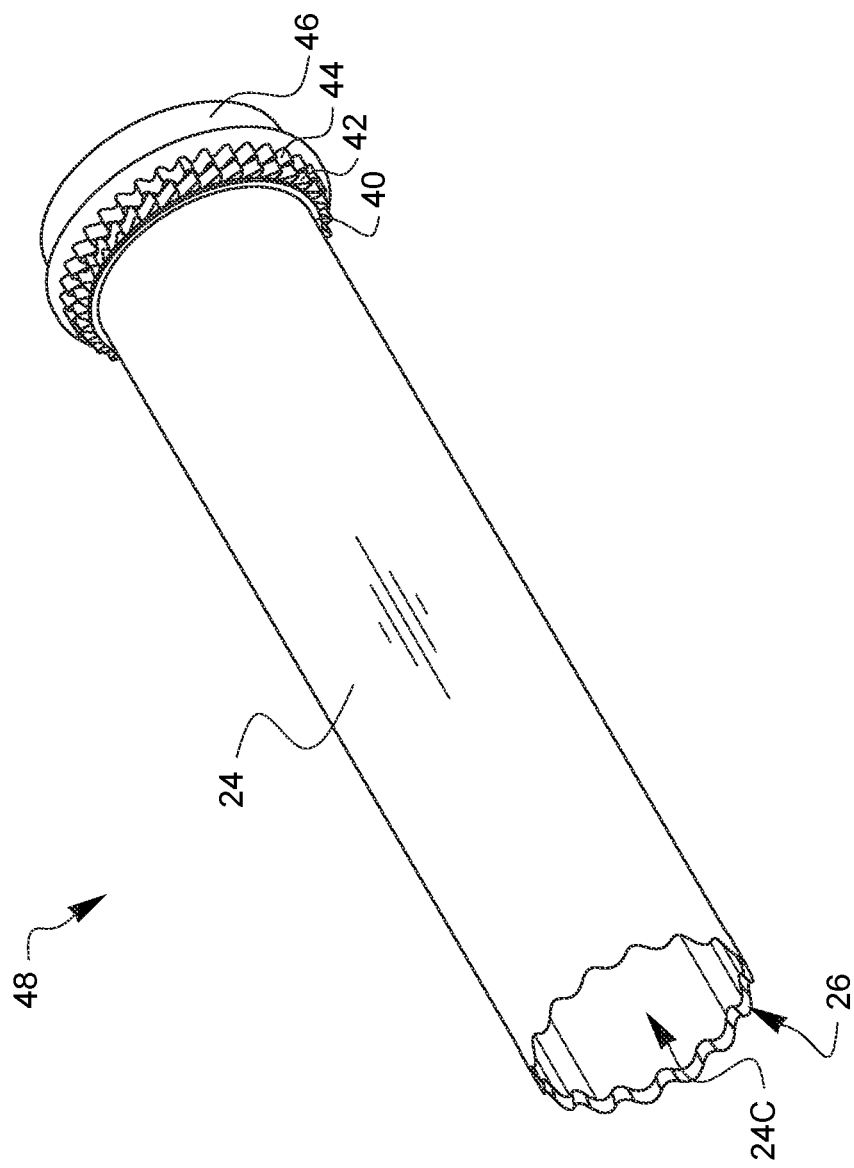

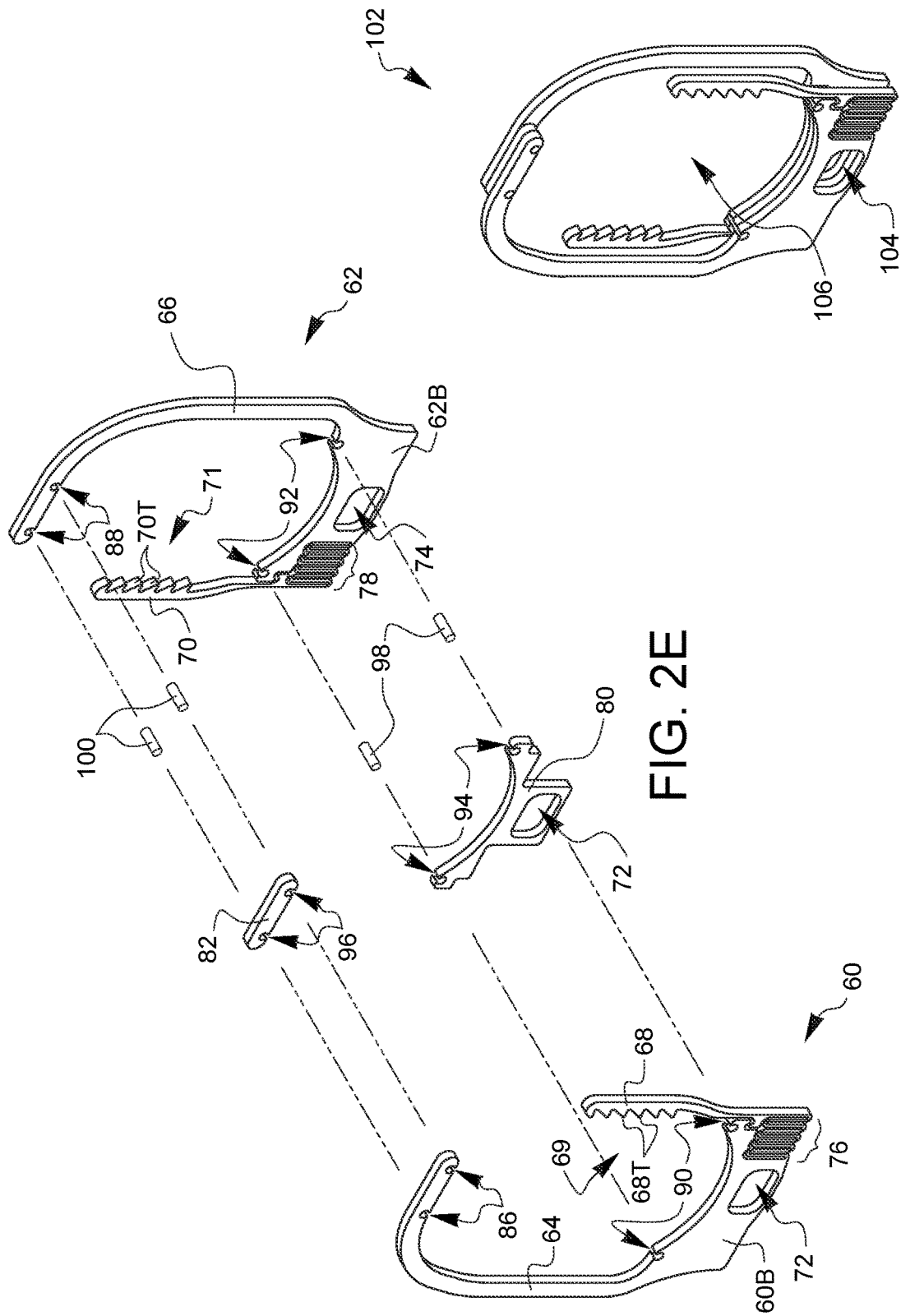

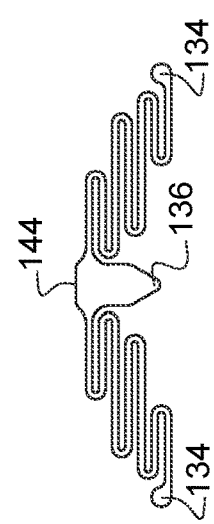
FIG. 4D
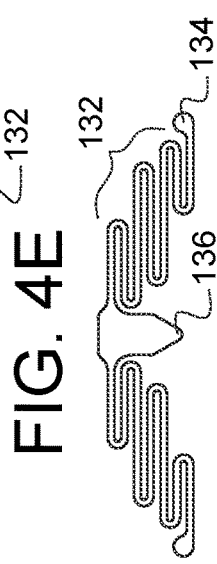
FIG. 4C
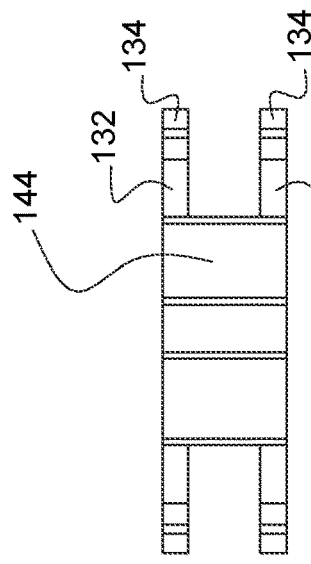
FIG. 4E
FIG. 4A
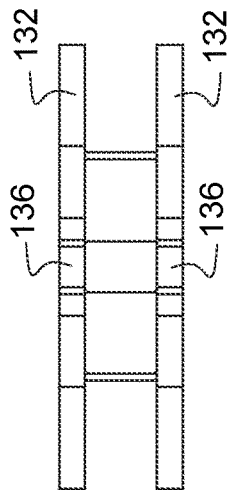
FIG. 4F
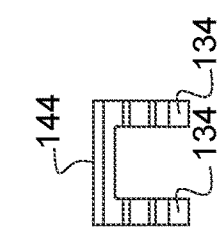
FIG. 4B

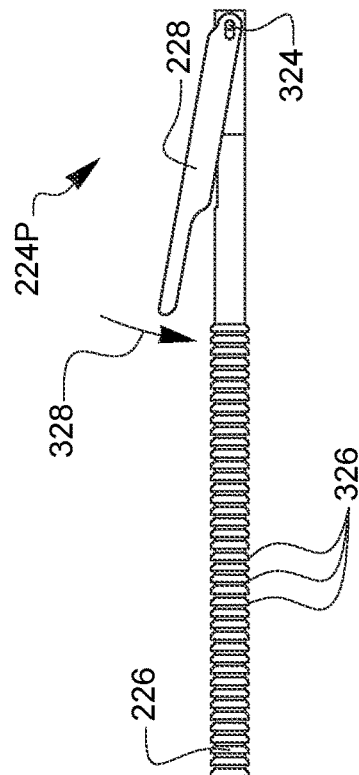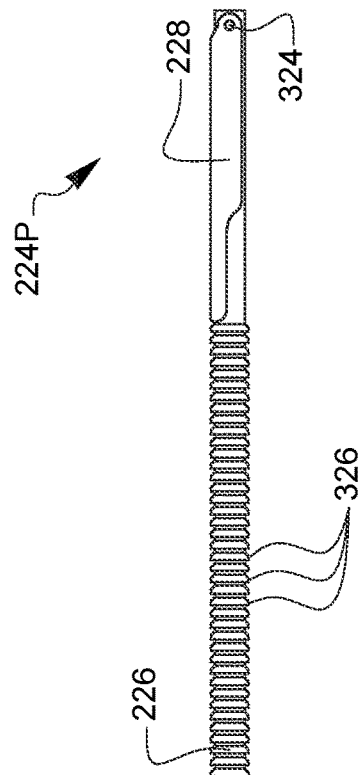
FIG. 10A
FIG. 10B

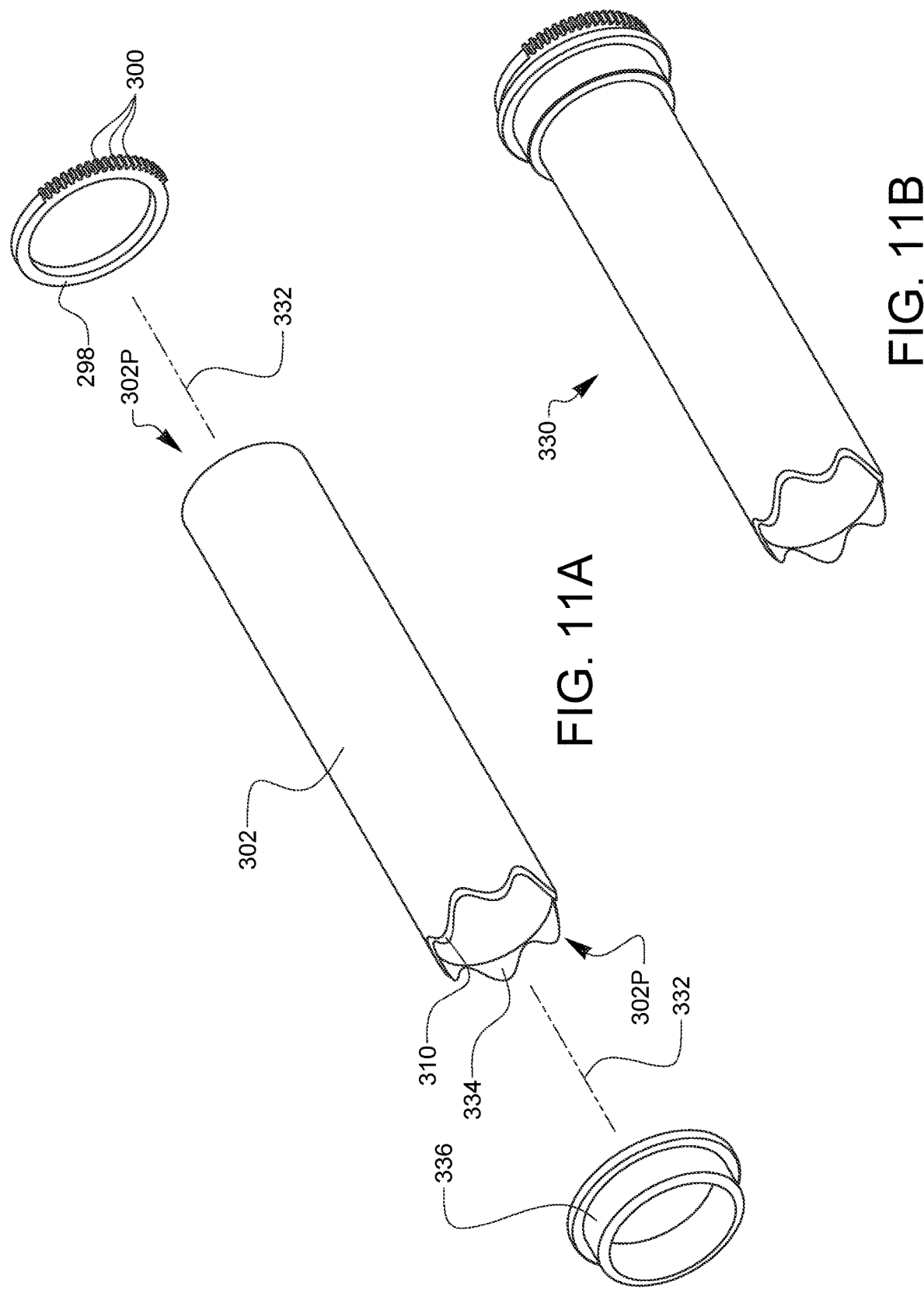

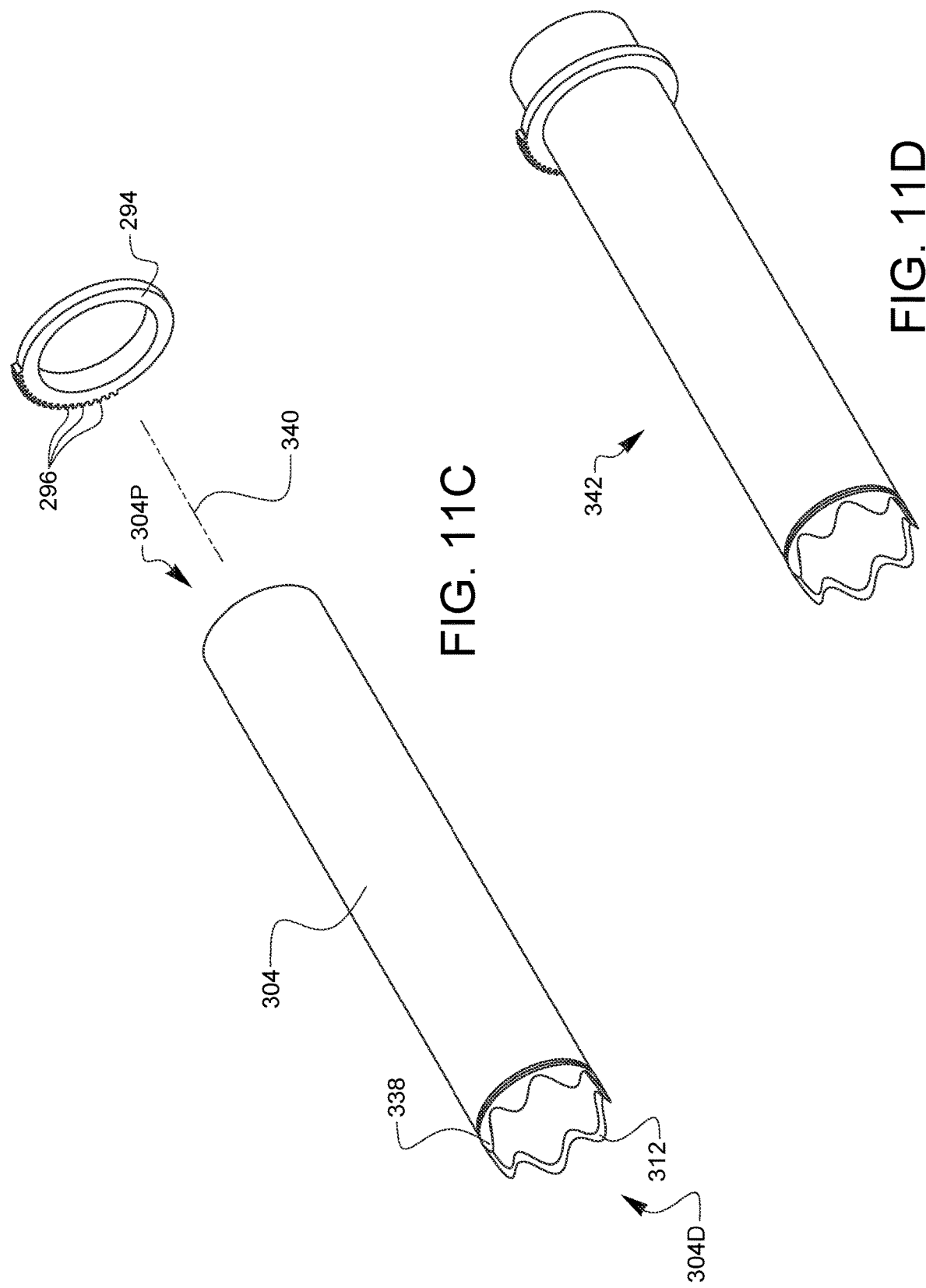

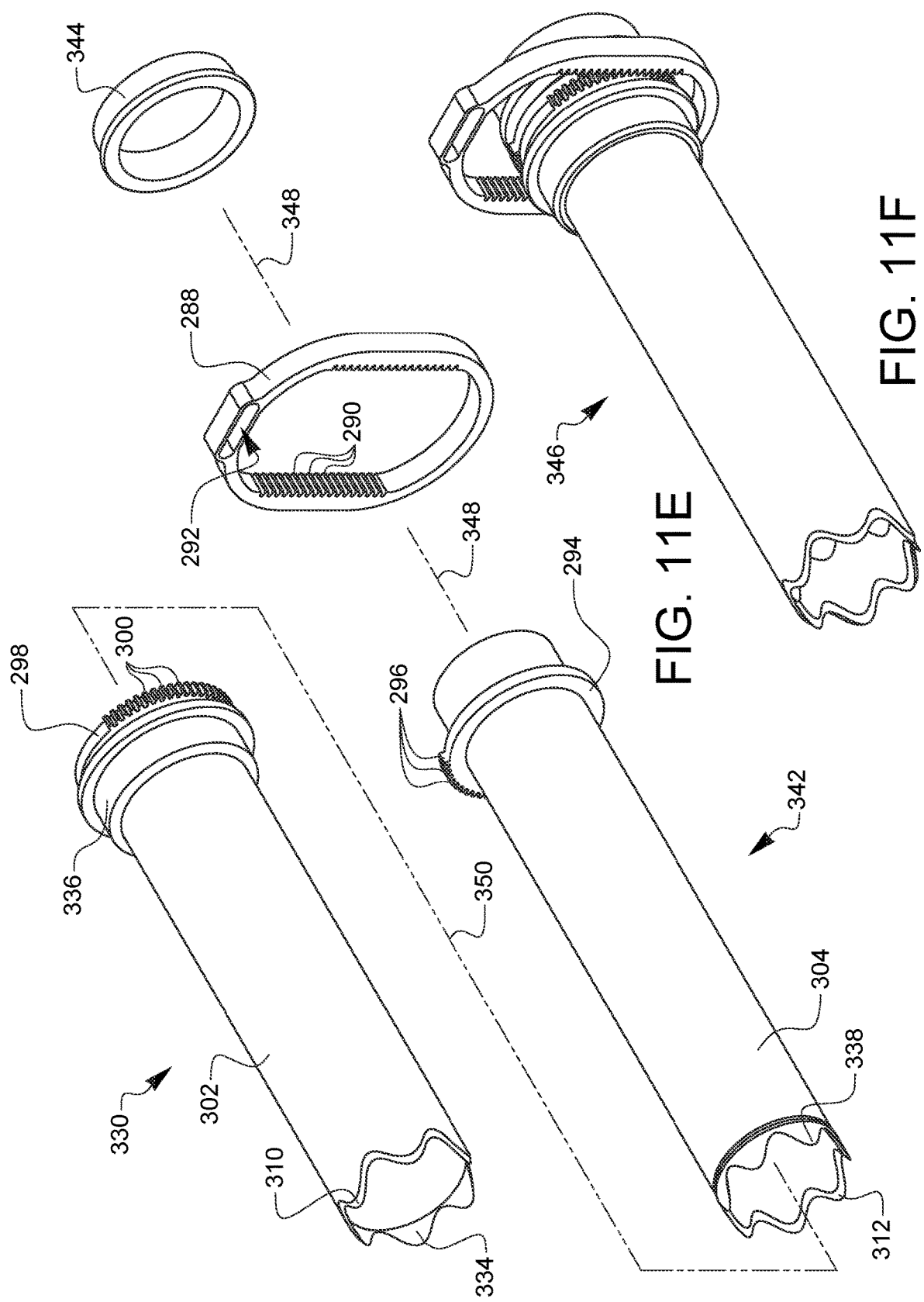

MINIMALLY INVASIVE SPECIMEN RETRIEVAL SYSTEM AND METHODS THEREOF

REFERENCE TO RELATED APPLICATIONS

This application claims priority to, and is a continuation of, U.S. patent application Ser. No. 16/567,347, filed Sep. 11, 2019 and titled "MINIMALLY INVASIVE SPECIMEN RETRIEVAL SYSTEM AND METHODS THEREOF," which claims priority to U.S. Provisional Patent Application No. 62/730,429, filed Sep. 12, 2018 and titled "MINIMALLY INVASIVE UTERINE CORING DEVICE AND METHODS THEREOF," and U.S. Provisional Patent Application No. U.S. 62/792,695, filed Jan. 15, 2019 and titled "MINIMALLY INVASIVE UTERINE CORING DEVICE AND METHODS THEREOF," the contents of each of which is hereby incorporated by reference in its entirety.

FIELD

The claimed invention relates to minimally invasive surgical devices, and more specifically to minimally invasive uterine coring devices and methods.

BACKGROUND

Vaginal hysterectomy has been an accepted surgical procedure in gynecology for many years; however, its application has declined since the rise of abdominal laparoscopic hysterectomy. Advancements in laparoscopic hysterectomy have resulted in increased adoption of laparoscopic and robotic surgery for complex gynecological procedures. There have also been promising advances in gynecological minimally invasive surgery techniques such as natural orifice transluminal surgery (NOTES), Laparoendoscopic Single Site (LESS), and others, which have attracted attention as less invasive alternatives to laparoscopy.

NOTES represents an advancement of minimally invasive intra-abdominal procedures, whereby access to the peritoneal cavity is achieved by incising and traversing the lumen of a natural orifice. This approach reduces the need for abdominal wall incisions and results in reduced scarring and therefore an improved cosmetic outcome. While several natural orifices are potential access routes to the peritoneal cavity, such as oral, anal, vaginal, or urethral orifices, the vagina is the most commonly used NOTES portal of entry. The vaginal route of surgery and specimen removal may be applicable for the uterus and other intra-abdominal organs with minimal added morbidity. This can be attributed to its ease of access and capaciousness, as well as its relationship to the target anatomy. Additional benefits of accessing via the natural orifices include shorter operative times, decreased blood loss, reduced postoperative stay, and improved patient recovery.

A limiting factor in these less invasive procedures is often the removal of an intact uterus or an unruptured adnexal mass. Additional challenges include large tumor size, unexpected malignancy or pathology, specimen removal, and intraoperative spillage of tumor contents during surgery. The risk of spillage of the cyst contents is associated with complications such as pseudomyxoma peritonei (mucinous cystadenoma), chemical peritonitis (dermoid cyst) and the potential dissemination of malignancy. These disadvantages may be partially addressed with the use of morcellation, or the division of solid tissue into smaller pieces, or the use of endoscopic bag pouches, or combinations thereof.

While intraabdominal morcellation can be utilized to reduce the size of the tissue such as large uterine fibroids or a uterus as part of total laparoscopic hysterectomy (TLH), it brings risk of intraabdominal tumor spread if the specimen contains a malignancy or peritoneal metastases. Further, morcellation of a specimen through the vaginal incision is often difficult, time consuming, and can result into trauma to nearby structures. Endoscopic bag pouches can be introduced and removed, for example, through a 10 mm port site, or through the vaginal opening. Leakage or spillage of the contents of the bag pouch into the peritoneal cavity may lead to chemical peritonitis or malignant cell spread.

Therefore, a need exists for a minimally invasive gynecological surgical device and methodology for improved specimen removal and patient safety during minimally invasive procedures preferentially utilizing a natural orifice as a portal of entry during gynecological and other surgical procedures.

SUMMARY

A specimen retrieval system is disclosed. The specimen retrieval system includes a first hollow tube including one or more cutting elements on a first end of the first hollow tube, a first gear on a second end of the first hollow tube, a second hollow tube movable relative to the first hollow tube a second gear on a first end of the second hollow tube, a rack coupled to the first gear and the second gear, and a first actuator coupled to the rack.

Another specimen retrieval system is disclosed. The specimen retrieval system includes a first hollow tube including one or more cutting elements on a first end of the first hollow tube, and a first gear on a second end of the first hollow tube; a second hollow tube movably coupled to the first hollow tube including one or more cutting elements on a first end of the second hollow tube, and a second gear on a second end of the second hollow tube. The specimen retrieval system also includes a rack coupled to the first gear on the first hollow tube and the second gear on the second hollow tube. The specimen retrieval system also includes a first actuator coupled to the rack, a geared tenaculum disposed inside the first hollow tube, a second actuator coupled to the geared tenaculum. The first hollow tube and the second hollow tube of the specimen retrieval system are coaxial, and the first hollow tube is inside the second hollow tube.

BRIEF DESCRIPTION OF THE DRAWINGS

FIGS. 2A-2H and 2J-2K are a series of exploded views of the assembly of the minimally invasive uterine coring device of FIG. 1.

FIGS. 4A, 4B, 4C, 4D, 4E, and 4F are front, left side, right side, rear, top, and bottom elevational views, respectively, of the synchronizing lock of FIG. 3.

FIGS. 10A and 10B are side-views of the specimen retrieval tenaculum of FIG. 7C in an open and closed position, respectively.

FIG. 11A-11H, and 11J-11L are a series of exploded views of the assembly of the surgical specimen retrieval system of FIG. 7A.

Figure 1:
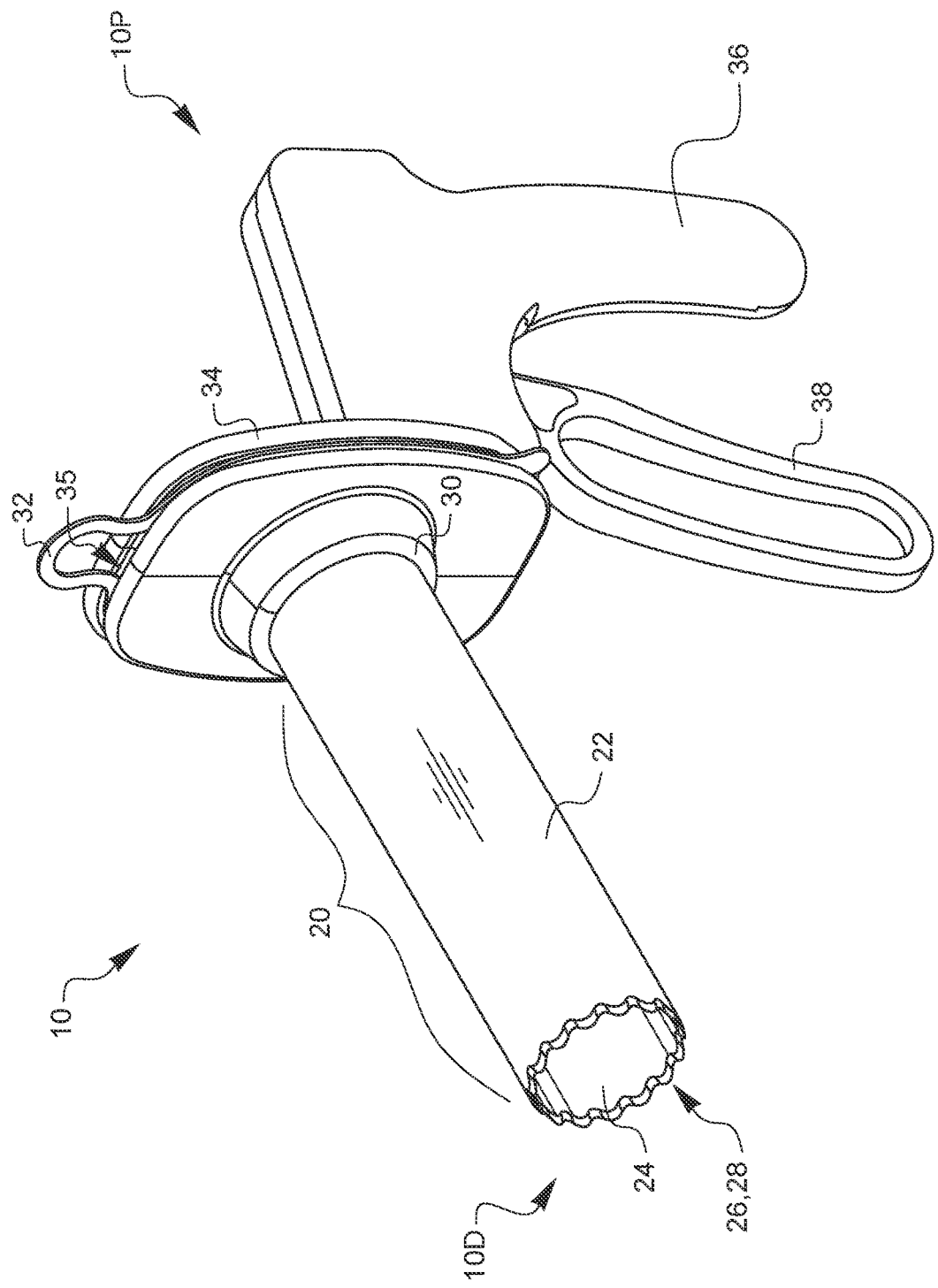
FIG. 1 is a top-left-front perspective view of a minimally invasive uterine coring device.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1 is a top-left-front perspective view of a minimally invasive uterine coring device. The uterine coring device 10, which may also be referred to as a surgical coring device as it may be used in other surgical procedures, has a housing 34 including a handle 36, an actuator lever 38, and a tube guide 30. In communication with the tube guide 30 is a blade assembly 20 including a hollow inner tube 24 and a hollow outer tube 22, each having sharpened ends 26, 28. The housing 34 is also configured to releasably hold a retention clip or retaining clip 32 within a housing recess 35 for the purpose of retaining a specimen encapsulation bag, which is not shown here but discussed later. The inner tube 24 cutting element and the outer tube 22 cutting element are both hollow and the completed uterine coring device 10 is hollow throughout the blade assembly 20 in communication with the proximal end 10P of the uterine coring device 10. It should be noted that the uterine coring device herein may also be referred to as a specimen retrieval system, as the purpose of the uterine coring device and major portions of its components are consistent with the specimen retrieval systems described herein.

Figure 2A:
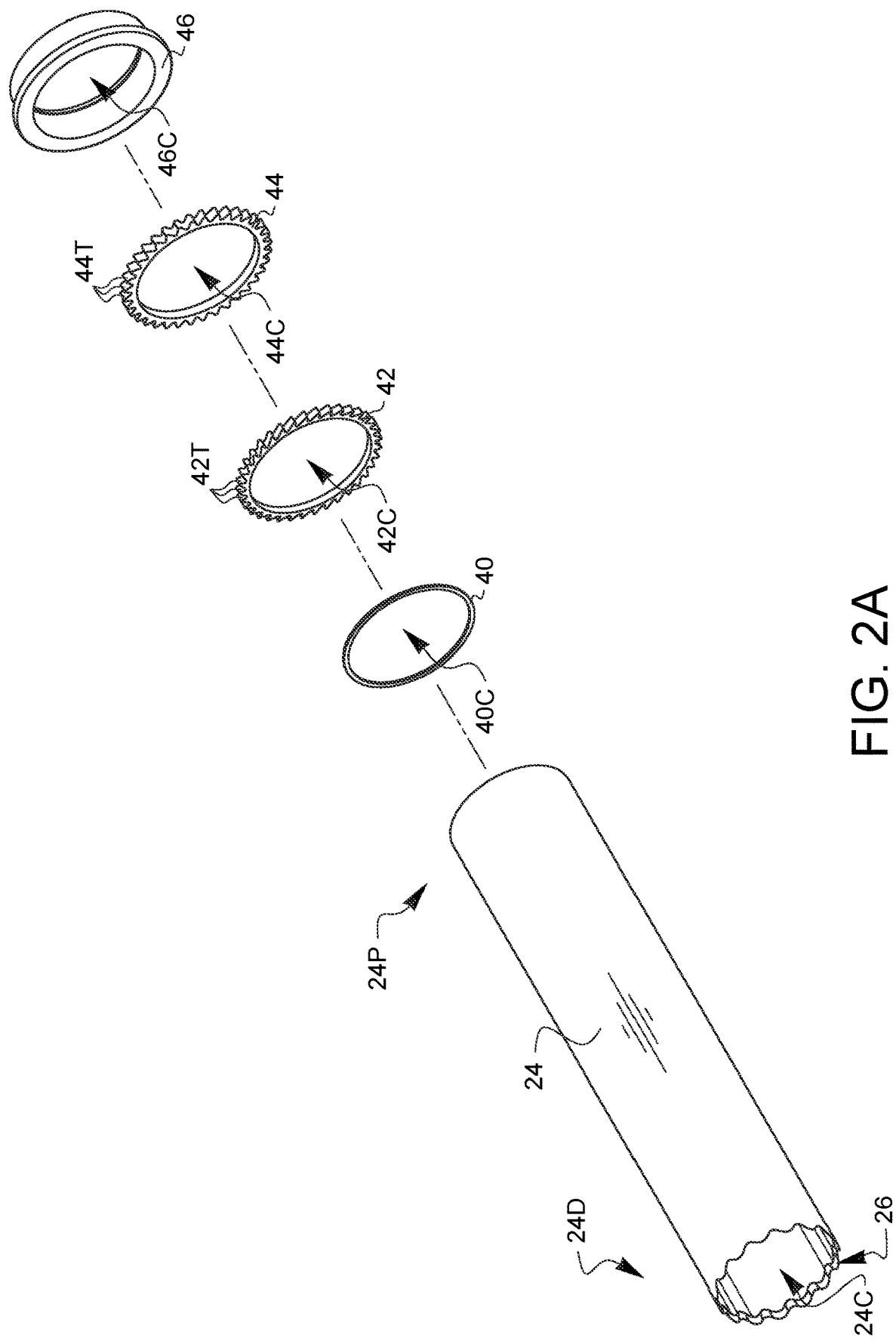

FIGS. 2A-2H and 2J-2K are a series of exploded views of the assembly of the minimally invasive uterine coring device of FIG. 1. FIG. 2A is an exploded view of an inner tube subassembly of the minimally invasive uterine coring device of FIG. 1. The inner tube 24 is a hollow cylindrical tube with a sharpened end 26 at a distal end 24D of the inner tube 24. The inner tube 24 has a hollow center 24C and is configured to receive several components on its outer surface. An inner tube spacer 40, inner tube asymmetrical gear 42, inner tube symmetrical gear 44, and an inner tube bushing 46 are assembled along a longitudinal axis 25 onto the proximal end 24P of the inner tube 24 and fixedly attached to the outer surface of the inner tube 24. The inner tube 24 is inserted into the respective centers 40C, 42C, 44C, and 46C of the inner tube spacer 40, inner tube asymmetrical gear 42, inner tube symmetrical gear 44, and inner tube bushing 46. The inner tube asymmetrical gear 42 has several asymmetrical teeth 42T around its outer circumference, and the inner tube symmetrical gear 44 has several symmetrical teeth 44T around its outer circumference. The inner tube 24 is made from stainless steel, and could alternatively be composed of any suitable metal or resilient plastic composite or other material suitable for surgical devices. The inner tube 24 may also have one or more scallops or teeth or other cutting elements at the end of the inner tube 24. The inner tube spacer 40, inner tube asymmetrical gear 42, inner tube symmetrical gear 44, and inner tube bushing 46 are made from a resilient plastic composite and fixedly attached to the inner tube 24 using epoxy, but any alternate appropriate adhesive could be used. FIG. 2B is a perspective view of the assembled inner tube subassembly of the minimally invasive uterine coring device of FIG. 2A. The inner tube subassembly 48 is the result of the assembly steps illustrated in FIG. 2A. The resulting subassembly could alternatively be molded or fabricated as a single component using surgical stainless steel, a suitable plastic composite, or other material suitable for surgical devices.

Figure 2C:
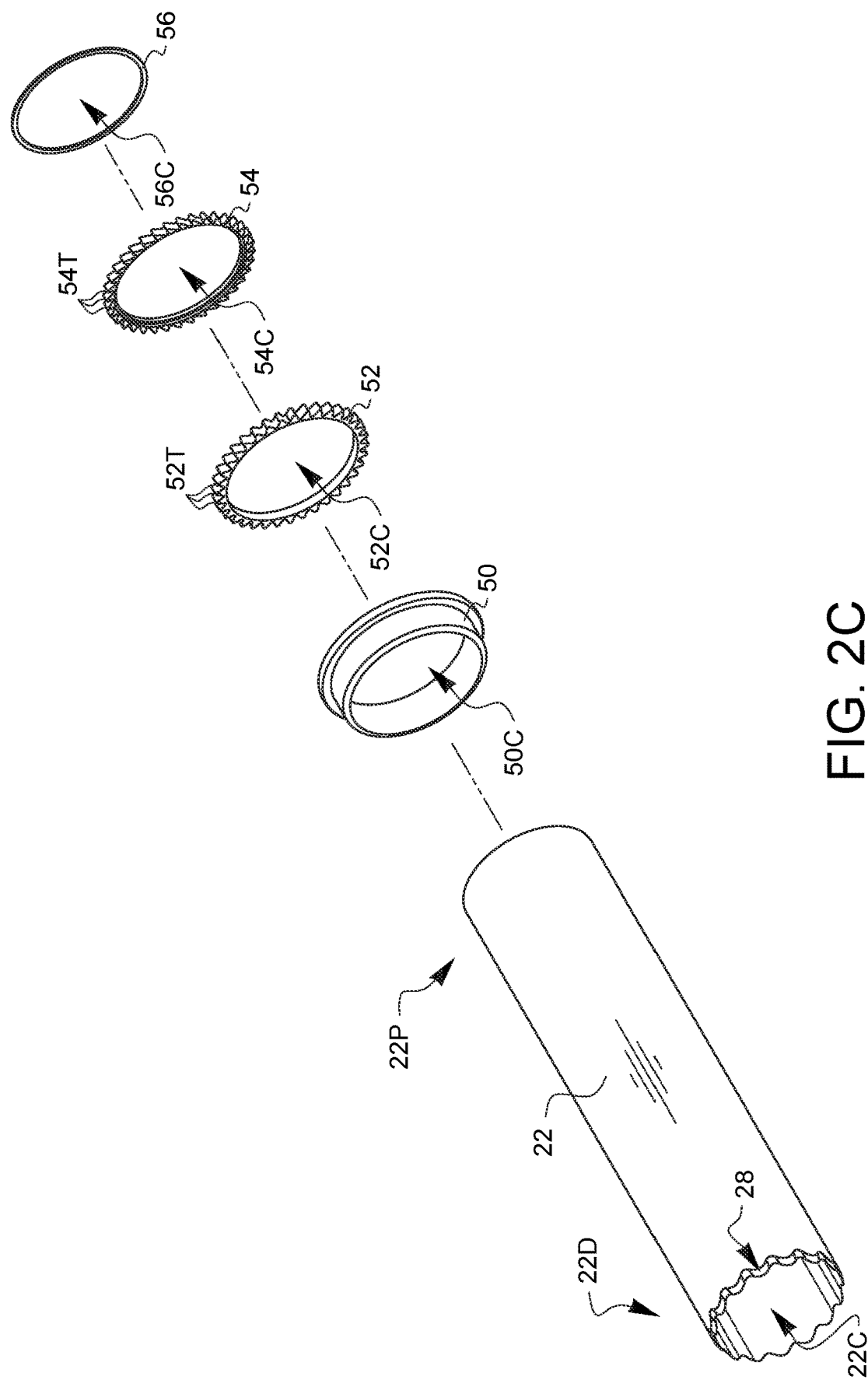
Figure 2D:
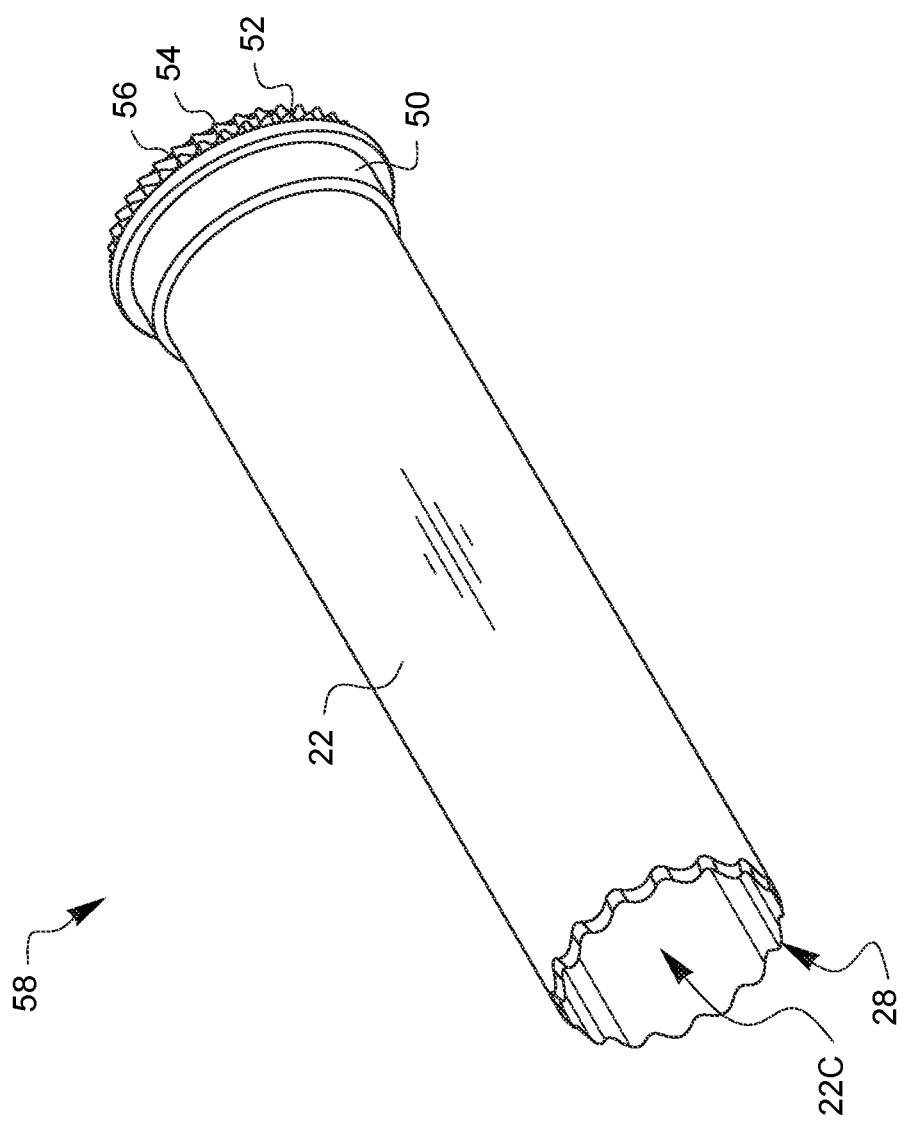

FIG. 2C is an exploded view of an outer tube subassembly of the minimally invasive uterine coring device of FIG. 1. The outer tube 22 is a hollow cylindrical tube with a sharpened end 28 at a distal end 22D of the outer tube 22. The outer tube 22 has a hollow center 22C and is configured to receive several components on its outer surface. An outer tube bushing 50, outer tube symmetrical gear 52, outer tube asymmetrical gear 54, and an outer tube spacer 56 are assembled along a longitudinal axis 27 onto the proximal end 22P of the outer tube 22 and fixedly attached to the outer surface of the outer tube 22. The outer tube 22 is inserted into the respective centers 50C, 52C, 54C, and 56C of outer tube bushing 50, outer tube symmetrical gear 52, outer tube asymmetrical gear 54, and an outer tube spacer 56. The outer tube symmetrical gear 52 has several symmetrical teeth 52T around its outer circumference and the outer tube asymmetrical gear 54 has several asymmetrical teeth 54T around its outer circumference. The outer tube 22 is made from stainless steel, and could alternatively be composed of any suitable metal or resilient plastic composite or other material suitable for surgical devices. The outer tube 22 may also have one or more scallops or teeth or other cutting elements at the end of the outer tube 22. The outer tube bushing 50, outer tube symmetrical gear 52, outer tube asymmetrical gear 54, and outer tube spacer 56 are made from a resilient plastic composite and fixedly attached to the outer tube 22 using epoxy, but any alternate appropriate adhesive could be used. FIG. 2D is a perspective view of the assembled outer tube subassembly of the minimally invasive uterine coring device of FIG. 2C. The outer tube subassembly 48 is the result of the assembly steps illustrated in FIG. 2C. The resulting subassembly could alternatively be molded or fabricated as a single component using surgical stainless steel, a suitable plastic composite, or other material suitable for surgical devices.

FIG. 2E is an exploded view of a flex rack subassembly of the minimally invasive uterine coring device of FIG. 1. A flex rack 60 consists of a base portion 60B which defines an opening 72. A support arm 64 and a spring element 76 are connected to the base portion 60B of the flex rack 60. The spring element further defines a flex rack arm 68. The flex rack arm 68 defines several teeth 68T on the inward side 69 of the flex rack arm 68. This flex rack arm 68 is configured to function as an asymmetric rack gear. There are two notches 90 on the base portion 60B of the flex rack 60, and two notches 86 on the support arm 64. An upper spacer 82 defines two notches 96, which are configured to align with notches 86 in flex rack arm 68. Two pins 100 are configured for insertion into notches 96 and 86 for fixedly attaching flex rack 60 and upper spacer 82 along longitudinal axis 61 and longitudinal axis 63. A lower spacer 80 defines an opening 84 configured to align with opening 72 in the flex rack 60. The spacer 80 further defines two notches 94 configured to align with notches 90 in the flex rack 60. Two pins 98 are configured for insertion into notches 94 and 90 for fixedly attaching flex rack 60 and lower spacer 80 along longitudinal axis 65 and longitudinal axis 67. A second flex rack 62 consists of a base portion 62B which defines an opening 74. A support arm 66 and a spring element 78 are connected to the base portion 62B of the flex rack 62. The spring element further defines a flex rack arm 70. The flex rack arm 70 defines several teeth 70T on the inward side 71 of the flex rack arm 70. This flex rack arm 70 is configured to function as an asymmetric rack gear. There are two notches 92 on the base portion 62B of the flex rack 62, and two notches 88 on the support arm 66. Notches 88 and notches 92 are aligned with pins 100 and pins 98, respectively to fixedly attach flex rack 62 along longitudinal axes 61, 63, 65, and therefore complete the flex rack subassembly 102 illustrated in FIG. 2F. FIG. 2F is a perspective view of the assembled flex rack subassembly of FIG. 2E. The flex rack subassembly 102 as assembled defines an opening 104 defined by the opening 72 in flex rack 60, the opening 84 in spacer 80, and the opening 74 in flex rack 62. Additionally, an opening 106 for the inner and outer tube assemblies (not shown in this view) is defined by the flex racks 60, 62. While flex rack 60 and flex rack 62 are identical parts and assembled opposite one another, a similar flex rack assembly could alternately be made using components or parts that are not identical to one another, but serve the same function or have the same construction as the flex rack arms 68, 70, spring elements 76, 78, and other elements shown in the flex rack subassembly 102. Alternatively, a flex rack subassembly could be fabricated as a single, monolithic piece or element.

Figure 2G:
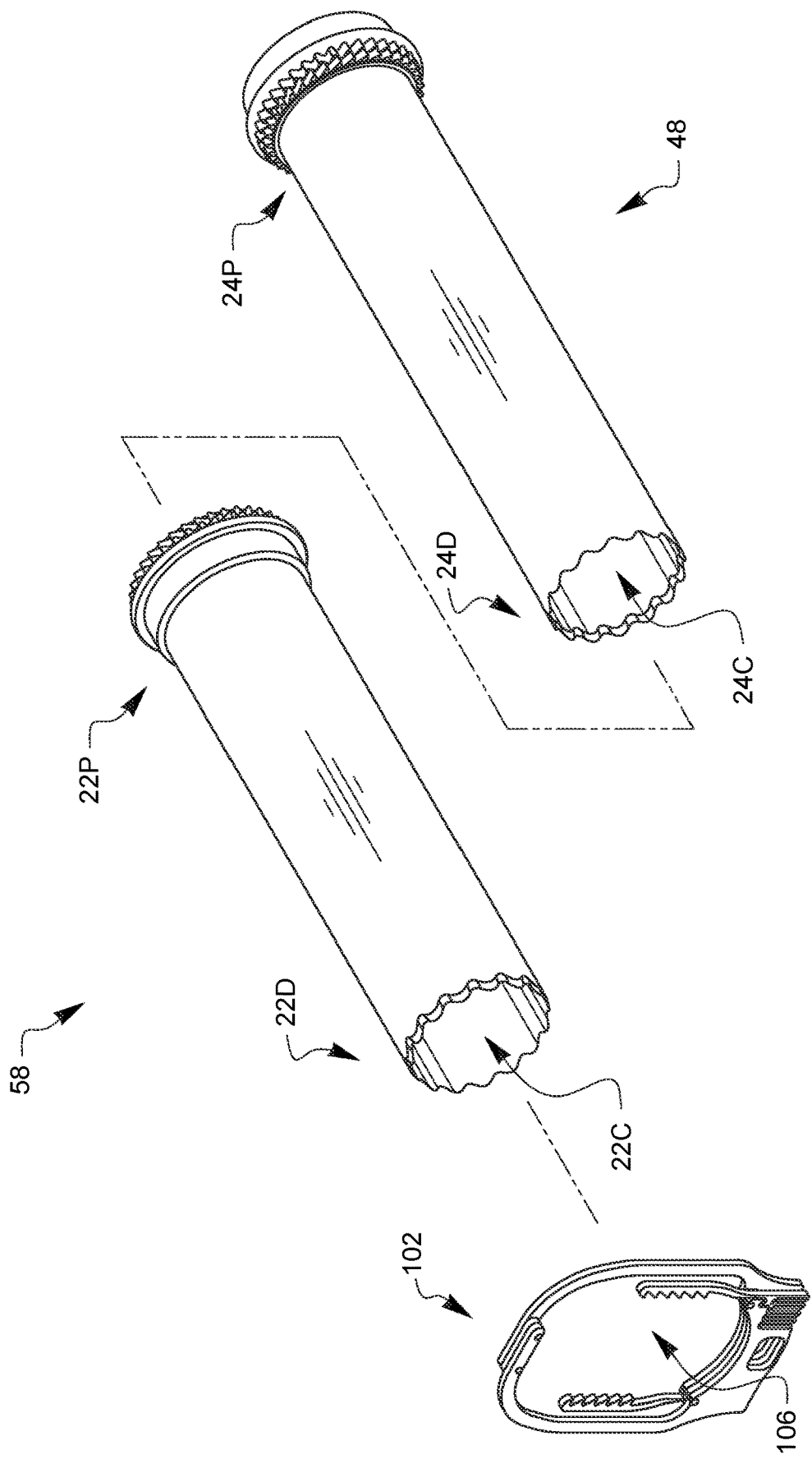

FIG. 2G is an exploded view of a flex rack and tube subassembly illustrating the assembly of the inner tube subassembly of FIG. 2B, outer tube subassembly of FIG. 2D, and the flex rack subassembly of FIG. 2F. Inner tube subassembly 48 is inserted into the center 22C of outer tube 22 starting at the proximal end 22P of the outer tube 22 in the outer tube subassembly 58 along longitudinal axis 108, then the two tube subassemblies 48, 58 are placed within opening 106 along longitudinal axis 108 in the flex rack subassembly 102. It should be noted that inner tube subassembly 48 and outer tube subassembly 58 are freely rotatable with respect to one another once assembled.

Figure 2H:
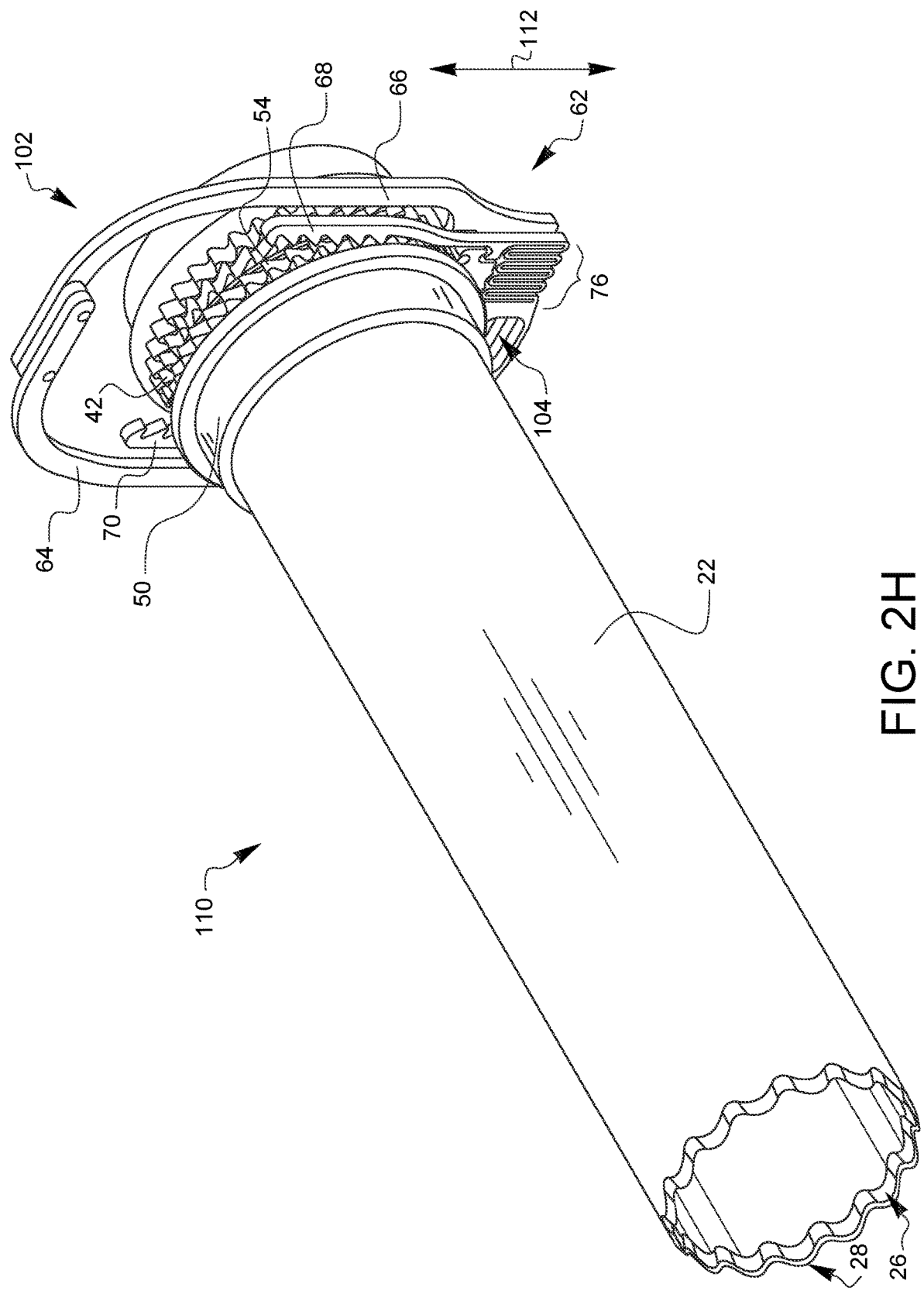

FIG. 2H is a perspective view of the flex rack and tube subassembly of FIG. 2G. The flex rack and tube subassembly 110 is shown assembled, with flex rack arm 70 aligned to inner tube asymmetrical gear 42 and flex rack arms 68 aligned to outer tube asymmetrical gear 54. The flex rack subassembly 102 is configured to move in either direction vertically 112 in order to counter-rotate the inner tube subassembly 48 relative to the outer tube subassembly 58. Thus, the movement of the flex rack subassembly 102 is configured to counter-rotate the two hollow tubes. This will be described in greater detail with regard to FIGS. 5A-5B and 10A-10B. Since inner tube sharpened end 26 is adjacent to the outer tube sharpened end 28, if the two hollow tubes 22, 24 are counter-rotated, the sharpened ends are configured to act as circular scissors and cut through soft tissue. While the subassembly shown in FIG. 2H has two sharpened ends 26, 28, it may be desirable for the outer tube 22 to have one or more shielding elements configured to coincide with a sharpened end or cutting elements on the inner tube 24. The purpose of such shielding elements would be to protect areas of the body or tissue within the body outside the scope of a given surgical procedure from trauma or cutting while a surgical device as described herein is introduced into a body or a body cavity, in particular when in use for a transvaginal removal or retrieval of various surgical specimens.

Figure 2J:
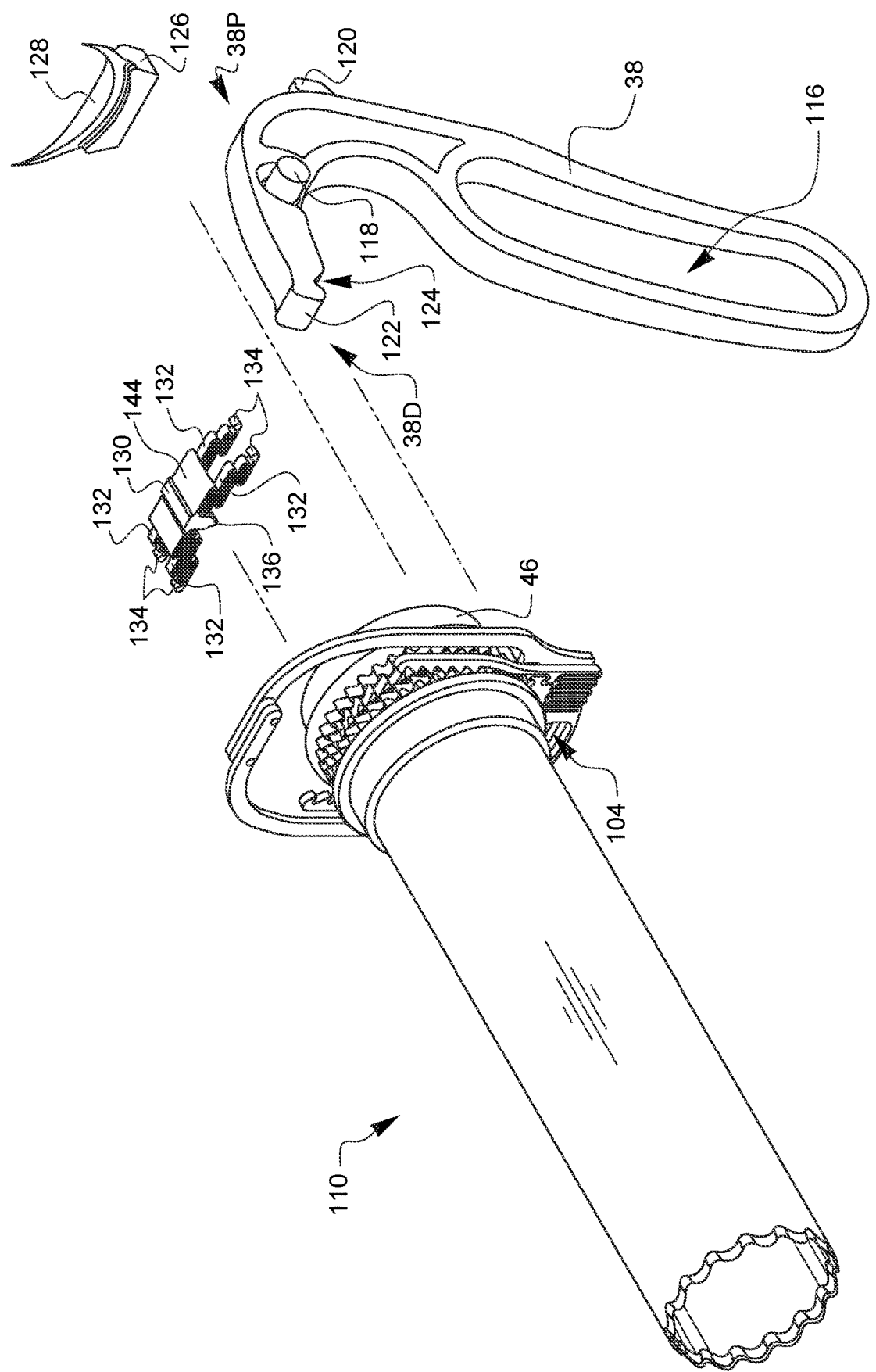
Figure 2K:
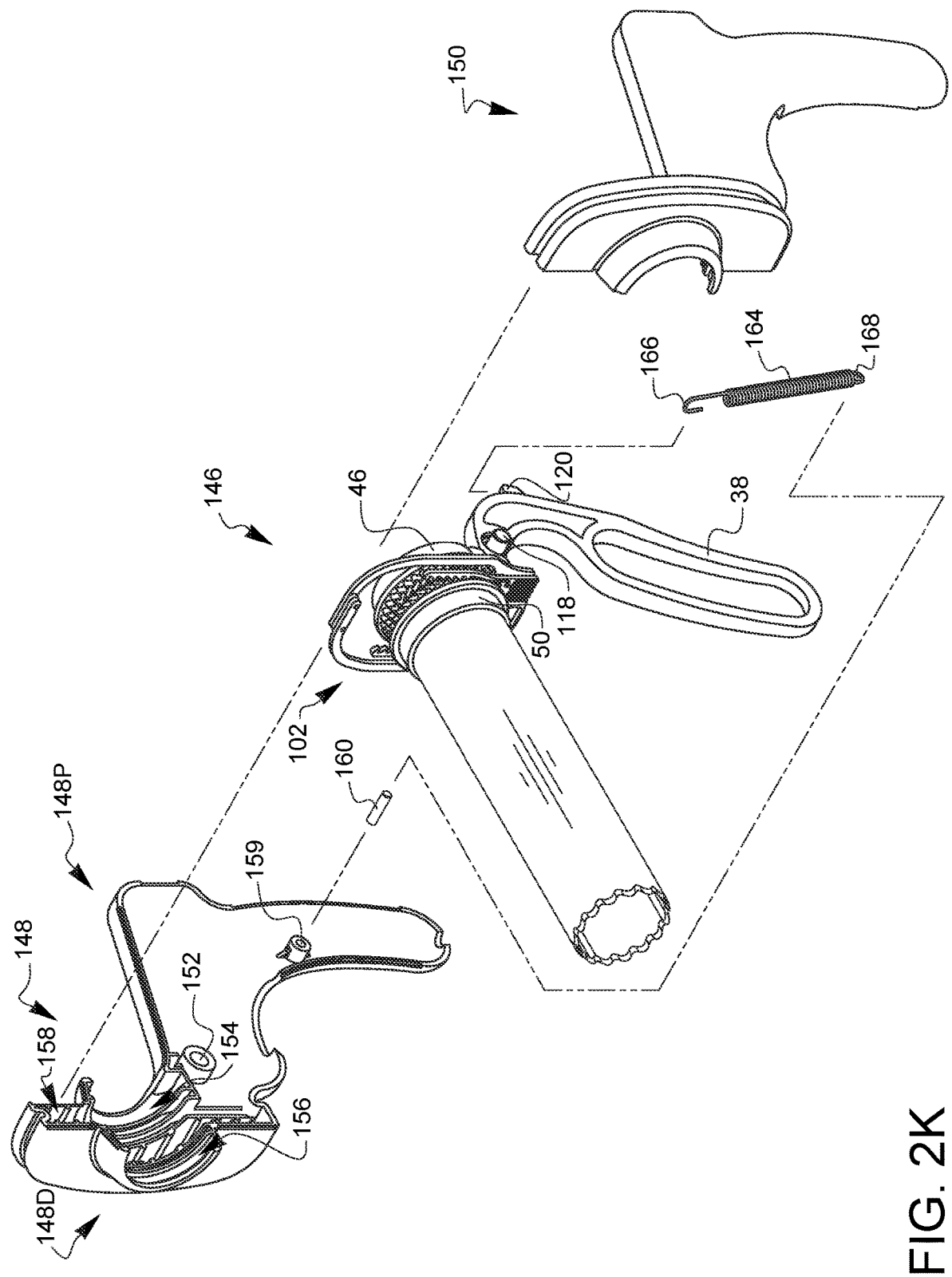

FIGS. 2J and 2K are exploded views of the minimally invasive uterine coring device of FIG. 1. FIG. 2J illustrates an additional step in the assembly of the uterine coring device 10 of FIG. 1. A synchronizing lock spring 130 having four spring elements 132 and a tooth 136 on either side in communication with its top surface 144 is moved along longitudinal axis 138 above the flex rack and tube subassembly 110 and into the opening 106 of the flex rack subassembly 102. This synchronizing lock may be an optional component, as will be described in regard to FIGS. 3 and 4A-4F, depending on the embodiment or particular configuration of the uterine coring device 10. A filler block 126 having a rounded tube recess 128, configured for stabilizing the inner tube bushing 46 within the housing is placed against the flex rack and tube subassembly 110 along longitudinal axis 140. The actuator lever 38 has a user recess 116 configured for grasping and squeezing with a hand during operation and a lever axle 118 for mounting the actuator lever 38 in a pivotable location in a housing. The actuator lever 38 also has a spring hook 120 on the proximal end 38P of the actuator lever 38 and an actuator 122 and actuator recess 124 at the distal end 38D of the actuator lever 38. The actuator lever 38 is added to the subassembly by inserting the actuator of the actuator lever 38 into the opening 104 of the flex rack and tube subassembly 110 along longitudinal axis 142. It should be noted that the assembly steps illustrated in FIG. 2J may not necessarily be complete and may need to be carefully held in place until subsequent assembly steps described in FIG. 2K are completed.

FIG. 2K is an exploded view of the minimally invasive uterine coring device of FIG. 1 during its final stages of assembly. FIG. 2K illustrates the resulting subassembly 146 from FIG. 2J prepared for final assembly. A spring 164 having a spring hook 166 and a spring hole 168 is placed along axis 172 such that the spring hook 166 is placed over the hook 120 on the actuator lever 38 in subassembly 146. First housing half 148 having a proximal side 148P and a distal side 148D defines several features for the final assembly of the minimally invasive uterine coring device 10 of FIG. 1, including a hole for the lever axle 152, a proximal housing recess 154, a distal housing recess 156, a central housing recess 158, and a mounting hole 159 for a pin 160. To complete the assembly of the minimally invasive uterine coring device 10, the prepared subassembly 146 is placed within the first housing half 148 aligning the outer tube bushing 50 with distal housing recess 156 and the inner tube bushing 46 with the proximal housing recess 154. Meanwhile, flex rack subassembly 102 is aligned with the central housing recess 158 along axis 170 and the lever axle corresponding to lever axle 118 (not shown, but on opposite side of view) is inserted into the hole for lever axle 152. Spring hole 168 of spring 164 is then placed onto pin 160 along axis 162. Finally, the second housing half 150 is placed over the device along axis 170 to complete assembly. Second housing half 150, while not visible in this view, has features corresponding to the hole for the lever axle 152, the proximal housing recess 154, distal housing recess 156, the central housing recess 158, and mounting hole 159 for a pin 160. Once the second housing half 150 is attached to the first housing half 148, the corresponding features on the second housing half 150 mate similarly with the subassembly 146 as they do on first housing half 148. The housing halves 148, 150 can be held fixedly in place by adhesive, fasteners, screws, or other means known to those skilled in the art.

Figure 3:
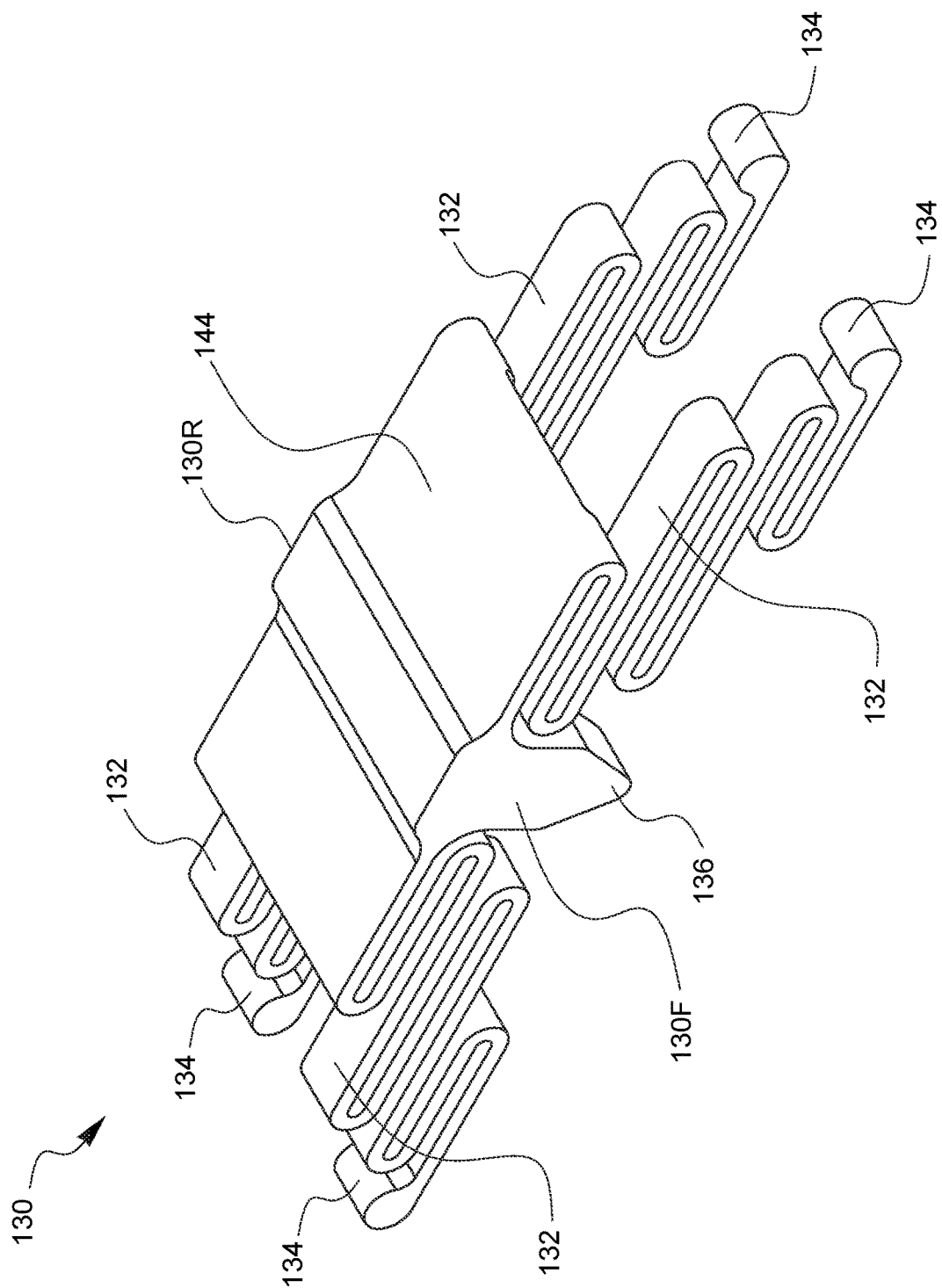
FIG. 3 is a top-left-front perspective view of a synchronizing lock.

FIG. 3 is a top-left-front perspective view of a synchronizing lock shown in FIG. 2J. The synchronizing lock spring 130 has a top surface 144 from which four spring elements 132 and two synchronizing lock spring teeth 136 extend. Each spring element 132 terminates in a spring end 134. The front face 130F and rear face 130R of the synchronizing lock spring 130 each have a tooth 136 configured to engage the inner tube symmetrical gear 44 or outer tube symmetrical gear 52 in the minimally invasive uterine coring device 10 disclosed herein. The four spring elements 132 in the synchronizing lock spring 130 are configured to provide the top surface 144 with the property of out of plane flexure or flexural bending for the purpose of allowing the synchronizing lock spring teeth 136 to ride along in the inner tube symmetrical gear 44 and outer tube symmetrical gear 52 as the inner tube 24 and outer tube 22 are counter-rotating during operation. Upon release of the actuator lever 38, the synchronizing lock spring teeth 136 engage the corresponding teeth 44T, 52T of the inner tube symmetrical gear 44 and outer tube symmetrical gear 52 and reset the inner tube 24 and outer tube 22 to a specific position. In this described embodiment, the teeth 44T, 52T are aligned with a feature on the sharpened ends 26, 28 of the inner tube 24 and outer tube 22. This would align the sharpened ends 26, 28 in a manner which would minimize potential trauma to the patient from non-aligned features at the ends of the tubes 22, 24. In the present embodiment, having a scalloped feature of the sharpened ends 26, 28 not aligned or overlapped could minimize trauma during a reset or resting position of the minimally invasive uterine coring device 10. As another example embodiment, the outer tube 22 could have shielding elements at the end of the outer tube 22 in place of sharpened ends. This configuration would cover the sharpened ends 26 of the inner tube 24 and prevent them from cutting tissue until the actuator lever 38 was squeezed and the minimally invasive uterine coring device 10 was ready for use. The spring ends 134 are configured to be fixed into the first and second housing halves 148, 150 as shown in the embodiments herein by a fastener or by mating with a matching or receiving recess in the instrument first and second housing halves 148, 150. The synchronizing lock spring 130 can also be characterized as a spring. A spring can be defined as an element that stores and releases energy. The spring stores energy when deformed and releases energy when returned to its original state prior to deformation. A spring may also be referred to as a biasing element, since it may introduce bias to another element when deformed by it. A spring may also be referred to as a resilient element or resilient member in terms of it having the inherent property of withstanding shock or movement without permanent deformation. FIGS. 4A, 4B, 4C, 4D, 4E, and 4F are front, left side, right side, rear, top, and bottom elevational views, respectively, of the synchronizing lock of FIG. 3.

FIGS. 5A-5D are partial cross-sectional views illustrating the operational principles of the minimally invasive uterine coring device of FIG. 1. 5A is a partial cross-sectional side view of the minimally invasive uterine coring device of FIG. 1 in a released or reset position. In this view, the actuator lever 38 is positioned away from the handle 36 of the minimally invasive uterine coring device 10 and the actuator 122 is positioned within the opening 104 of the flex rack subassembly 102. While the features on the sharpened ends 26, 28 of the outer tube 22 and the inner tube 24 (not shown in this view) are shown as aligned in this view, other embodiments may exist where the features on the sharpened ends 26, 28 of the outer tube 22 and the inner tube 24 are not in alignment.

Figure 5A:
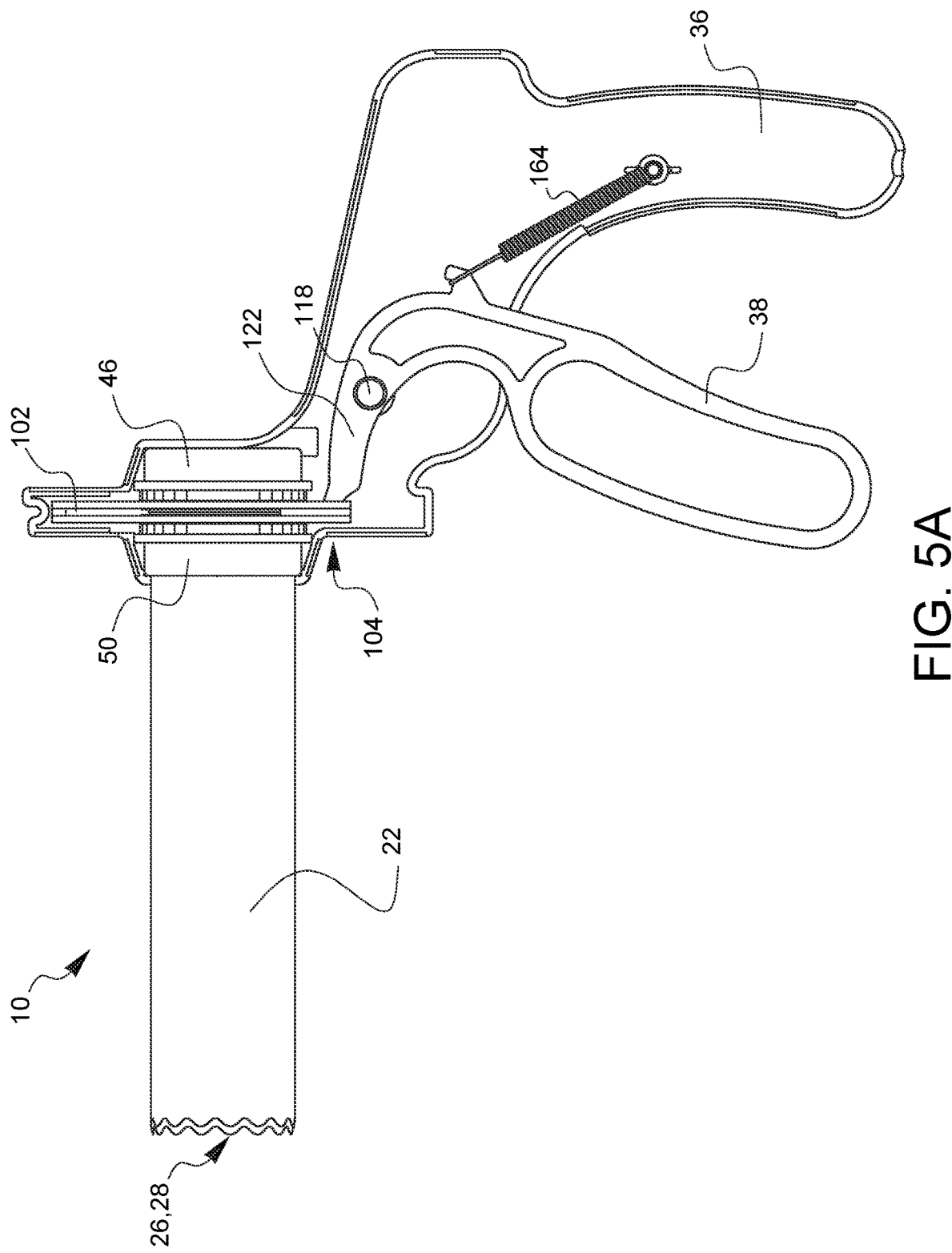
FIGS. 5A-5D are partial cross-sectional views illustrating the operational principles of the minimally invasive uterine coring device of FIG. 1.
Figure 5B:
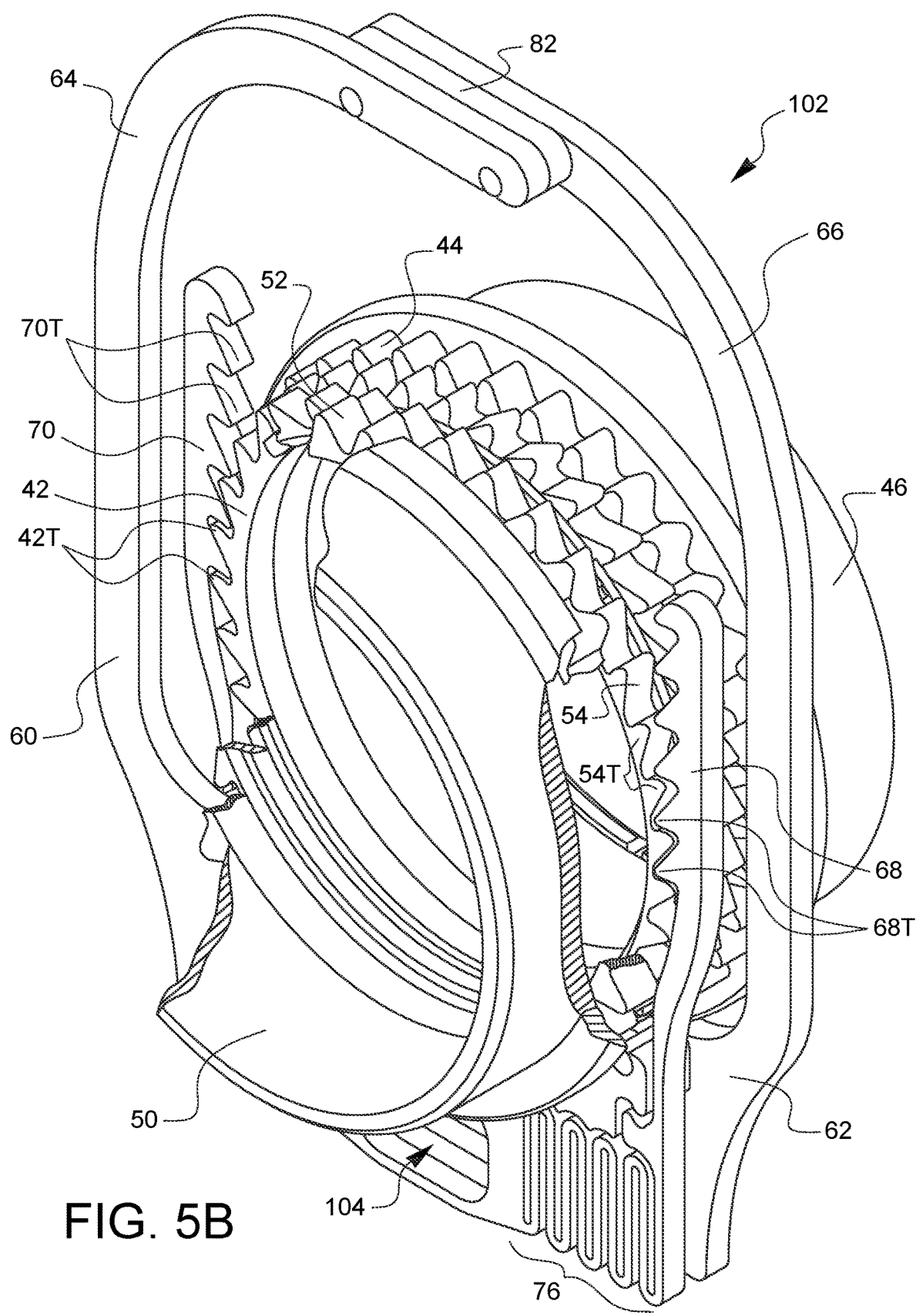

FIG. 5B is partial cross-section of a perspective view of the flex rack and tube subassembly of the minimally invasive uterine coring device of FIG. 1 in a released or reset position. In this released or reset position, the teeth 52T of the outer tube symmetrical gear 52 and the teeth 44T of the inner tube symmetrical gear 44 are aligned. In alternate embodiments of the minimally invasive uterine coring device 10 disclosed herein, the teeth 52T of the outer tube symmetrical gear 52 and the teeth 44T of the inner tube symmetrical gear 44 may not be aligned. The asymmetrical teeth 42T of outer tube asymmetrical gear 42 are intermeshed or engaged with teeth 70T on the flex rack arm 70 and the asymmetrical teeth 54T of outer tube asymmetrical gear 54 are intermeshed or engaged with the teeth 68T on the flex rack arm 68. While actuator 122 is not shown in this view for purposes of clarity, the actuator 122 would be engaged in opening 104 on the flex rack subassembly 102 in this released or reset position. It may be desirable for the symmetrical teeth 52T of outer tube symmetrical gear 52 and the symmetrical teeth 44T inner tube symmetrical gear 44 to align with a specific feature on the end of the outer tube 22 and the inner tube 24, respectively.

Figure 5C:
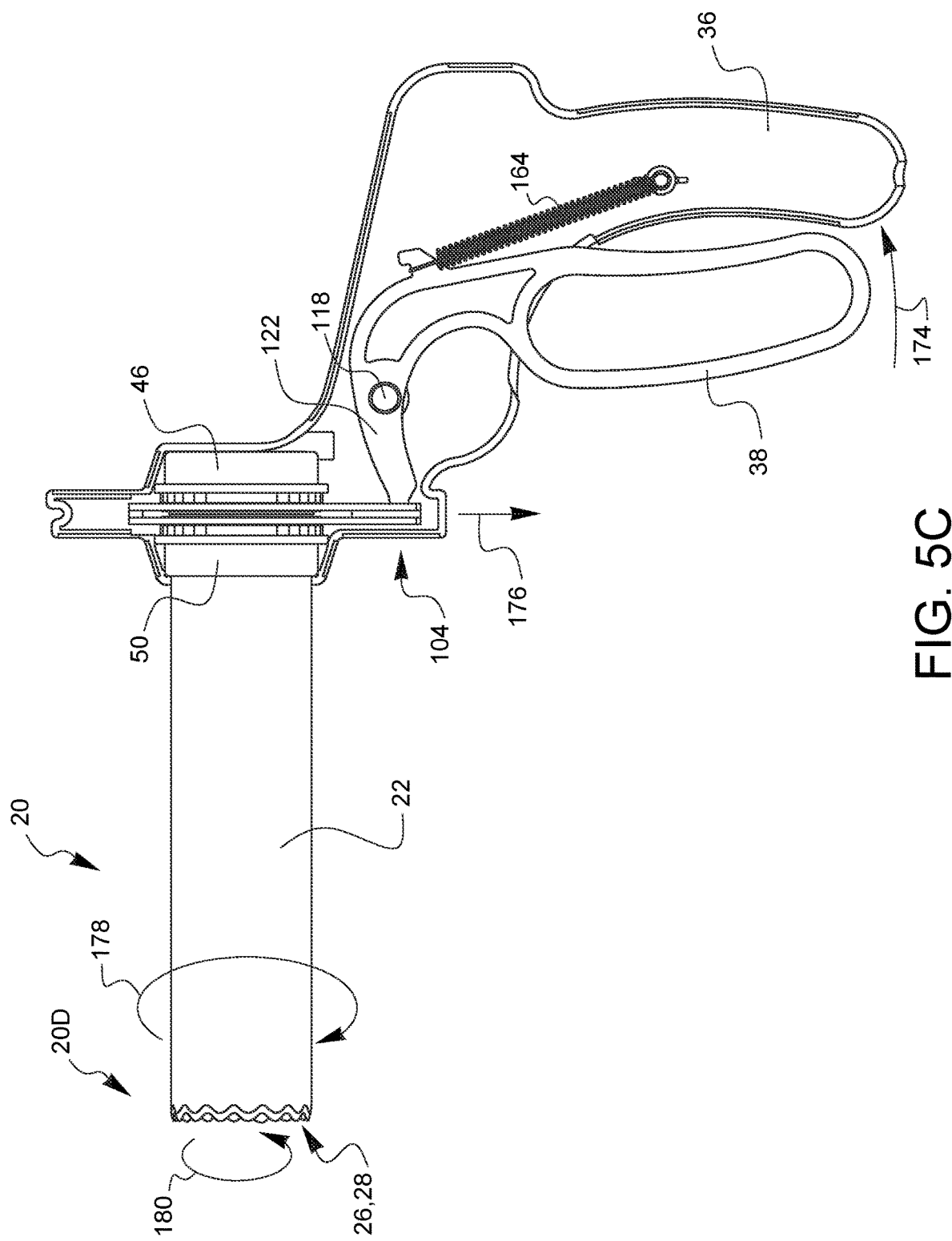

FIG. 5C is a partial cross-sectional side view of the minimally invasive uterine coring device of FIG. 1 in a squeezed position. In this view, the actuator lever 38 is squeezed in a direction 174 towards the handle 36 of the minimally invasive uterine coring device 10. This action by the user moves the actuator 122 about the pivot point at lever axle 118. The actuator 122 is positioned within the opening 104 of the flex rack subassembly 102, and moves in a direction 176 downwards. This in turn pulls the flex rack subassembly 102 downwards in a direction 176 as well. This actuation of the flex rack subassembly 102 in a downward direction 176 rotates the outer tube 22 in a direction 178 while the same actuation of the flex rack subassembly 102 simultaneously or nearly simultaneously rotates the inner tube 24 in a direction 180. This counter-rotation of the sharpened ends 26, 28 of the tubes 22, 24 effects a cutting action at the distal end 20D of the tube or blade assembly 20 of the minimally invasive uterine coring device 10. Further details of how this actuation occurs are discussed in regard to FIG. 5D. While the tubes 22, 24 are shown rotating in their respective directions 178, 180, it should be noted that alternate embodiments of the minimally invasive uterine coring device 10 could have the tubes counter-rotating in the opposite direction depending on the arrangement of the components and features further addressed in regard to FIG. 5D. While the features on the sharpened ends 26, 28 of the outer tube 22 and the inner tube 24 (not shown in this view) are shown as aligned in this view, other embodiments may exist where the features on the sharpened ends 26, 28 of the outer tube 22 and the inner tube 24 are not in alignment at the moment of actuation of the minimally invasive uterine coring device 10 by the actuator lever 38.

Figure 5D:
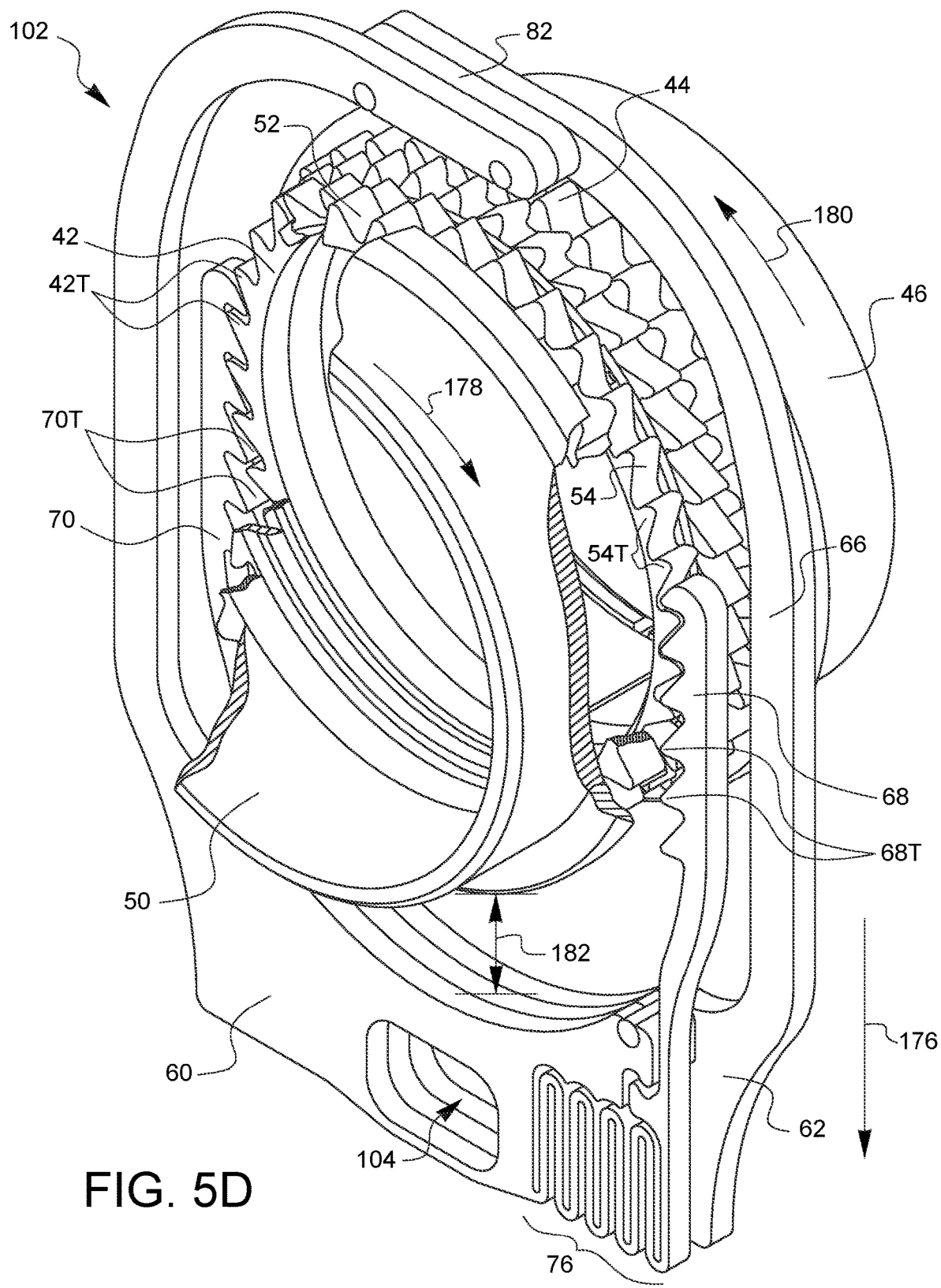

FIG. 5D is partial cross-section of a perspective view of the flex rack and tube subassembly of the minimally invasive uterine coring device of FIG. 1 in a squeezed position. In this squeezed position, the teeth 52T of the outer tube symmetrical gear 52 and the teeth 44T of the inner tube symmetrical gear 44 are aligned. The asymmetrical teeth 42T of outer tube asymmetrical gear 42 remain intermeshed or engaged with teeth 70T on the flex rack arm 70 and the asymmetrical teeth 54T of outer tube asymmetrical gear 54 remain intermeshed or engaged with the teeth 68T on the flex rack arm 68. However, upon actuation of the actuator lever 38, and therefore the movement of the actuator 122 and flex rack subassembly 102 in a direction 176 downward, the intermeshed teeth 68T on the flex rack arm 68 have transferred movement of the flex rack subassembly 102 to rotate the outer tube asymmetrical gear 54 via the asymmetrical teeth 54T, and thus rotate the outer tube 22 in direction 178, as also shown in FIG. 5C. Simultaneously, or nearly simultaneously, the movement of the actuator 122 and flex rack subassembly 102 in a direction 176 downward, the intermeshed teeth of teeth 70T have also transferred movement of the flex rack subassembly 102 to rotate the inner tube asymmetrical gear 42 via the asymmetrical teeth 42T and thus rotate the inner tube 24 in direction 180, as also shown in FIG. 5C. While actuator 122 is not shown in this view for purposes of clarity, the actuator 122 would be engaged in opening 104 on the flex rack subassembly 102 in this squeezed position.

Upon release of the actuator lever 38, the tension on spring 164 returns actuator lever 38 and therefore actuator 122 and flex rack subassembly 102 to the position shown in FIGS. 5A and 5B. Meanwhile, the flex rack spring element 76 and flex rack spring element 78 allow the flex rack arms 68, 70 to flex away from the inward side 69, 71 (refer to FIG. 2E) of the flex rack subassembly 102 and due to the nature of the asymmetric gear teeth pairs 68T, 54T and 70T, 42T the flex rack subassembly 102 returns to the position shown in FIGS. 5A and 5B while the flex rack arm 68 and flex rack arm 70 move upwards without engaging the outer tube asymmetrical gear 54 or inner tube asymmetrical gear 42, respectively. This leaves the inner tube 24 and outer tube 22 in the same position they were located after the squeezing step described in regard to FIGS. 5C and 5D. The result of the described functional arrangement of this embodiment is that the minimally invasive uterine coring device 10 will only engage and cut tissue when the lever is squeezed.

Figure 6A:
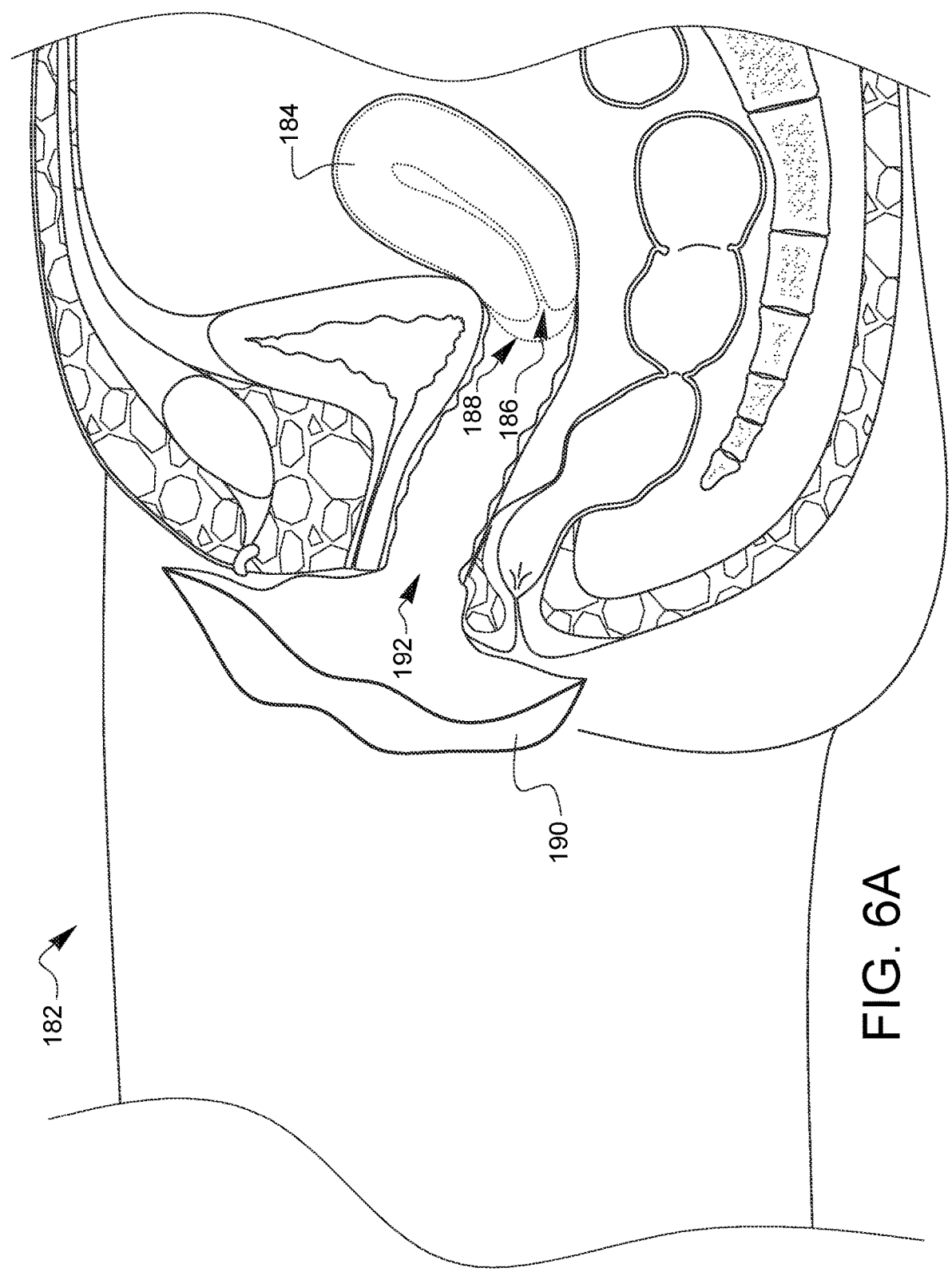
FIGS. 6A-6G are a series of orthogonal side views of the human anatomy taken along the midline, also known as a sagittal view, illustrating a surgical sequence using the minimally invasive uterine coring device of FIG. 1.

FIGS. 6A-6G are a series of orthogonal side views of the human anatomy taken along the midline, also known as a sagittal view, illustrating a surgical sequence using the minimally invasive uterine coring device of FIG. 1. FIG. 6A is a sagittal view of a patient and several related internal organs and anatomical features after a colpotomy has been performed. A patient 182 is shown with the location of a recent colpotomy incision 188 and a separated uterus 184 having a cervix 186. A specimen encapsulation bag 190 is shown inserted into a vaginal canal 192, such that the specimen encapsulation bag 190 has encapsulated the uterus 184. The specimen encapsulation bag 190 is also known as an endoscopic bag, but any suitable and safe encapsulation device could be used. The colpotomy and hysterectomy may have been performed by a minimally invasive surgical technique, aided by the use of an FS® SOUND and FORNISEE® as sold by LSI Solutions, Inc.

Figure 6B:
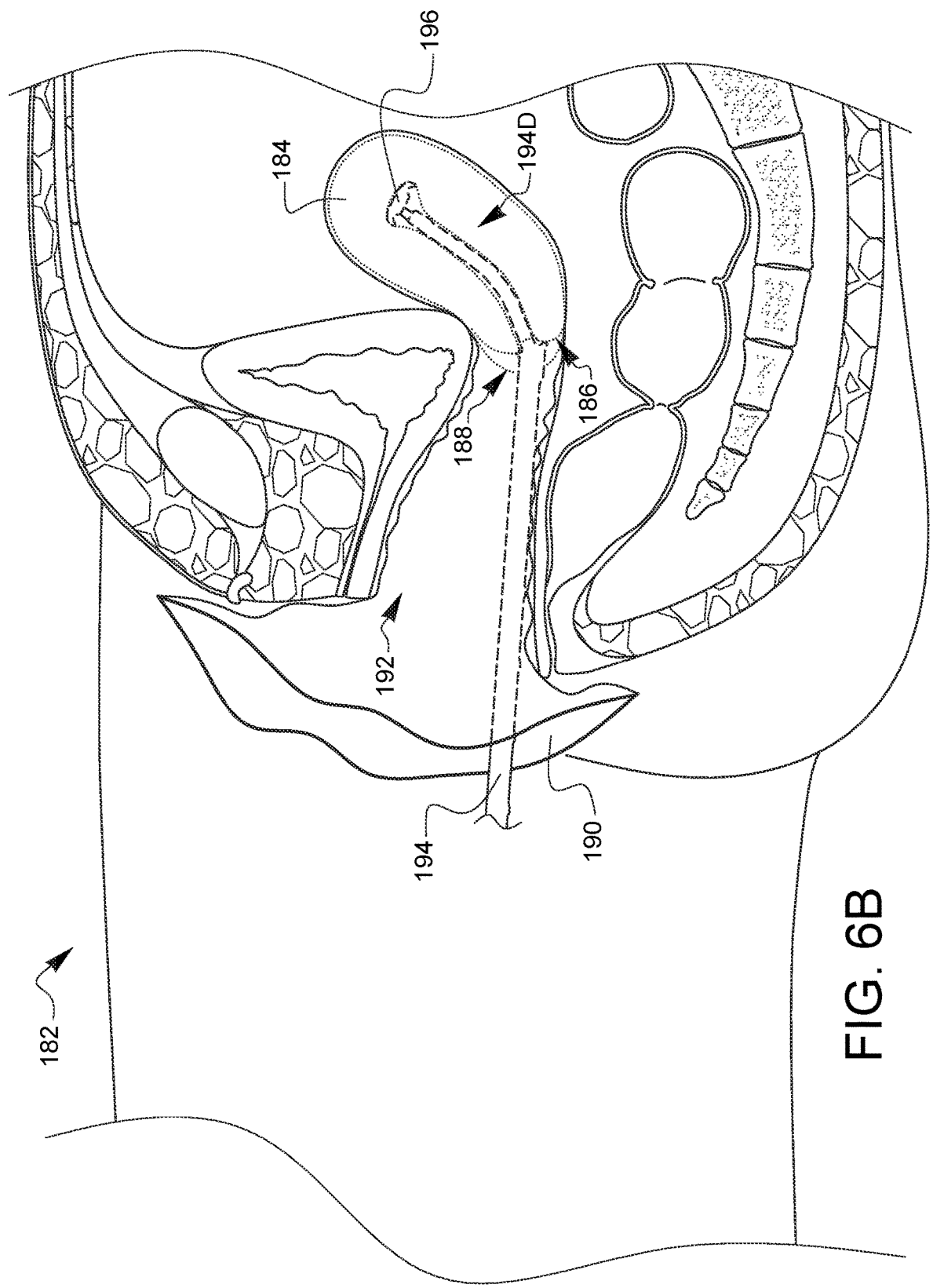

FIG. 6B is an anatomical sagittal view illustrating an intrauterine sound inserted into the encapsulation bag-lined vaginal canal and anchored at a distal end into the uterine sample. The patient 182 is shown with an intrauterine sound 194 with an intrauterine sound anchor 196 at the distal end 194D of the intrauterine sound 194 having been advanced into the uterus 184 at the cervix 186. The intrauterine sound anchor 196 has been deployed to anchor the uterus 184. It should be noted that the intrauterine sound 194, uterus 184, is still encapsulated within the specimen encapsulation bag 190 inside the vaginal canal 192.

Figure 6C:
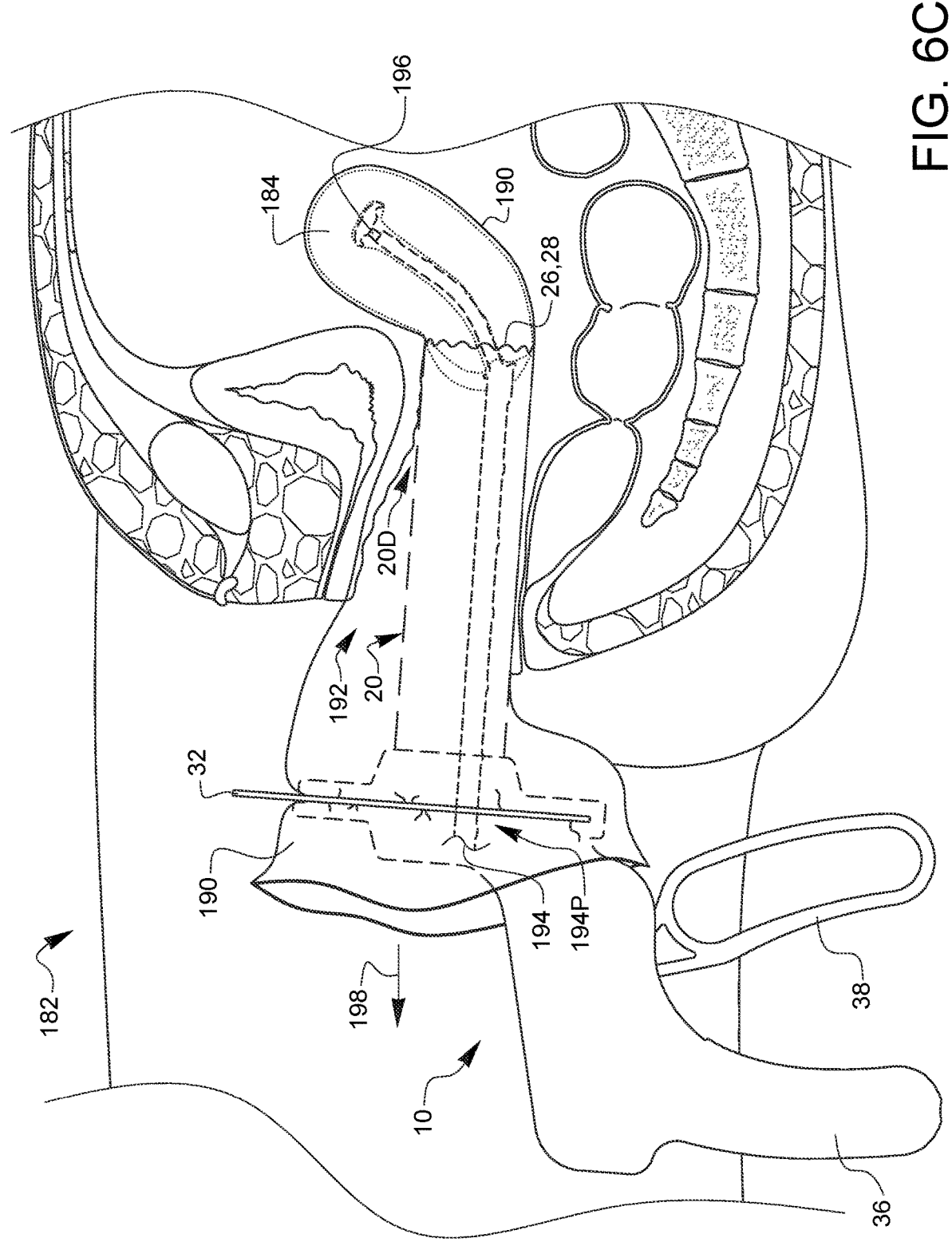

FIG. 6C is an anatomical sagittal view illustrating a minimally invasive uterine coring device positioned onto a sound device and advanced into a vaginal canal. The distal end 20D of the blade assembly 20 of the minimally invasive uterine coring device 10 of FIG. 1 has been passed over the proximal end 194D of the intrauterine sound 194 until the sharpened ends 26, 28 of the minimally uterine coring device 10 are in contact with the uterus 184. Once the uterine coring device 10 has been advanced into the vaginal canal 192, the specimen encapsulation bag 190 has been secured to the uterine coring device 10 using the retaining clip 32 as described in regard to FIG. 1. The respective positions of the handle 36 and actuator lever 38 of the uterine coring device 10 indicate that it is in a released or reset position as described previously in regard to FIG. 5A and 5B. The intrauterine sound 194 is pulled in a proximal direction 198 relative to the patient 182 to appropriately position the uterus 184 at the sharpened ends 26, 28 of the uterine coring device 10.

Figure 6D:
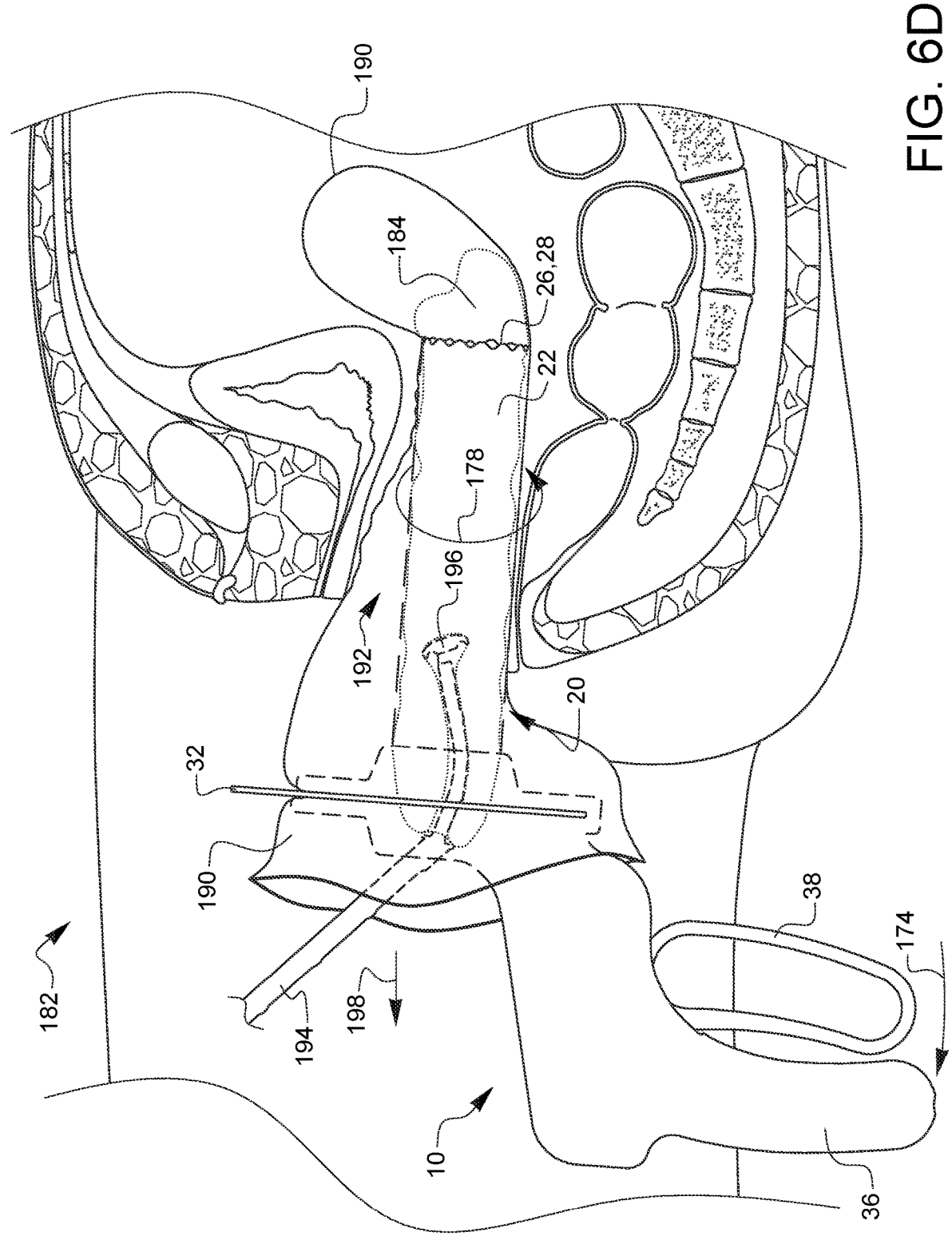

FIG. 6D is an anatomical sagittal view illustrating a minimally invasive uterine coring device positioned onto a sound device, advanced into a vaginal canal and coring a uterus. The minimally invasive uterine coring device 10 is still advanced into the vaginal canal 192. Shown here is the device in an intermediate state of uterine coring, with the actuator lever 38 moved in a direction 174 towards the handle 36, indicating a squeezed state as described in regard to FIGS. 5C and 5D. The intrauterine sound 194 has been pulled further in a proximal direction 198 relative to the patient 182, which begins to remove the uterus 184 and its core from the patient 182 via the center of the hollow tube pair that makes up the blade assembly 20. The outer tube 22 has rotated in direction 178 as a result of squeezing the actuator lever 38 towards the handle 36. Although not shown in this view, it should be understood that inner tube 24 is simultaneously rotating in the opposite direction as outer tube 22. The squeezing and release of the actuator lever 38 while pulling on the intrauterine sound 194 is repeated until appropriate coring and removal of the uterus 184 has been completed. Once the core removal is completed, the intrauterine sound 194 and uterine core are passed through the center of the uterine coring device 10.

Figure 6E:
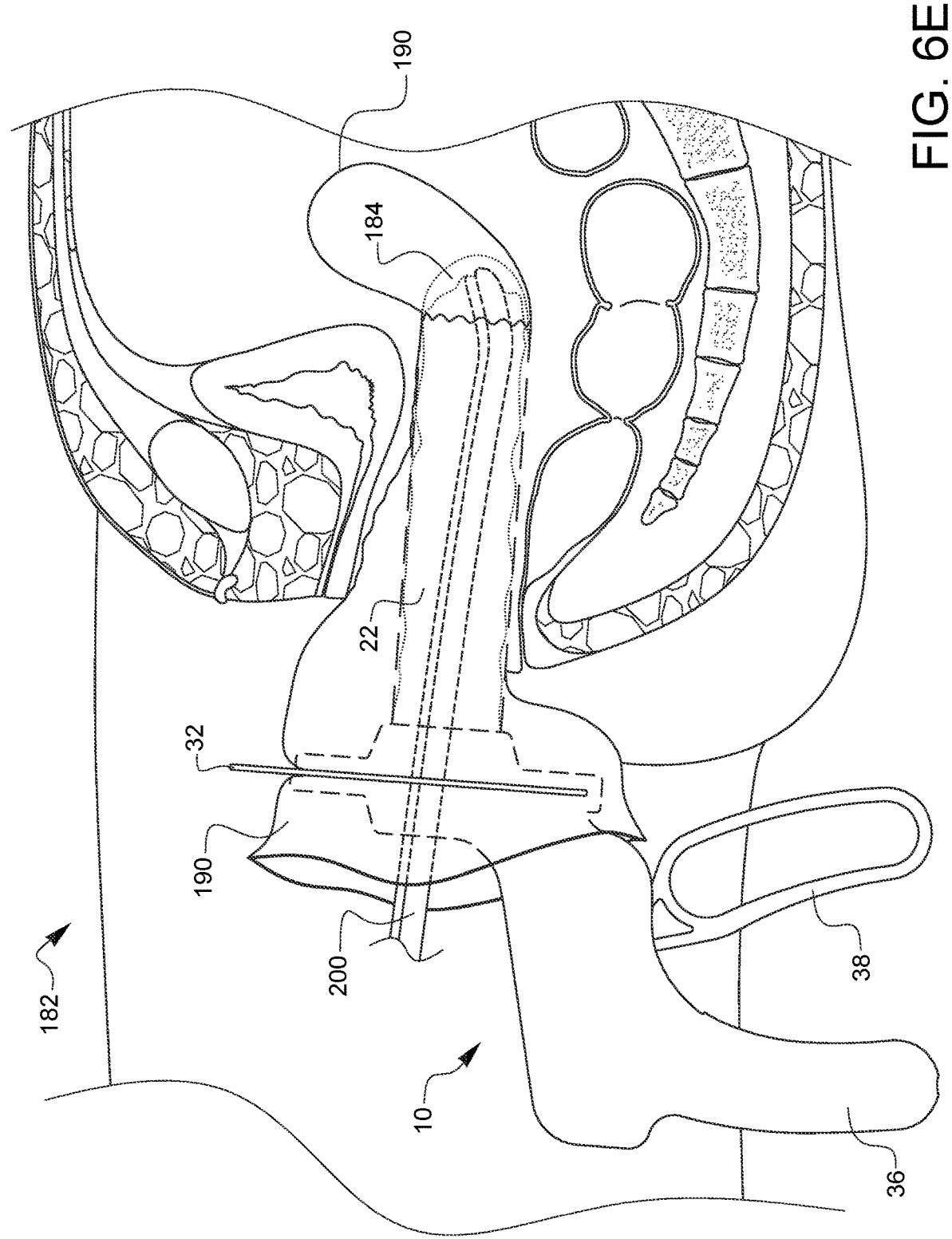

FIG. 6E is an anatomical sagittal view illustrating a minimally invasive uterine coring device advanced into a vaginal canal with a tenaculum advanced through the center of the minimally invasive uterine coring device. On the occasion that continued coring needs to occur, a tenaculum, forceps 200, or other grasper is passed through the uterine coring device 10 in order to grasp the remaining uterus 184. While the uterine coring device 10 is shown in a released or reset position in this view, it should be understood that continued squeezing of the actuator lever 38 would continue counter-rotation of the inner tube 24 and outer tube 22 within the blade assembly to enable continued coring as previously described.

Figure 6F:
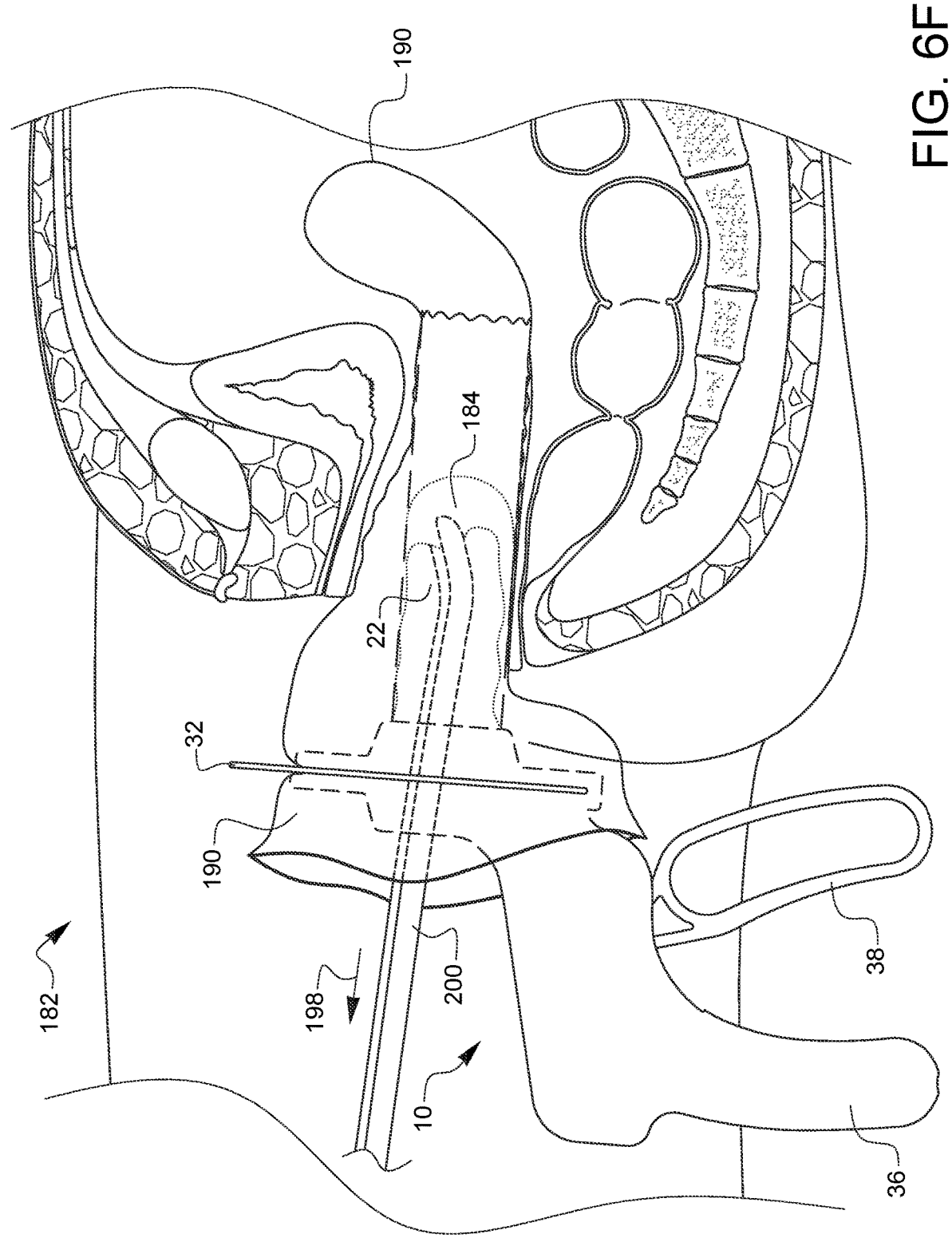

FIG. 6F is an anatomical sagittal view illustrating the removal of the uterine specimen transvaginally by drawing the uterine coring device, the specimen encapsulation bag, and the remaining encapsulated uterine specimen. Upon completion of the uterine coring, the minimally invasive uterine coring device 10, forceps 200, specimen encapsulation bag 190 and uterus 184 are removed transvaginally in a proximal direction 198 relative to the patient 182.

Figure 6G:
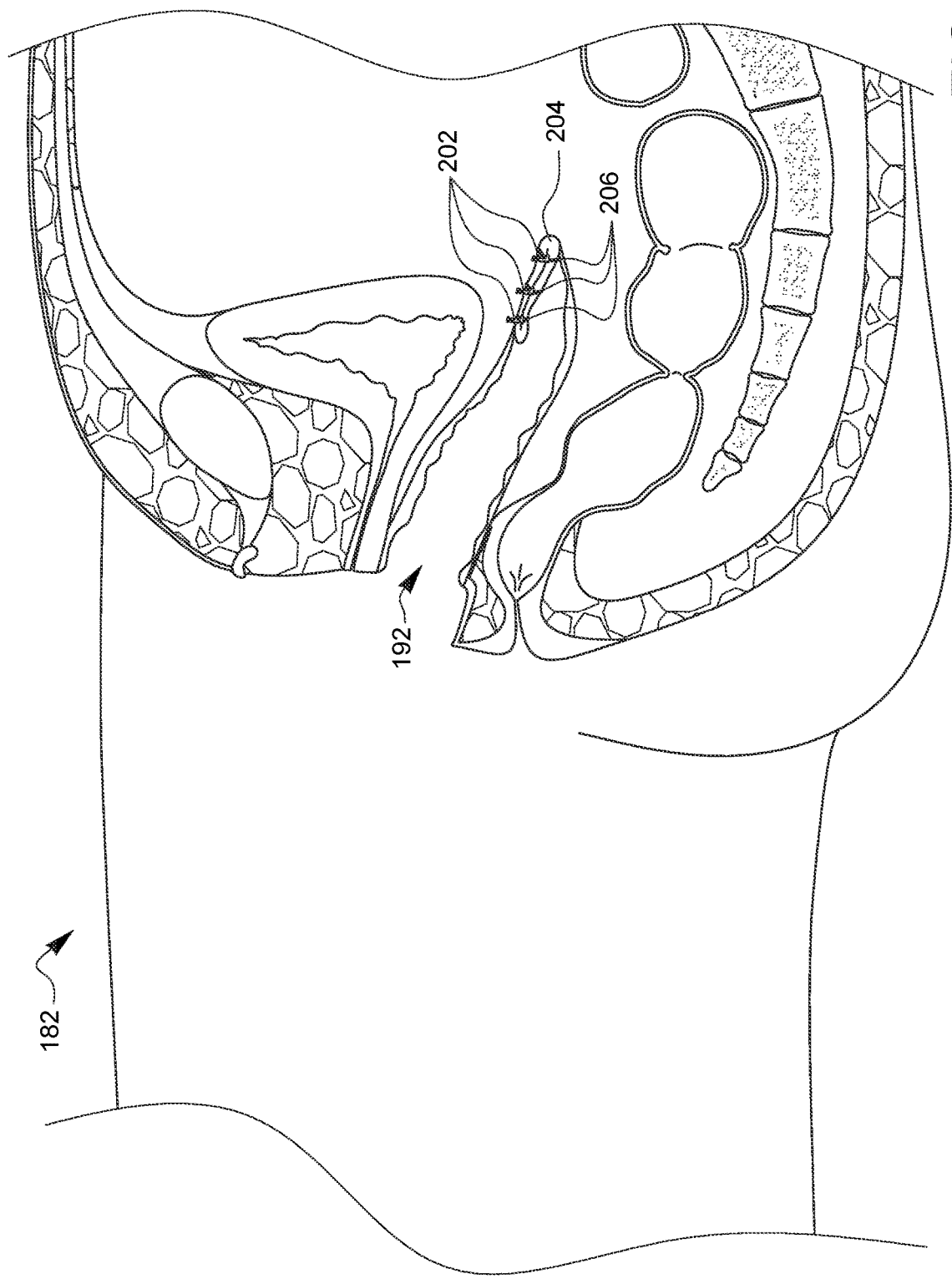

FIG. 6G is an anatomical sagittal view illustrating the patient after removal of the minimally invasive uterine coring device along with any remaining uterine specimen, and after a vaginal cuff closure has been performed. Patient 182 is shown after a vaginal cuff 204 closure. After the colpotomy has been closed with mattress sutures, the suture ends 206 are then secured with a mechanical fastener 202 such Ti-KNOT® and COR-KNOT® as sold by LSI Solutions, Inc. While a PNEUIMOSTOP® as sold by LSI Solutions, Inc. may be placed in the vaginal canal 192 for re-establishment of the pneumoperitoneum to enable vaginal cuff closure, one is not shown in this view.

Figure 7A:
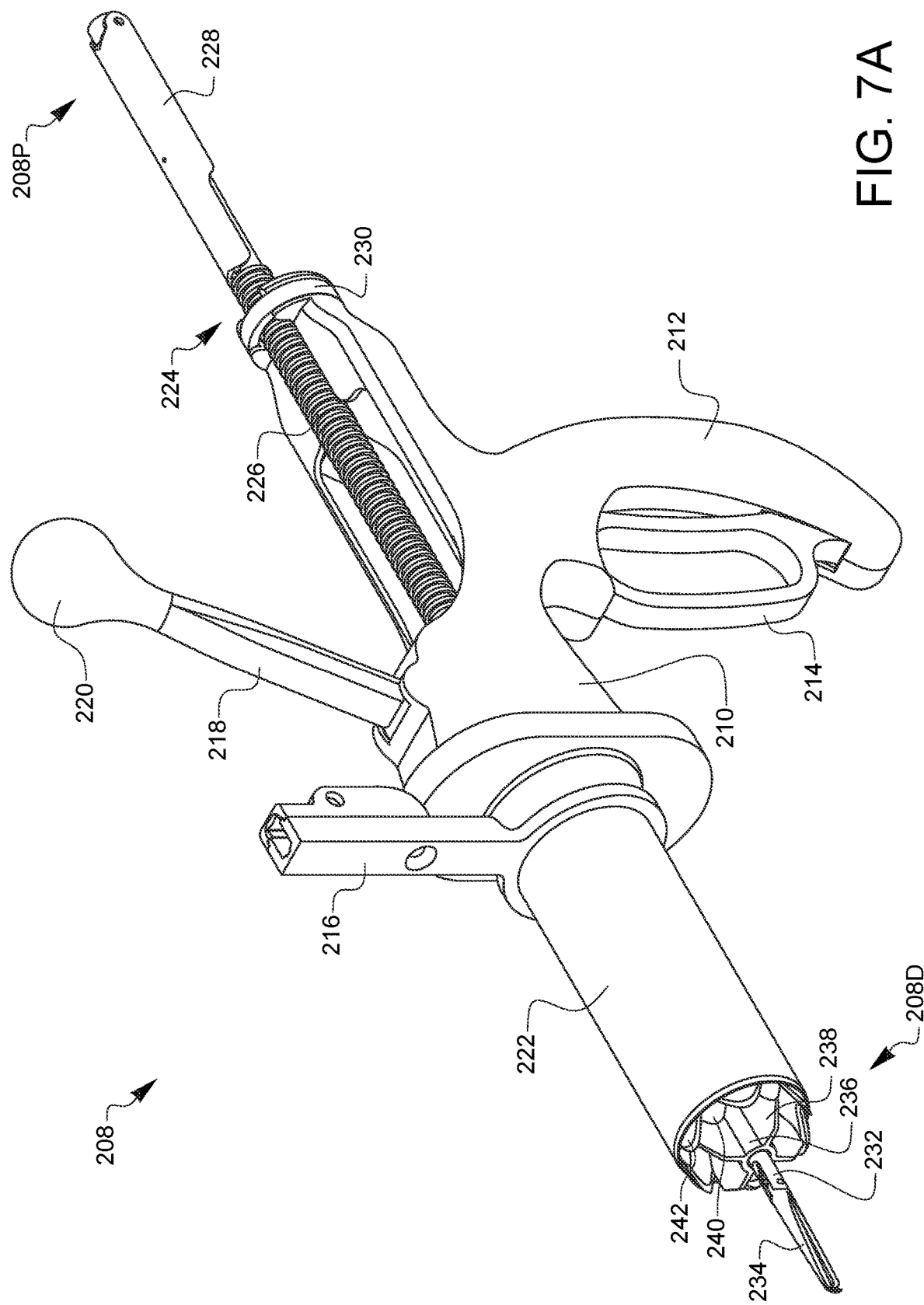
FIGS. 7A-7C are top-left-front perspective views of the components of an embodiment of a surgical specimen retrieval system.
Figure 7B:
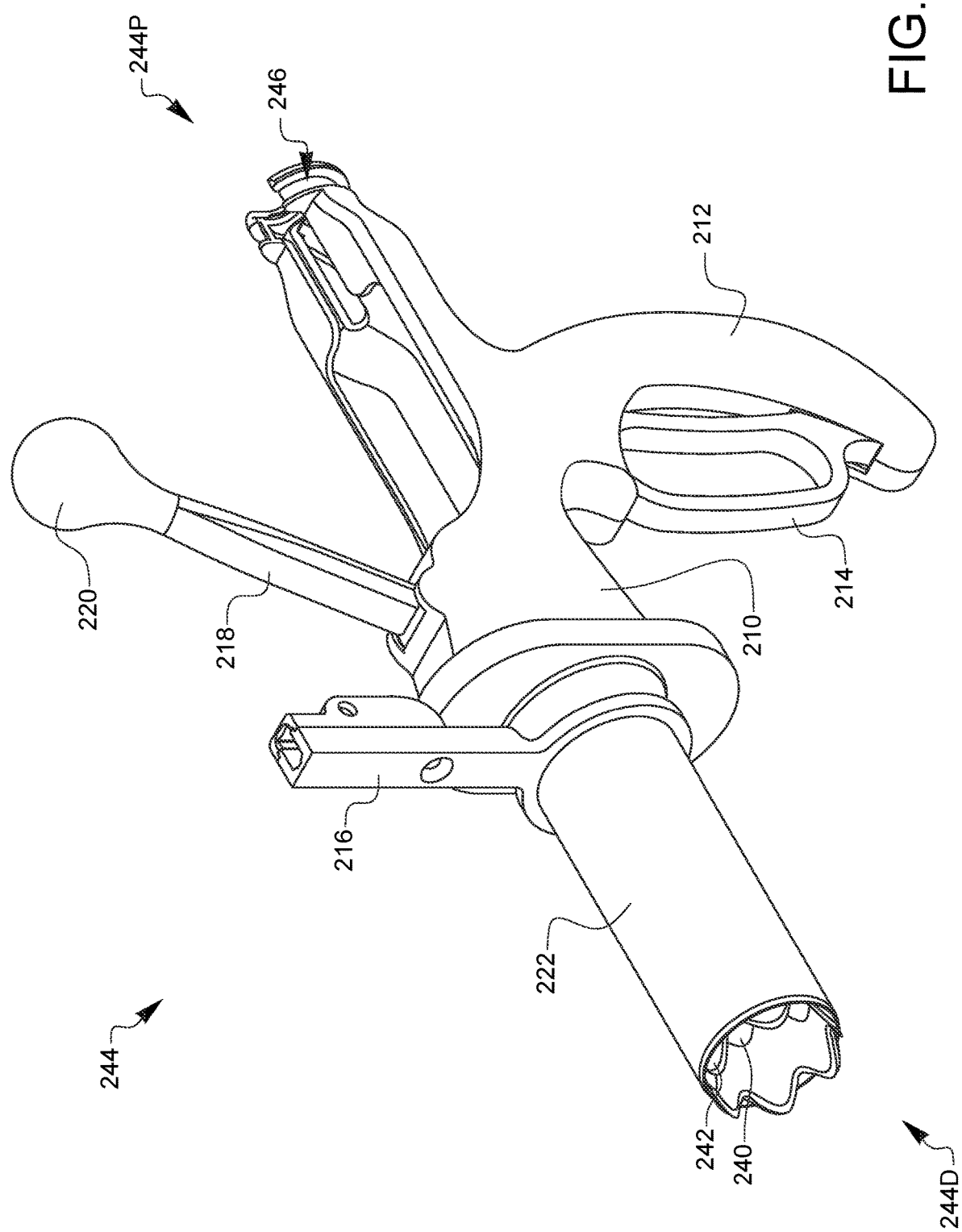
Figure 7C:
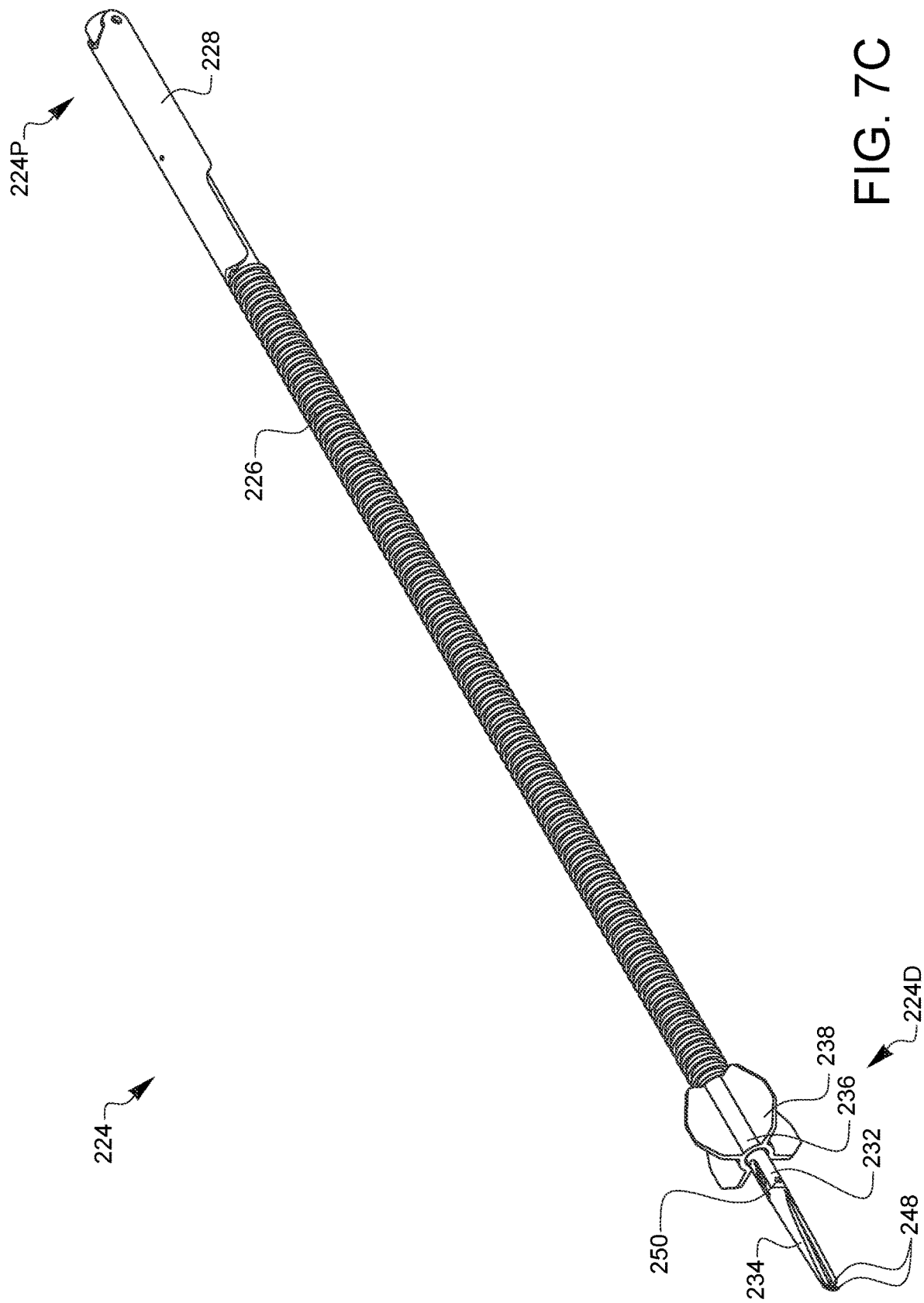

FIGS. 7A-7C are top-left-front perspective views of the components of an embodiment of a surgical specimen retrieval system. FIG. 7A is a top-left-front perspective view of an alternate embodiment of a surgical specimen retrieval system 208, similar to the uterine coring device 10 discussed herein. The specimen retrieval system 208 has an outer housing 210 which defines a handle 212 for manual holding of the instrument during operation. The housing 210 holds a throttle 218 or throttle actuator 218 having a throttle knob 220, a tube assembly (not visible in this view), an actuation lever 214 configured to counter-rotate the tube assembly, and a geared tenaculum 224. The geared tenaculum 224 has a tenaculum shaft 232 having a central geared tenaculum shaft portion 224 connected to a tenaculum lever 228 on the proximal end 208 P of the specimen retrieval system 208, and a center guide 236 and pair of grasper arms 234 on the distal end 208D. The center guide 236 further defines several center guide fins 238 configured to maintain the grasper arms 234 and tenaculum shaft 232 in a centered position within the tube assembly of the specimen retrieval system 208. A retainer ring 230 towards the proximal end 208P of the specimen retrieval system 208 holds the geared tenaculum 224 in place within the housing 210 of the specimen retrieval system 208. A cannula 222 is shown covering the tube assembly, not visible in this view, of the specimen retrieval system 208 which also defines a cannula adapter 216. The cannula 222 is configured to cover the tube assembly to provide an added safety measure from unintentional trauma to a patient while in operation. The cannula adapter 216 is configured to attach or mount the cannula 222, and therefore the entire specimen retrieval system 208 to a surgical equipment holder or other surgical mounting device. This can fix the position of the specimen retrieval system 208 in place during operation or during a minimally invasive surgical procedure.

FIG. 7B is a top-left-front perspective view of a specimen coring device 244, a portion of the specimen retrieval system 208 of FIG. 7A. The specimen coring device 244 portion of the specimen retrieval system 208 includes the housing 210, handle 212, actuation lever 214, throttle 218, throttle knob 220, inner tube and outer tube. While the inner tube and outer tube are not shown in this view — the inner tube teeth 240 and the outer tube teeth 242 are visible—they will be described in more detail later. The inner tube teeth 240 and the outer tube teeth 242 protrude from the cannula 222, which covers the outer tube. The cannula adapter 216, which is attached to the cannula 222 is also shown. The cannula adapter 216 can be attached by adhesion, welding or other means of fixedly attaching the cannula adapter 216 to the cannula 222. The cannula 222 and cannula adapter 216 may be made of stainless steel, plastic, or other material suitable for use and potential re-use (after sterilization) in a surgical environment.

FIG. 7C is a top-left-front perspective view of a specimen retrieval tenaculum 224. The specimen retrieval tenaculum 224 is a geared tenaculum. The geared tenaculum 224 has a tenaculum shaft 232 having a central geared tenaculum shaft 226 portion connected to a tenaculum lever 228 on the proximal end 224P of the specimen retrieval tenaculum 224, and a center guide 236 having several center guide fins 238, and pair of grasper arms 234 on the distal end 224D. The geared tenaculum 224 is shown in the closed position, characterized by the tenaculum lever 228 being close to the tenaculum shaft 232 and the grasper arms 234 being in close proximity to one another, and capable of grasping tissue in between the grasper arms 234.

Figure 8A:
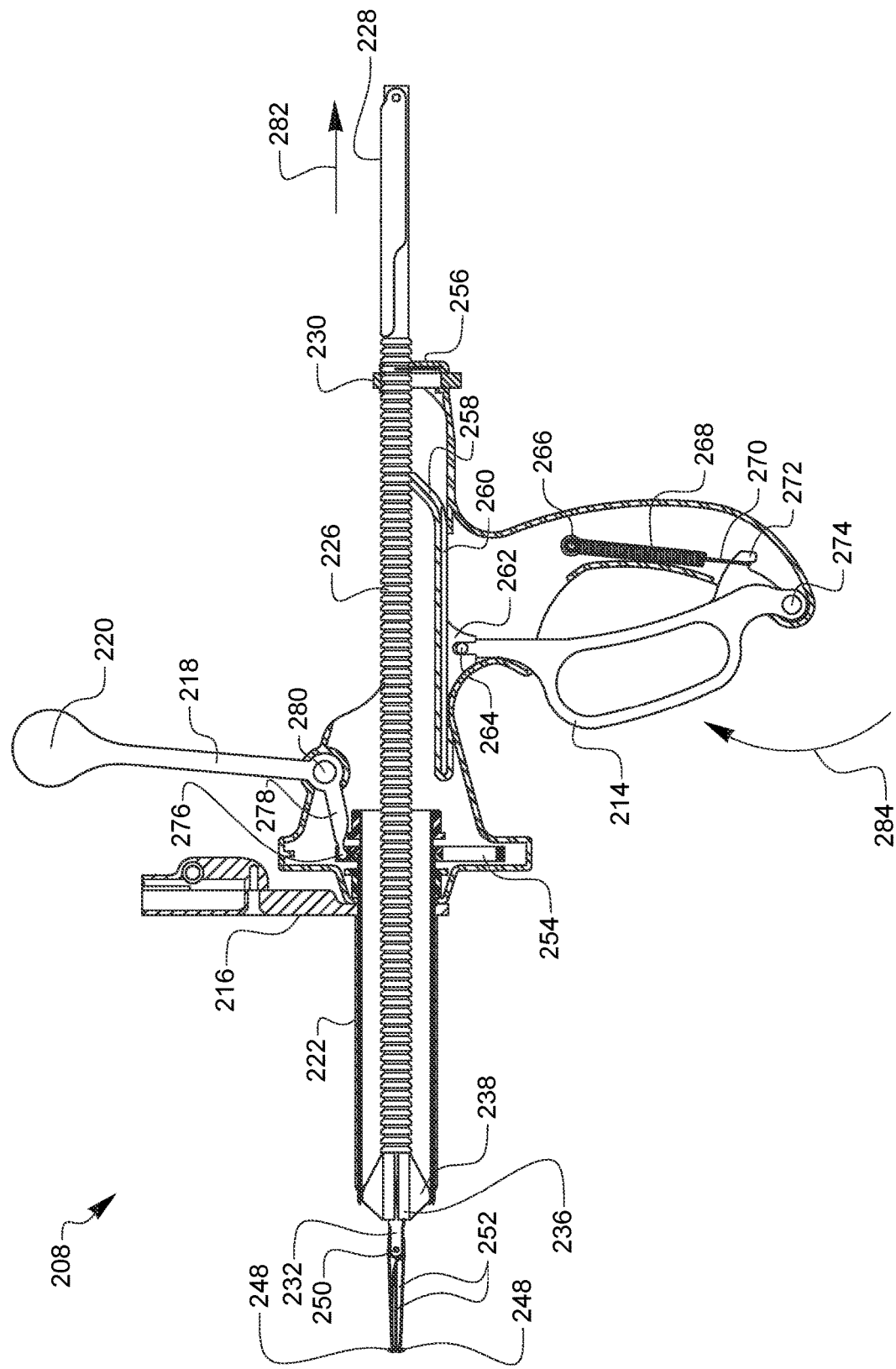
FIGS. 8A-8F are a series of partial cross-sectional views illustrating the operational principles of the specimen retrieval system of FIG. 7A.
Figure 8B:
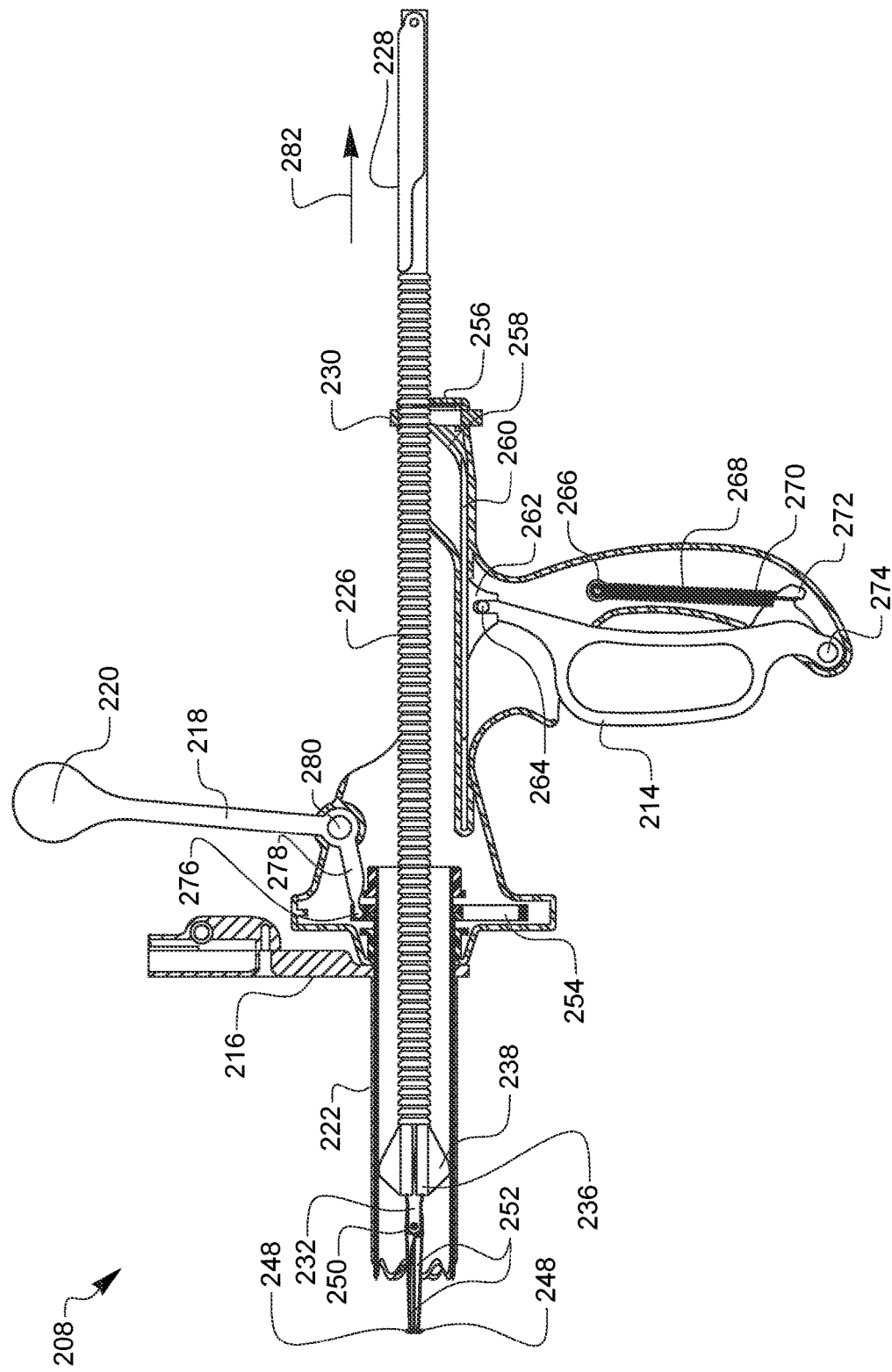

FIGS. 8A-8F are a series of partial cross-sectional views illustrating the operational principles of the specimen retrieval system of FIG. 7A. FIG. 8A and 8B are partial cross-sectional side views of the surgical specimen retrieval system 208 of FIG. 7A, illustrating the operational motion of the actuation lever 214 and tenaculum 224 in a released position and actuated position, respectively. FIG. 8A shows the surgical specimen retrieval system 208 in the released position, with the actuation lever 214 in a position away from the handle 212. Upon squeezing of the actuation lever 214 in a direction towards 284 the handle 212, the actuation lever 214 moves about a lever pivot 274 located in the lower portion of the handle 212. At the opposite end of the actuation lever 214 is a tenaculum actuator pivot 264 that is pivotably coupled to an actuator coupler 262 in a tenaculum actuator 260. When the actuation lever 214 is squeezed, the tenaculum actuator 260 is moved in a proximal direction 282, whereby a tenaculum actuator tab 258 at the proximal end of the tenaculum actuator 260 engages with one or more gears in the geared tenaculum shaft 226 and pushes the tenaculum 224 in a proximal direction 282. The tenaculum actuator 260 is a biasing member, biasing the tenaculum actuator tab 258 against the asymmetrical gears on the geared tenaculum shaft 226 portion of the tenaculum shaft 224. When the tenaculum actuator tab 258 moves in a proximal direction 282, it pulls the tenaculum 224 in a proximal direction 282. When the tenaculum lever 228, and therefore the grasper arms 252 are also moved to a closed position, any tissue grasped within the grasper arms 252 would be pulled in a proximal direction 282 in a controlled manner and the tenaculum actuator is configured such that activating the tenaculum actuator will advance tissue into the sharpened ends of the inner and outer tubes for sectioning or coring by the sharpened ends of the counter-rotating inner tube and outer tubes held within the cannula 222. FIG. 8B shows the specimen retrieval system 208 in a fully squeezed position. When the actuation lever 214 is fully squeezed, a spring 268 having a spring loop 266 held captive in the housing 210 on one end and a spring hook 270 attached to a spring retainer 272 on the actuation lever 214 is in a tensioned state. Upon release of the actuation lever 214 by the operator, the actuation lever 214 is returned to the released position shown in FIG. 8A. While a spring biasing mechanism is used in this instance, other means of tensioning or biasing the actuation lever 214 in a manner that returns the actuation lever 214 to a released position after the operator lets go or releases the lever may be utilized. In addition, upon release of the actuation lever 214, the tenaculum actuator 260 returns to the distal direction along with the actuation lever 214. Due to the rounded and asymmetrical nature of the gears on the tenaculum shaft 226, the tenaculum actuator tab 258 slides over the gears and returns to its released position without moving the geared tenaculum shaft 226 back in the distal direction. The enclosed geared tenaculum 224, held in place by the retainer ring 230 and retention spring 256 will not move forward, thereby retaining any grasped tissue in a proximal direction 282 until the tissue is removed from the patient.

Figure 8C:
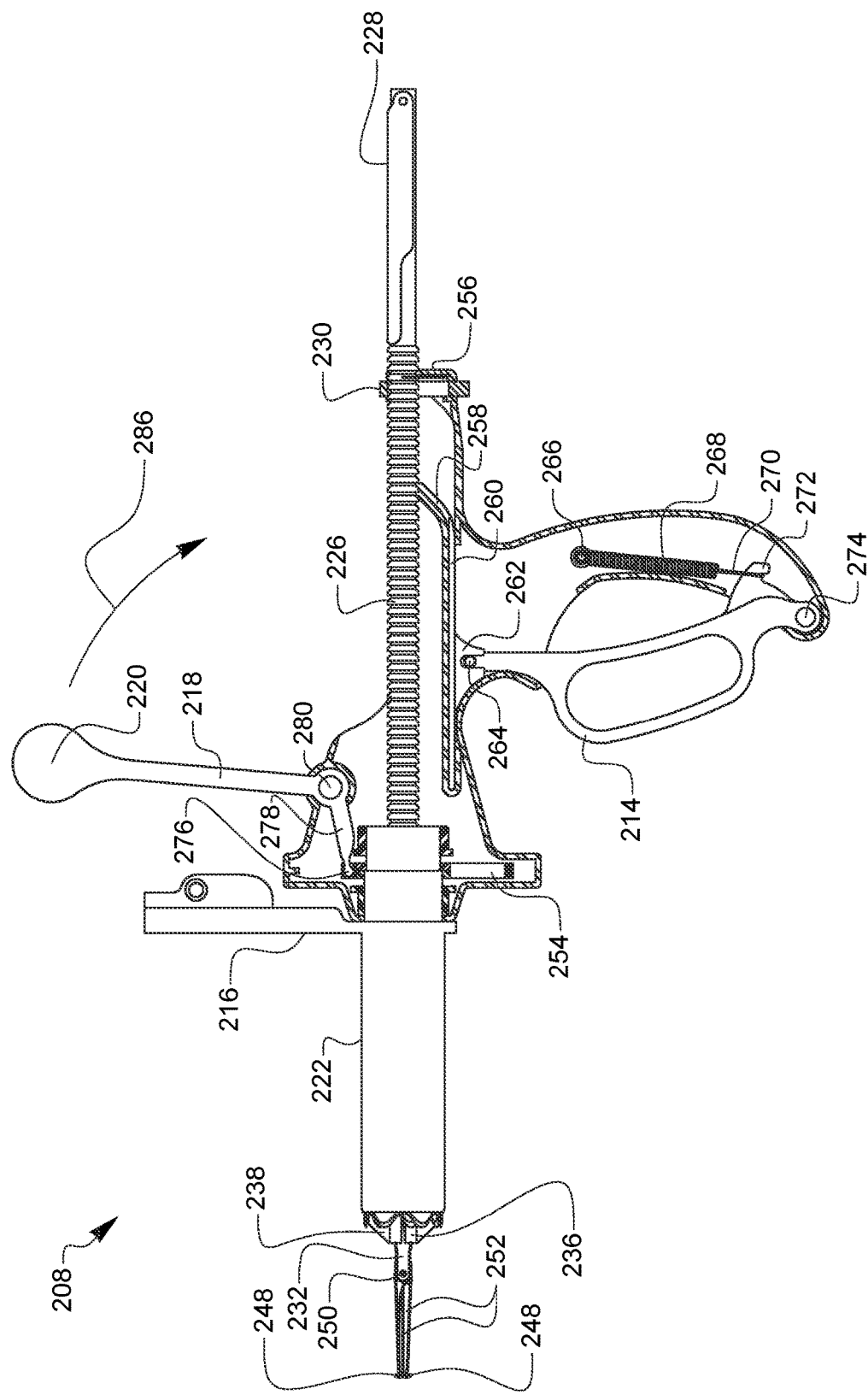
Figure 8D:
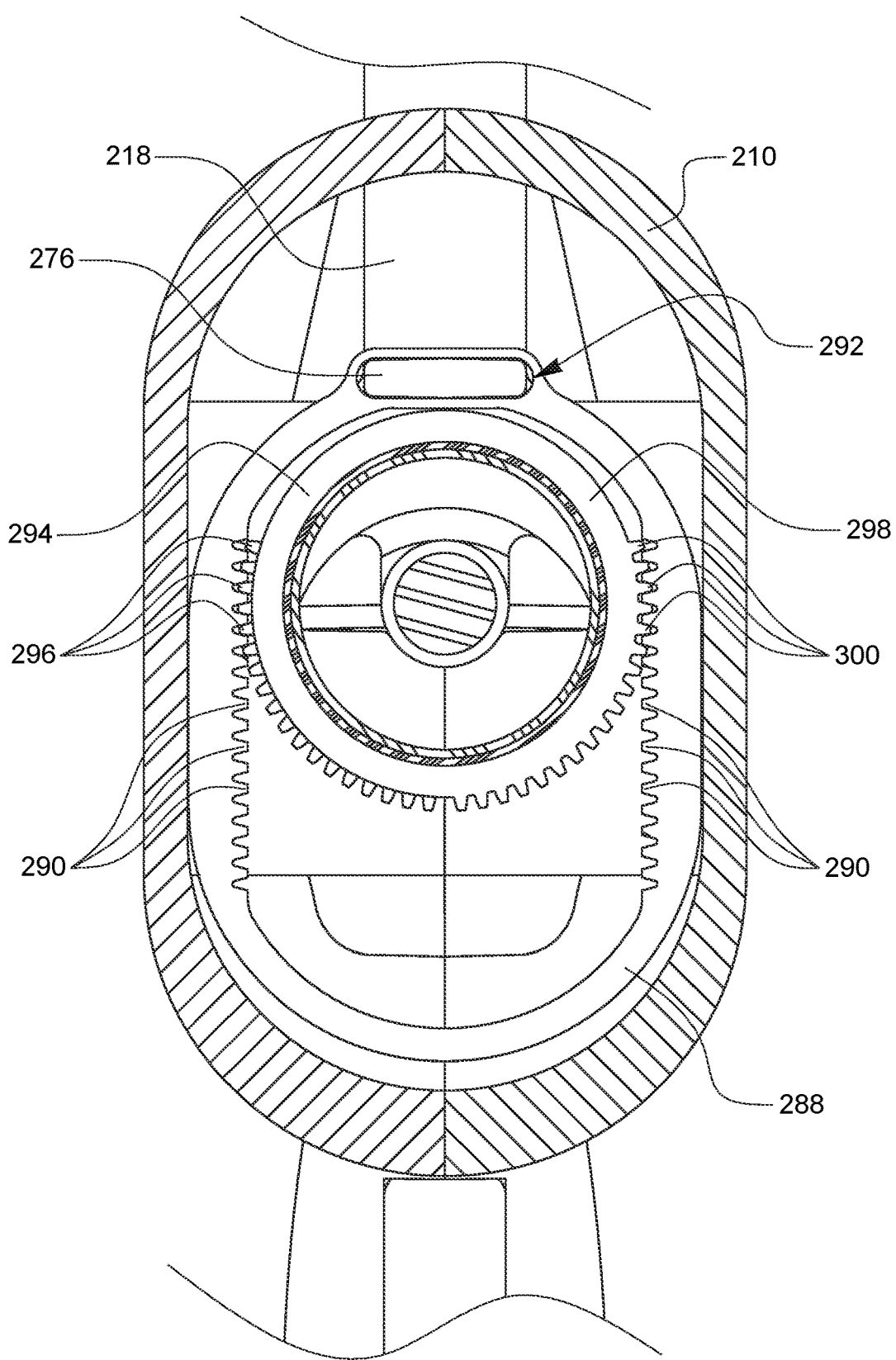

FIG. 8C is a partial cross-sectional side view of the surgical specimen retrieval system 208 of FIG. 7A, illustrating the operational motion of the throttle 218 and inner and outer tubes. While holding the handle 212 of the specimen retrieval system 208, an operator grasps the throttle knob 220 connected to the throttle 218 and pulls the throttle 218 in a downward and proximal direction 286. This motion lifts the throttle tab 276 upwards. Since the throttle tab 276 is inserted in a rack recess 292 on the rack 288 of the rack assembly (not shown in this view, but discussed in regard to FIGS. 8D and 8F), the rack assembly is also lifted. The rack teeth 290 on the rack 288 engage several inner tube gear teeth 296 on an inner tube gear 294 and several outer tube gear teeth 300 on an outer tube gear 298, as shown in FIG. 8D. FIG. 8D is a front cross-sectional view of the internal assembly shown from the distal end of the surgical specimen retrieval system of FIG. 7A, illustrating the position of the throttle 218 and inner and outer tubes of FIG. 8C in a released position. The location and configuration of the throttle tab 276 within the rack recess 292 of the rack 288, rack teeth 290, inner tube gear 294, inner tube gear teeth 296, outer tube gear 298, and outer tube gear teeth 300 inside the housing 210 are shown in a released position.

Figure 8E:
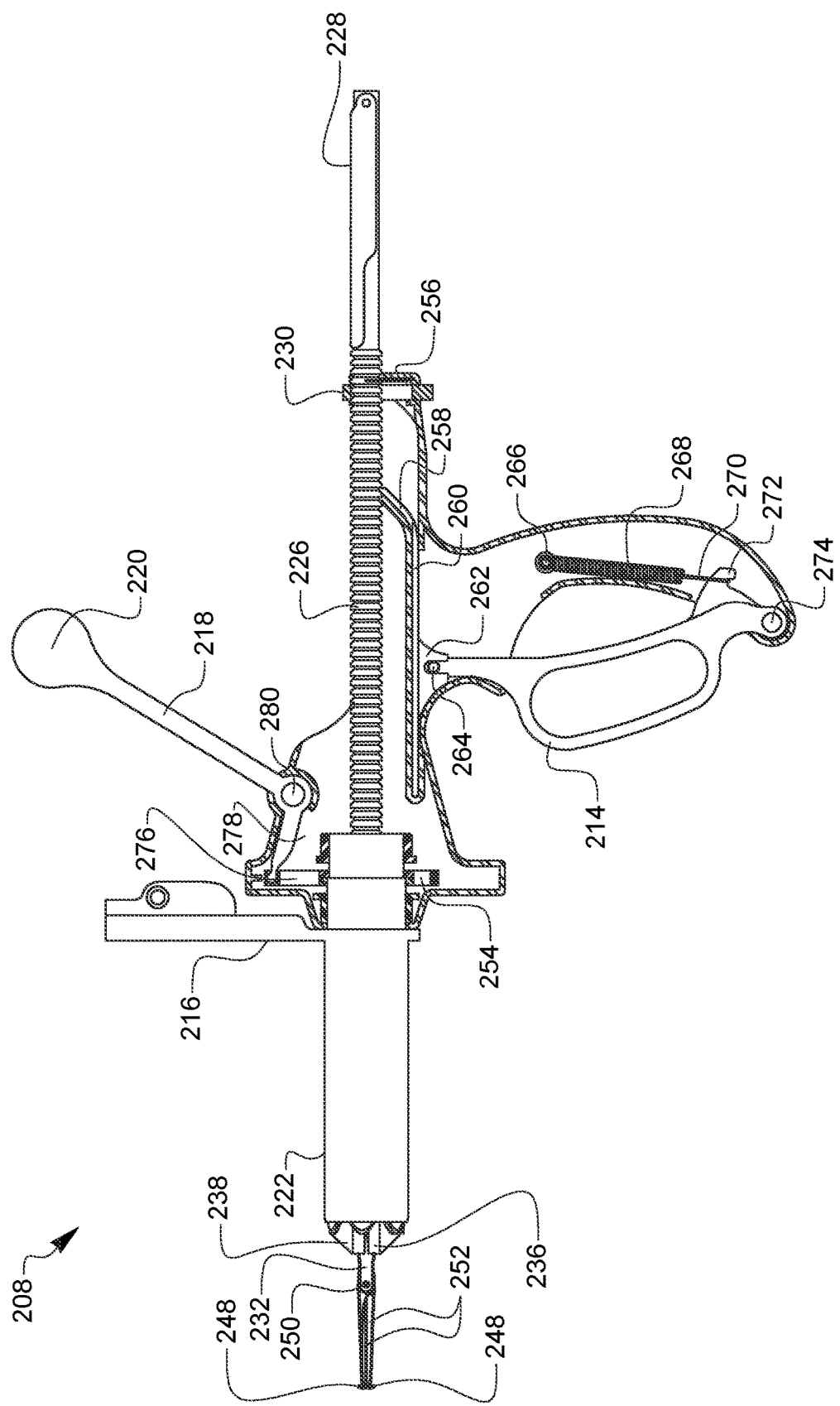
Figure 8F:
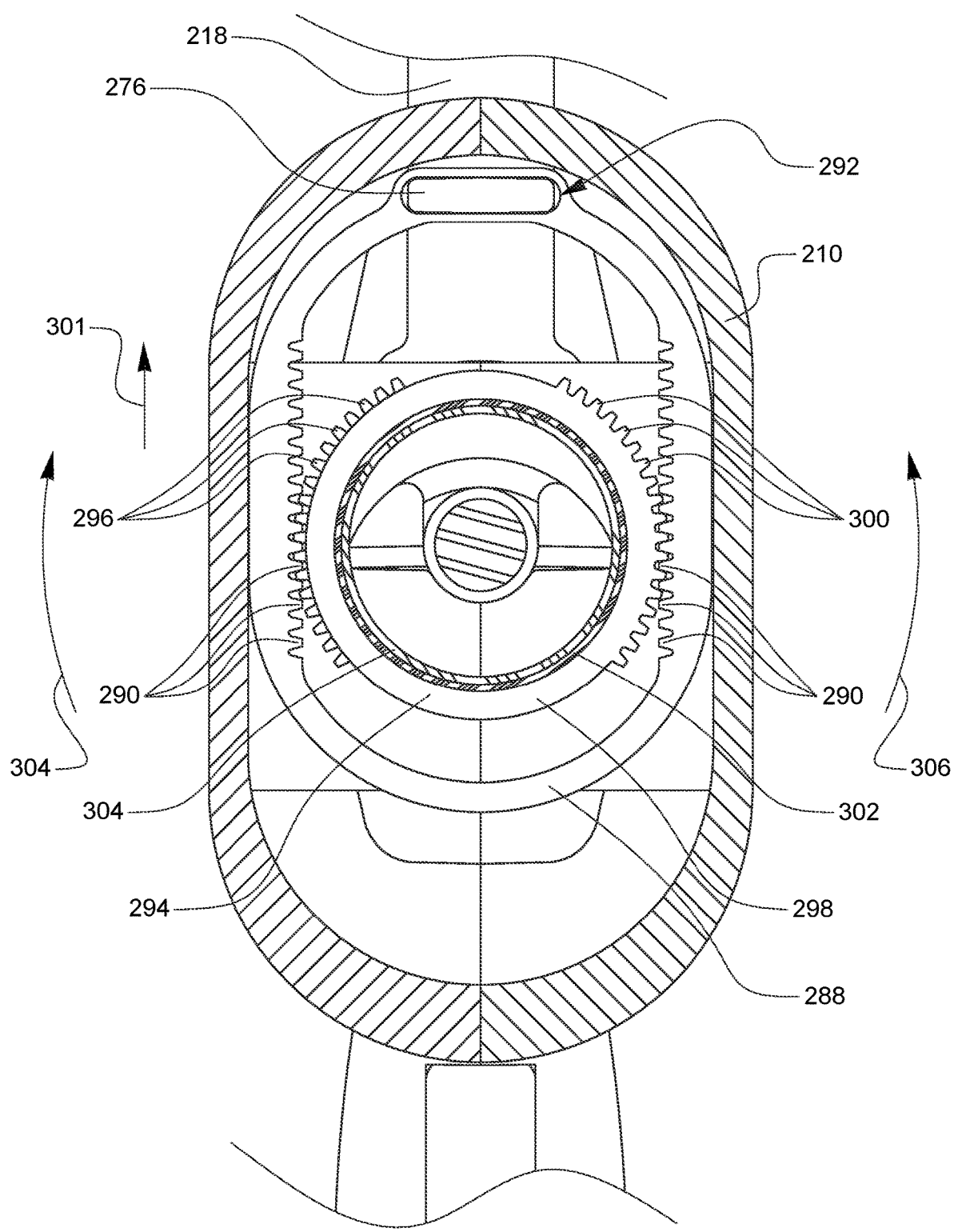

FIG. 8E is a partial cross-sectional side view of the surgical specimen retrieval system 208 of FIG. 7A, illustrating the operational motion of the throttle 218 and inner and outer tubes. The specimen retrieval system 208 is shown with the throttle 218 pulled back in a proximal direction 282 as indicated previously with the throttle 218 rotated around the throttle pivot 280 and the throttle lever 278 and throttle tab 276 lifted. In this engaged or actuated position of the throttle 218, the rack assembly has also been lifted. The effect of lifting the rack assembly by the throttle 218 is shown in FIG. 8F. FIG. 8F is a front cross-sectional view of the internal assembly shown from the distal end of the surgical specimen retrieval system 208 of FIG. 7A, illustrating the operational motion of the throttle 218 and inner and outer tubes of FIG. 8E. The location and configuration of the throttle tab 276 within the rack recess 292 of the rack 288, rack teeth 290, inner tube gear 294, inner tube gear teeth 296, outer tube gear 298, and outer tube gear teeth 300 inside the housing 210 are shown in an engaged or actuated position. As the throttle 218 is pulled back as indicated previously, and the throttle tab 276, engaged in the rack recess 288, lifts the rack assembly, the rack teeth 290 on either side of the rack 288 engage the inner tube gear teeth 296 on the inner tube gear 294 and the outer tube gear teeth 300 on the outer tube gear 298. This occurs simultaneously or nearly at the same time, resulting in a counter-rotation of the inner tube and the outer tube. The inner tube rotates in a clockwise direction as indicated by the inner tube direction 308, while the outer tube rotates in a counter clockwise direction as indicated by an outer tube direction 306. This counter-rotation results in cutting or coring of tissue in contact with the sharpened ends of the inner tube and outer tube. Upon returning the throttle 218 by lowering the throttle 218 to the position shown in FIGS. 8C and 8D, the rack assembly is lowered back to the position shown in 22B and the blades return to their released position. This released position is illustrated in FIG. 9A. In some embodiments, the blades may only counter-rotate upon moving the throttle upwards, and not counter-rotate upon return, or vice-versa.

Figure 9B:
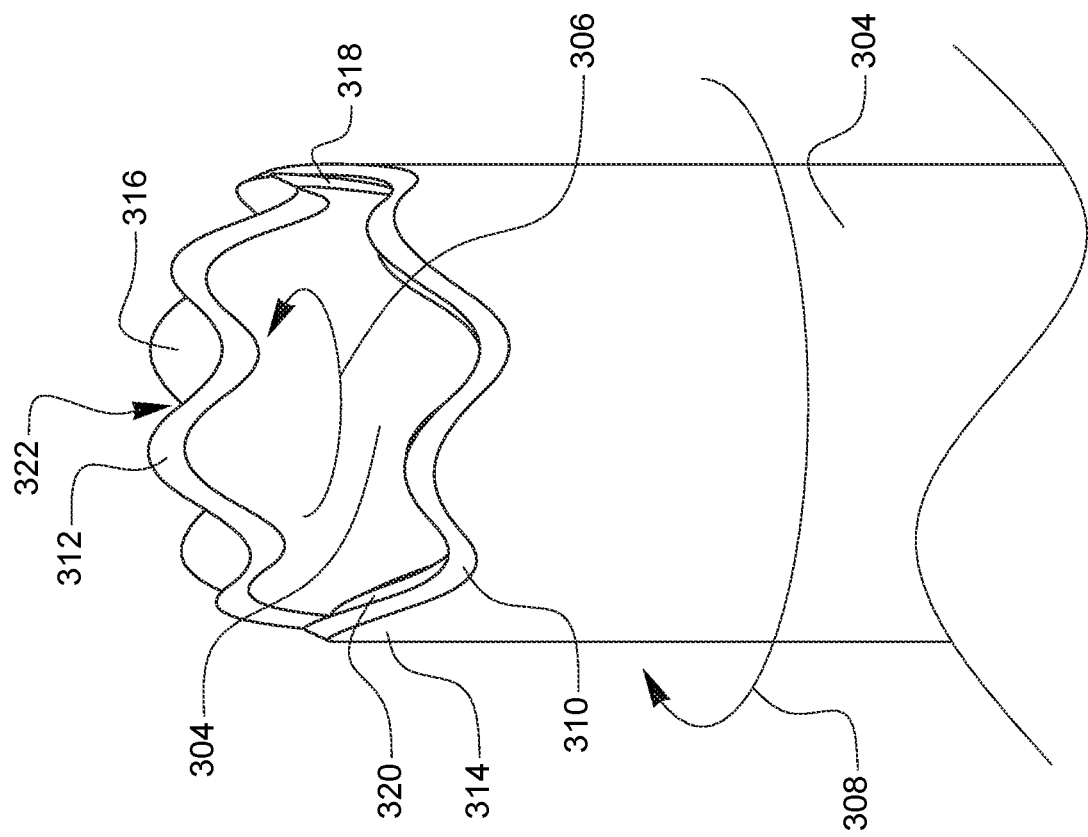
FIGS. 9A and 9B are enlarged perspective views of the end of the surgical specimen retrieval system of FIG. 7A, illustrating a blade tooth configuration in a released and an engaged position, respectively.
Figure 9A:
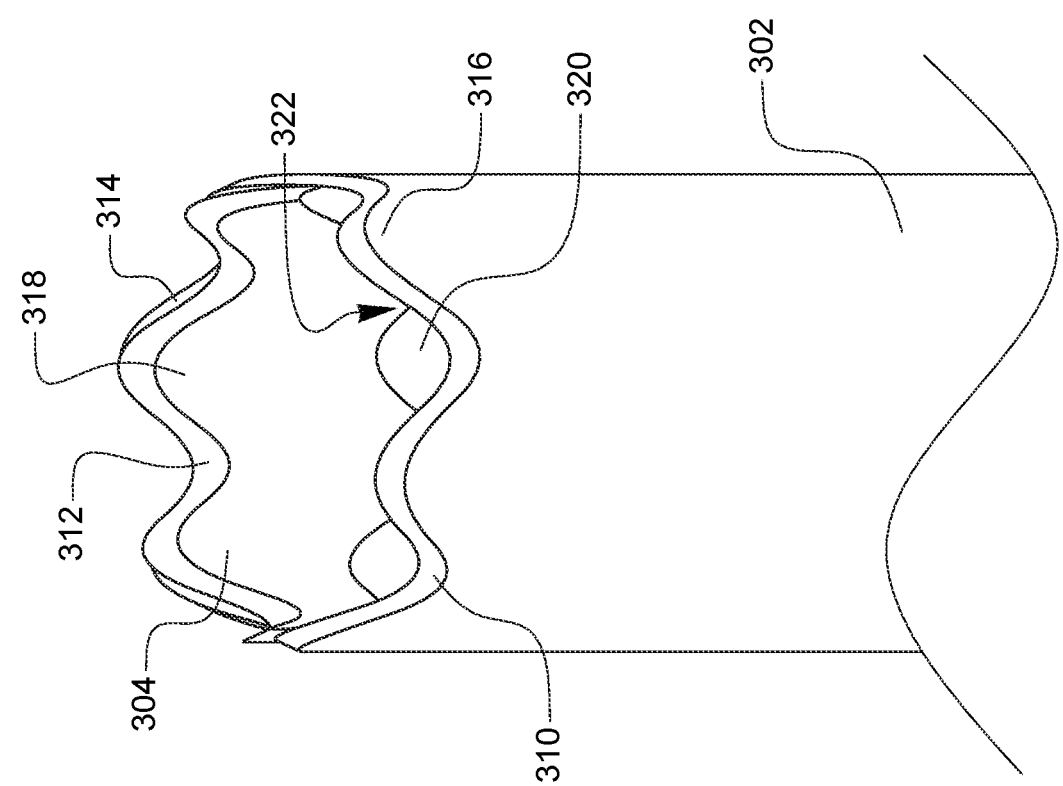

FIGS. 9A and 9B are enlarged perspective views of the end of the surgical specimen retrieval system of FIG. 7A, illustrating a blade tooth configuration in a released and an engaged position, respectively. FIGS. 9A and 9B illustrate one embodiment of the cutting action of the inner blade tube 304 and outer blade tube 302 during the counter rotation described in regard to FIGS. 8E and 8F. The sharpened end of both the inner tube 304 and outer tube 302 are shown. Also illustrated are the relative positions of several indicated inner blade teeth and outer blade teeth before, FIG. 9A, released position, and after, FIG. 9B, engaged position, one rotation step corresponding to one engagement of the throttle as described previously. The embodiment of the blade ends shown in FIGS. 9A and 9B has seven teeth on the inner tube 304 and six teeth on the outer tube 302. In FIG. 9A, the first inner blade tooth 318 and first outer blade tooth 314 as indicated are aligned while the second inner blade tooth 320 and second outer blade tooth 316 are not aligned or overlapped. In FIG. 9B, the first inner blade tooth 318 and first outer blade tooth 314 as indicated are now in different positions relative to the second inner blade tooth 320 and second outer blade tooth 316 as compared to FIG. 9A. It is believed that this arrangement in terms of number of inner blade teeth and outer blade teeth and the respective alignment therebetween results in improved cutting or coring performance, as there is always a valley between an inner blade tooth 318, 320 and an outer blade tooth 316, 318. This valley may be an optimized location of cutting between the inner blade tube 304 and outer blade tube 302, providing reduced cutting force translation to the operator. This improved cutting force may provide additional cutting or coring performance and possibly patient safety due to the operator not being required to provide an excessive level of force on the throttle of the specimen retrieval system to accomplish a cutting operation. While this is one embodiment and arrangement of the inner and outer teeth, other embodiments may be used, with varying numbers and alignments of inner blade teeth and outer blade teeth. For example, any number of inner blade teeth and outer blade teeth may be used, as well as configurations where the inner blade teeth and outer blade teeth are of the same number, different number, same alignment, different alignment, or any combination thereof FIGS. 10A and 10B are side-views of the specimen retrieval tenaculum of FIG. 7C in an open and closed position, respectively. The specimen retrieval tenaculum 224 has a tenaculum lever 228 at the proximal end 224P of the specimen retrieval tenaculum 224 attached to the tenaculum shaft 232 at a lever pivot point 324. The specimen retrieval tenaculum 224 also has a geared tenaculum shaft 226 composed of several asymmetrical tenaculum shaft gears 326. The asymmetrical gears 326 are characterized by a flat edge on the distal side and a rounded edge on the proximal side, which allow the unidirectional operation of the advancement of the specimen retrieval tenaculum 224 by the tenaculum actuation tab described earlier in regard to FIGS. 8A and 8B. The grasper arms 252 on the distal end 224D of the specimen retrieval tenaculum 224 are pivotably coupled to the tenaculum shaft 232 by a tenaculum pivot point 250 and the grasper arms 252 are closed by moving the tenaculum lever 228 in a direction 328 towards the tenaculum shaft 232. The mechanism inside the tenaculum lever may include Bellville washers or spring disc washers as internal components to facilitate and enable latching, although other means of closure may be utilized. The specimen retrieval tenaculum 224 also has a center guide 236 with several center guide fins 238 oriented around the center guide 236. These center guide fins 238 are configured to orient the specimen retrieval tenaculum 224 in a central location inside the inner tube during use of the specimen retrieval system 208. A ratchet or other means of indexing and moving the tenaculum in a proximal direction during operation of the specimen retrieval system may also be used.

Figure 11H:
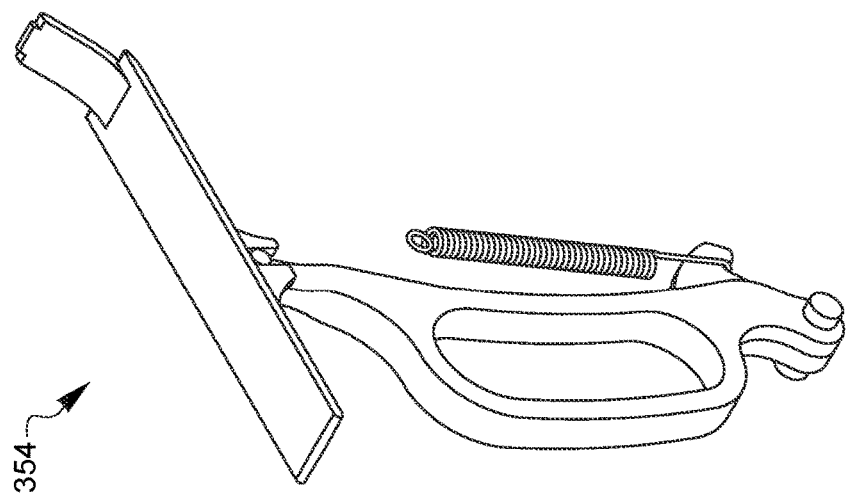

FIG. 11A-11H, and 11J-11L are a series of exploded views of the assembly of the surgical specimen retrieval system of FIG. 7A. It should be noted that FIG. 11I was not used in order to limit confusion with the number 111. FIG. 11A is an exploded view of the outer tube assembly of the surgical specimen retrieval system of FIG. 7A. FIG. 11B is a perspective view of the outer tube resulting from the assembly steps of FIG. 11A. The outer tube 302 is a hollow cylindrical tube with a sharpened end 310 at a distal end 302D of the outer tube. The outer tube 302 has a hollow center and is configured to receive several components on its outer surface. An outer tube bushing 336 and an outer tube gear 298 are assembled along a longitudinal axis 332 onto the proximal end 302P of the outer tube 302 and fixedly attached to the outer surface of the outer tube 302. The outer tube 302 is inserted into the centers of the outer tube bushing 336 and the outer tube gear 298. The outer tube gear 298 has several teeth 300 around a portion of its outer circumference. The outer tube 302 is made from stainless steel, and could alternatively be composed of any suitable metal or resilient plastic composite or other material suitable for surgical devices. The outer tube 302 may also have one or more scallops or teeth or other cutting elements at the end of the outer tube. The outer tube bushing 336 and outer tube gear 298 are made from a resilient plastic composite and fixedly attached to the outer tube 302 using epoxy, but any alternate appropriate adhesive could be used. FIG. 11B is a perspective view of the outer tube assembly 330 of the surgical specimen retrieval system assembled in FIG. 11A. The resulting subassembly 330 could alternatively be molded or fabricated as a single component using a suitable plastic composite or other material suitable for surgical devices.

FIG. 11C is an exploded view of the inner tube assembly of the surgical specimen retrieval system of FIG. 7A. The inner tube 304 is a hollow cylindrical tube with a sharpened end 312 at a distal end 304D of the inner tube 304. The inner tube 304 has a hollow center and is configured to receive several components on its outer surface. An inner tube gear 294 is assembled along a longitudinal axis 340 onto the proximal end 304P of the inner tube 304 and fixedly attached to the outer surface of the inner tube 304. The inner tube gear 294 has several teeth 296 around its outer circumference. The inner tube 304 is made from stainless steel and could alternatively be composed of any suitable metal or resilient plastic composite or other material suitable for surgical devices. The inner tube 304 may also have one or more scallops or teeth or other cutting elements at the end of the inner tube 304. The inner tube gear 294 is made from a resilient plastic composite and fixedly attached to the inner tube 304 using epoxy, but any alternate appropriate adhesive could be used. FIG. 11D is a perspective view of the inner tube assembly 342 resulting from the assembly steps of FIG. 11C. The resulting subassembly 342 could alternatively be molded or fabricated as a single component using a suitable plastic composite or other material suitable for surgical devices.

FIG. 11E is an exploded view of the assembly of the tube assembly of the surgical specimen retrieval system of FIG. 7A. The inner tube assembly 342 is inserted into the center of outer tube 302 starting at the proximal end 302P of the outer tube 302 in the outer tube subassembly 330 along a longitudinal axis 350, then the two tube subassemblies 330, 342 are placed within an opening in the rack along a longitudinal axis 348 into the rack 288. It should be noted that inner tube assembly 342 and outer tube assembly 330 are freely rotatable with respect to one another. FIG. 11F is a perspective view of the tube assembly 346 resulting from the assembly steps of FIG. 11E. The rack and tube assembly 346 is shown assembled, with the rack teeth 290 on one side of the rack 288 aligned to inner tube gear 294 and the rack teeth 290 on the other side of the rack 288 aligned to the outer tube gear 298. It should also be noted that the rack 288 is configured to move in either direction vertically in order to counter-rotate the inner tube assembly 342 relative to the outer tube subassembly 330. This has been described in greater detail with regard to FIGS. 8C-8F. Since the inner tube sharpened end 312 is adjacent to the outer tube sharpened end 310, if the two hollow tubes 302, 304 are counter-rotated, the sharpened ends 310, 312 are configured to act as circular scissors and cut through soft tissue. While the assembly shown in FIG. 11F has two sharpened ends 310, 312 it may be desirable for the outer tube 302 to have one or more shielding elements configured to coincide with a sharpened end or cutting elements on the inner tube 304. The purpose of such shielding elements would be to protect areas of the body or tissue within the body outside the scope of a given surgical procedure from trauma or cutting while a surgical device of the present disclosure is introduced into a body or a body cavity.

Figure 11G:
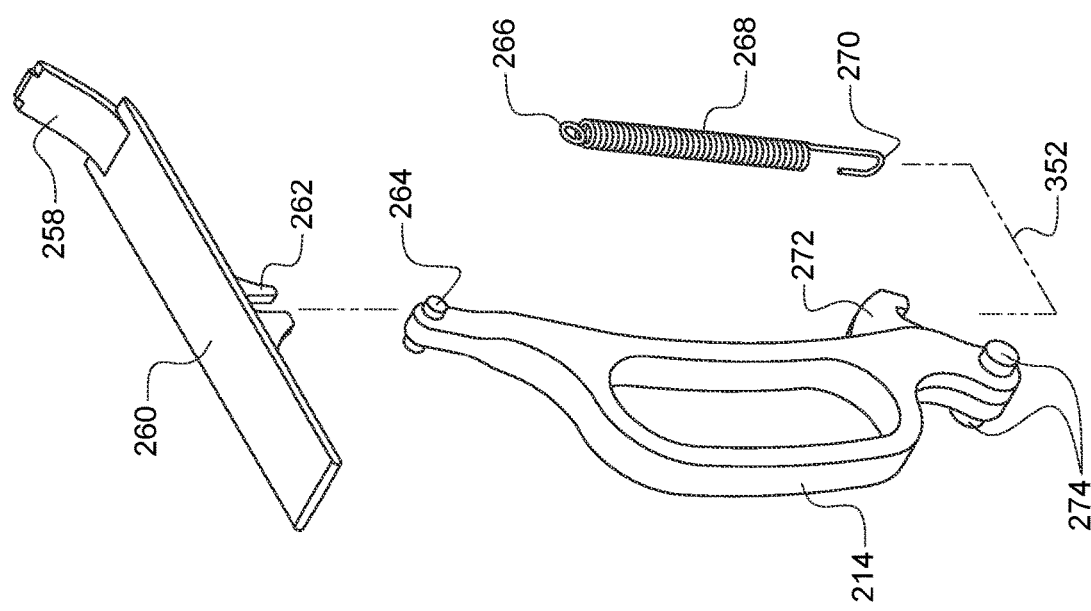

FIG. 11G is an exploded view of the assembly of the tenaculum actuator assembly of the surgical specimen retrieval system of FIG. 7A. The actuation lever 214 defines a lever pivot 274, a spring retainer 272, and a tenaculum actuator pivot 264. The lever pivot 274 is configured to be held captive in the housing 210 of the surgical specimen retrieval system 208 and allow the actuation lever 214 to pivot upon actuation or squeezing by the operator. The spring retainer 272 is configured to hold a spring 268 by a spring hook 270 for the purpose of returning the actuation lever 214 to its released position after being squeezed. The tenaculum actuator pivot 264 is configured to be inserted into an actuator coupler 262 defined by the tenaculum actuator 260. The tenaculum actuator pivot 264 will actuate the tenaculum actuator 260 back and forth as the actuation lever 214 is moved. The tenaculum actuator 260 further defines a tenaculum actuator tab 258 which is configured to engage with the gears on the geared tenaculum shaft as described previously. FIG. 11H is a perspective view of the tenaculum actuator assembly 354 resulting from the assembly steps of FIG. 11G.

Figure 11J:
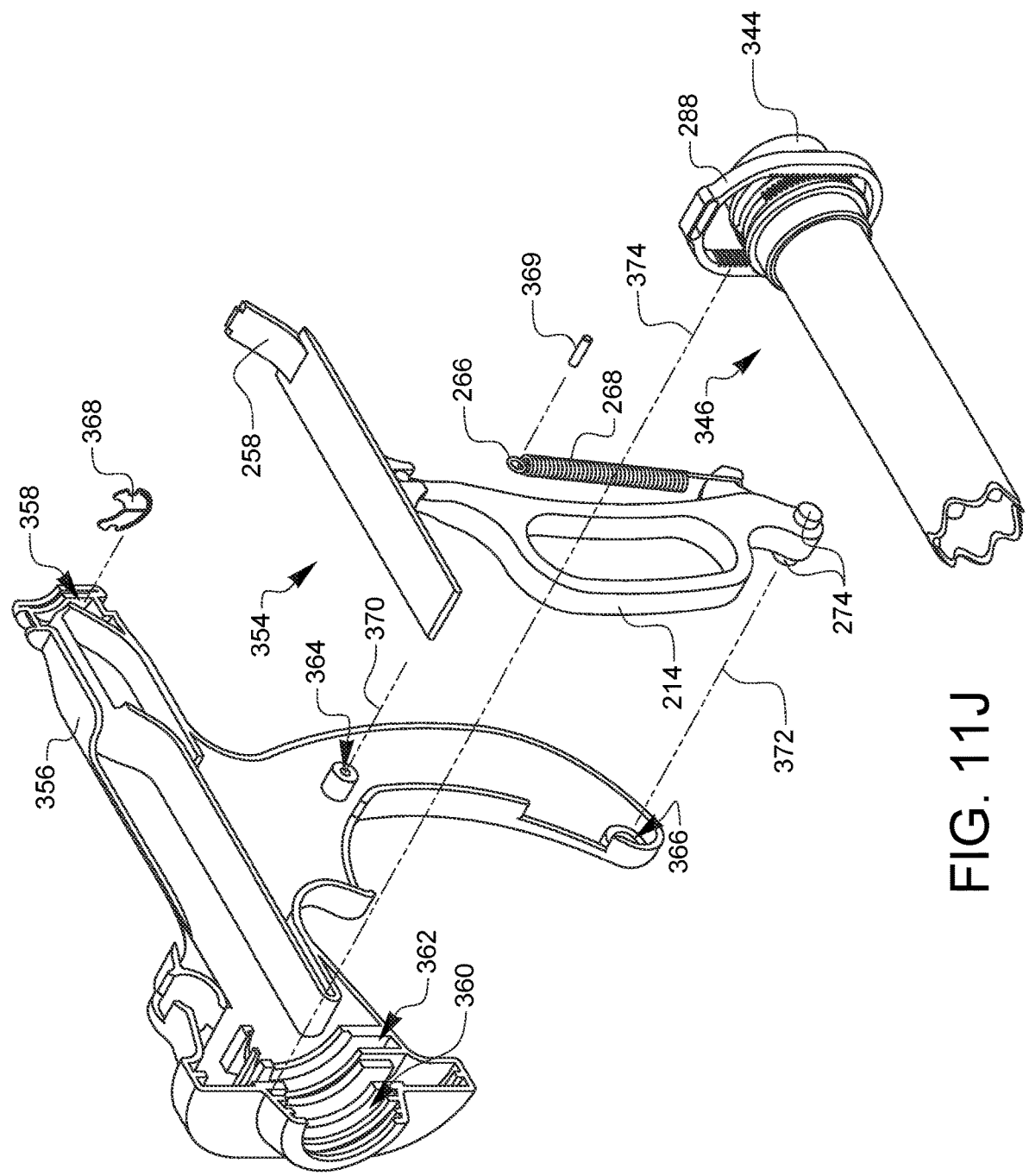

FIG. 11J is an exploded view of an assembly step of the surgical specimen retrieval system of FIG. 7A. A first housing half 356 defining several recesses including a bushing recess 360, a rack recess 362, a pin recess 364, a lever pivot recess 366, and a retention spring recess 358 forms half of the housing of the surgical specimen retrieval system 208. A retention spring 368 is inserted into the retention spring recess 358 of the first housing half 356. The retention spring 368 is configured to work in combination with the retainer ring to hold the geared tenaculum shaft in place when the specimen retrieval tenaculum 224 is loaded into the surgical specimen retrieval system 208. The retention spring 268 is also configured to prevent the geared tenaculum from moving in a distal direction once it is actuated in a proximal direction as described in regard to FIGS. 8A and 8B. The tenaculum actuator assembly 354 of FIG. 11H is loaded into the first housing half 356. The tenaculum actuator assembly 354 is aligned within the first housing half 356 by inserting the lever pivot 274 into the lever pivot recess 366 along a longitudinal axis 372 and by inserting a pin 369 along a longitudinal axis 370 and through the spring loop 266 of the spring 268 into the pin recess 364 on the first housing half 356. The tenaculum actuator assembly 354 is configured such that the actuator tab 258 protrudes out of the housing to sufficiently engage with the geared tenaculum shaft when loaded into the surgical specimen retrieval system 208. Finally, the tube assembly 346 of FIG. 11F is inserted into the first housing half 356 by aligning the inner tube bushing 344, the rack 288, and the outer tube bushing 336 of the tube assembly 346 into the bushing recess 360 and the rack recess 362 along a longitudinal axis 374.

Figure 11K:
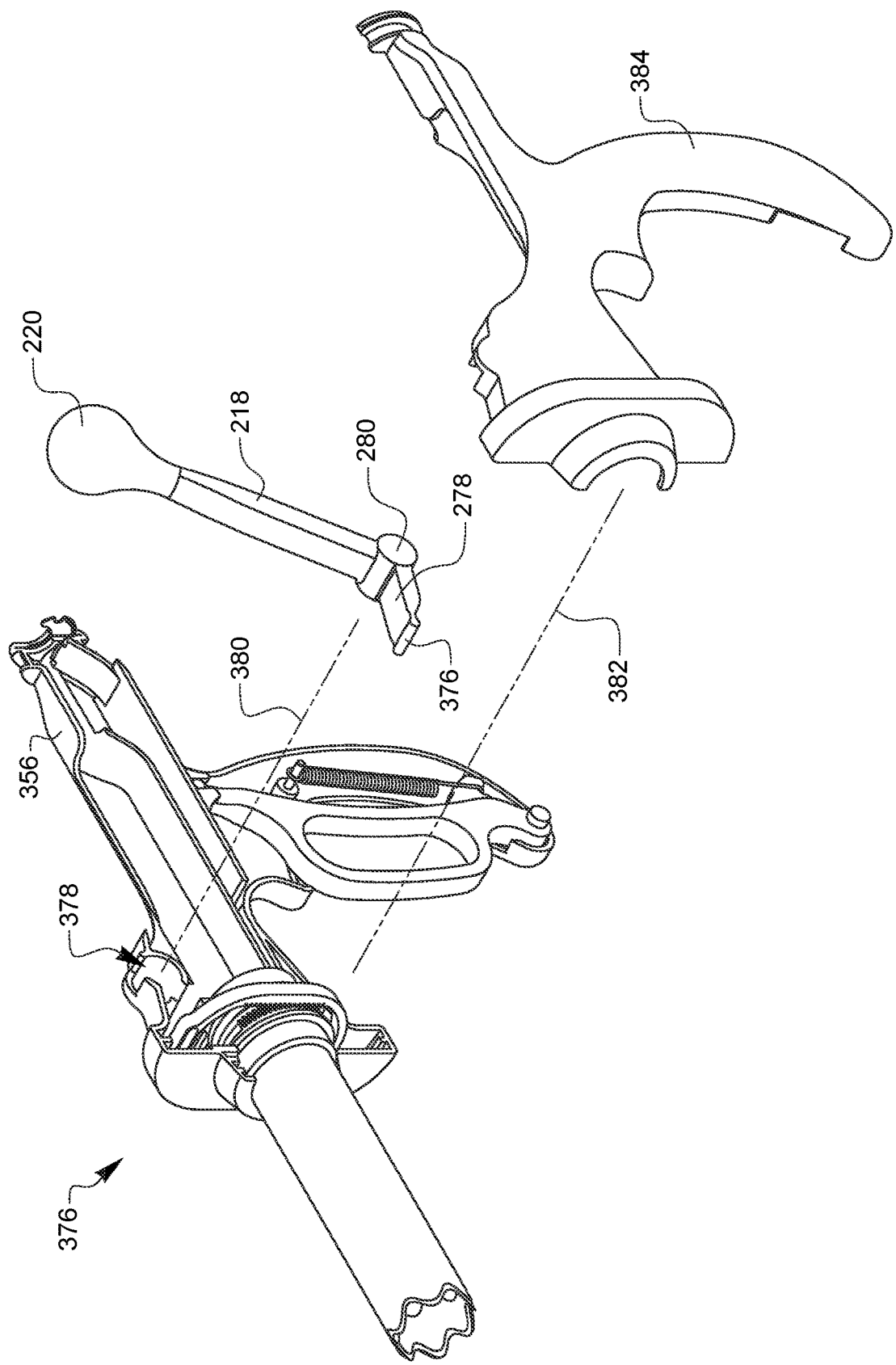

FIG. 11K is an exploded view of an assembly step of the surgical specimen retrieval system of FIG. 7A. The resulting specimen retrieval system subassembly 376 of FIG. 11J has the throttle 218 inserted along an axis 380 and into a throttle pivot recess 378 defined by the first housing half 356. A second housing half 384 defining several recesses including a bushing recess, a rack recess, a pin recess, a lever pivot recess, and a retention spring recess, not shown in this view, forms half of the housing of the surgical specimen retrieval system 208. These recesses correspond to those defined by the first housing half 356. The second housing half 384 is mated with the first housing half 356 along an axis 382, completing this step of the assembly of the specimen retrieval system 208. The first housing half 356 and the second housing half 384 are fixedly attached by adhesion, welding or some other suitable means known to those skilled in the art.

Figure 11L:
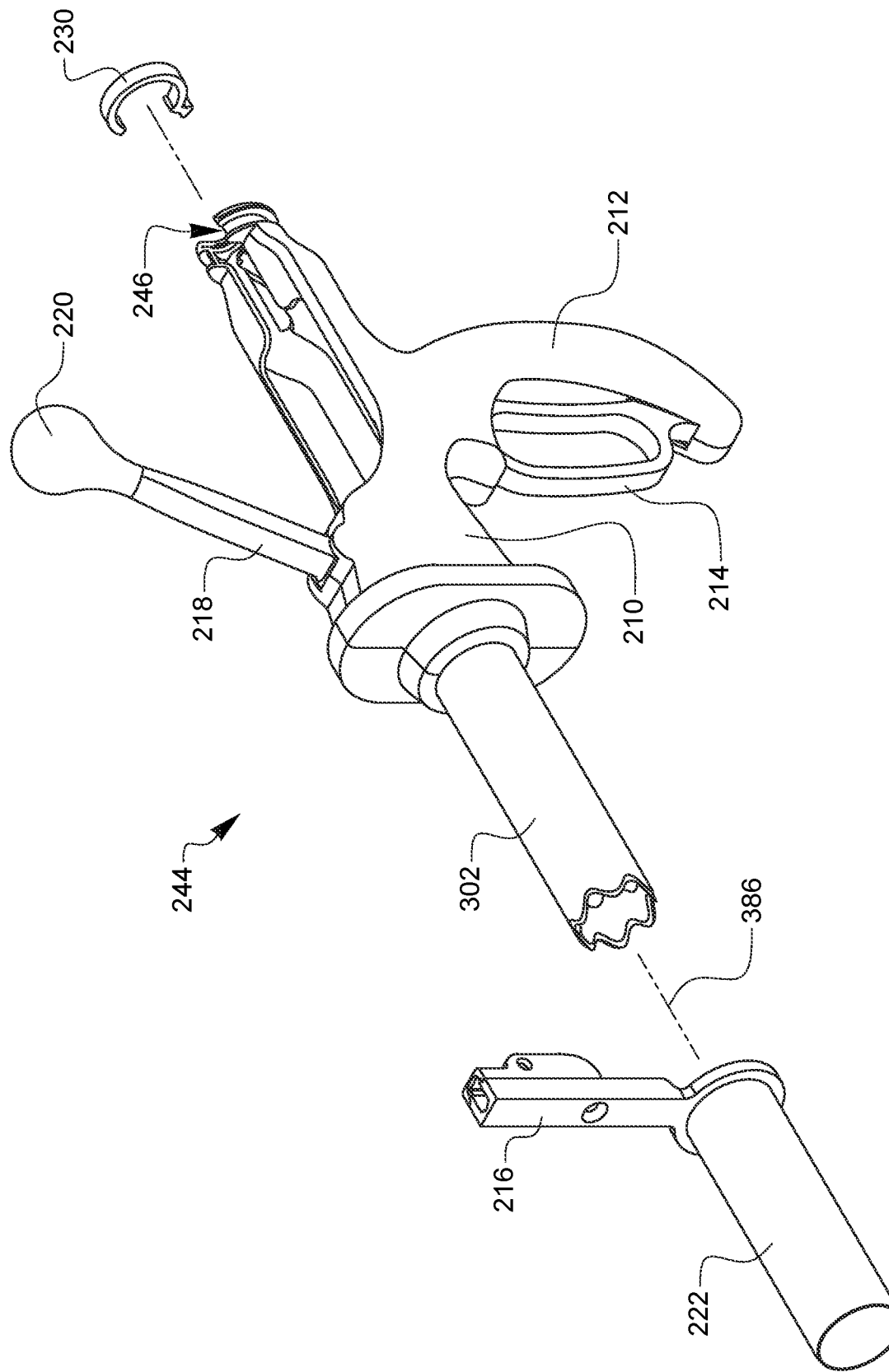

FIG. 11L is an exploded view of an assembly step of the surgical specimen retrieval system of FIG. 7A. The specimen coring device 244 of FIG. 11K has a retainer ring 230 inserted over a retainer ring recess 246 on the housing 210 of the specimen coring device 244. The cannula 222, with cannula adapter 216 attached is then placed along an axis 386 over the outer tube 302 of the specimen coring device 244.

Figure 12:
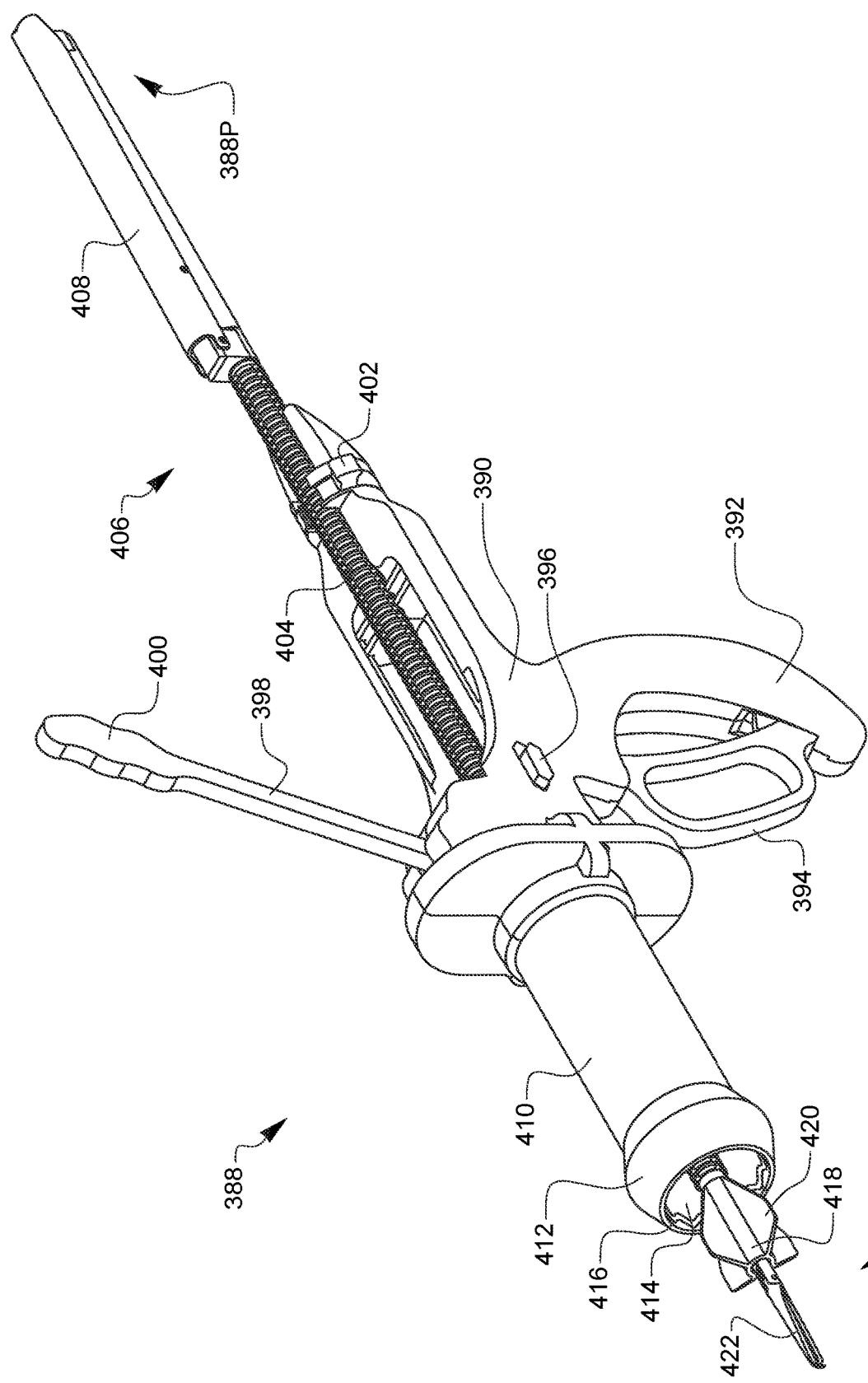
FIG. 12 is a top-left-front perspective view of another embodiment of a surgical specimen retrieval system.

FIG. 12 is a top-left-front perspective view of another embodiment of a surgical specimen retrieval system. The specimen retrieval system 388 has an outer housing 390 which defines a handle 392 for manual holding of the instrument during operation. The housing 390 holds a throttle 398 or throttle actuator 398 having a throttle knob 400, a tube assembly not visible in this view, an actuation lever 394 connected to and configured to counter-rotate the tube assembly, and a geared tenaculum 406. The geared tenaculum 406 has a geared tenaculum shaft 404 connected to a tenaculum lever 408 towards a proximal end 388P of the specimen retrieval system 388, and a center guide 418 and pair of grasper arms 422 towards a distal end 388D. The center guide 418 further defines several center guide fins 420 configured to maintain the grasper arms 422 and tenaculum shaft 404 in a centered position within the tube assembly of the specimen retrieval system 388. A retainer ring 402 towards the proximal end 388P of the specimen retrieval system 388 holds the geared tenaculum 404 in place within the housing 390 of the specimen retrieval system 388. A guard cannula 410 also defining a guard cannula tip 412 is shown covering an inner tube 414 and an outer tube 416 of the specimen retrieval system 388. The guard cannula 410 is configured to cover the tube assembly to provide an added safety measure from unintentional trauma to a patient while in operation. A switch 396 is coupled to the guard cannula 410 and is configured to slide the guard cannula 410 over the cutting elements or blades of the inner tube 414 and the outer tube 416. The guard cannula 410 is also configured to attach or mount the specimen retrieval system 388 to a surgical equipment holder or other surgical mounting device. This can fix the position of the specimen retrieval system 388 in place during operation or during a minimally invasive surgical procedure. Alternate embodiments may include other actuators or other components configured to slide the guard cannula distally and proximally over the cutting elements at the ends of the inner tube 414 and the outer tube 416. A knob, lever, slider element, selector switch, or other actuation elements known to those skilled in the art may be used.

Various advantages of a uterine coring device, a specimen retrieval system, and related methods have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A specimen retrieval system, comprising:
    a first tube extending along a first tube axis from a proximal end to a distal end, wherein one or more cutting elements are disposed at the distal end of the first tube;
    a second tube extending along a second tube axis from a proximal end to a distal end, wherein one or more cutting elements are disposed at the distal end of the second tube;
    a first actuator coupled to each of the first tube and the second tube such that the first actuator rotates the first tube about the first tube axis and the second tube about the second tube axis;
    a tenaculum assembly comprising a shaft extending along a shaft axis from a proximal end to a distal end, wherein at least a portion of the shaft is disposed within an interior portion of the first tube; and
    a second actuator coupled to the shaft of the tenaculum assembly to linearly displace the tenaculum assembly along the shaft axis,
    the tenaculum assembly further comprising a plurality of gears disposed around a circumference of the shaft, wherein a portion of the second actuator contacts a portion of at least one of the plurality of gears to linearly displace the tenaculum assembly along the shaft axis.

2. The specimen retrieval system of claim 1, the second actuator further comprising:
    an actuation lever pivotably coupled to a portion of a housing, wherein the tenaculum assembly linearly displaces along the shaft axis relative to the housing, and wherein the actuation lever is configured to be displaced in a first direction; and
    a tenaculum actuator slide coupled to a portion of the actuation lever, the tenaculum actuator slide having an actuator tab, and an end portion of the actuator tab is configured to contact the portion of the at least one of the plurality of gears to linearly displace the tenaculum assembly along the shaft axis when the actuation lever is displaced in the first direction.

3. The specimen retrieval system of claim 2, wherein the tenaculum actuator slide is elongated and extends from a proximal end to a distal end, the actuator tab being disposed at or adjacent to the proximal end of the tenaculum actuator slide, wherein the tenaculum actuator slide is configured as a cantilevered spring that biases the end portion of the actuator tab into contact with the portion of the at least one of the plurality of gears.

4. The specimen retrieval system of claim 2, wherein the tenaculum actuator slide displaces linearly when the actuation lever is displaced in the first direction.

5. The specimen retrieval system of claim 2, wherein the actuation lever is configured to be pivotably displaced in a first direction by a user.

6. The specimen retrieval system of claim 2, wherein the at least one of the plurality of gears is asymmetrically shaped when viewed normal to the shaft axis.

7. The specimen retrieval system of claim 6, wherein the at least one of the plurality of gears has a flat edge on a distal side and a rounded edge on a proximal side.

8. The specimen retrieval system of claim 1, the tenaculum assembly further comprising a pair of grasper arms coupled to the distal end of the shaft, wherein at least one of the pair of grasper arms is pivotably displaceable between a first position and a second position.

9. The specimen retrieval system of claim 8, the tenaculum assembly further comprising a grasper actuator coupled to at least one of the pair of grasper arms such that the grasper actuator is configured to pivot the at least one of the pair of grasper arms from the first position to the second position.

10. The specimen retrieval system of claim 9, wherein the grasper actuator is a lever pivotably coupled to the shaft at a pivot point that is at or adjacent to the proximal end of the shaft, wherein pivoting the lever from a first position to a second position pivots the at least one of the pair of grasper arms from the first position to the second position.

11. The specimen retrieval system of claim 1, wherein the first tube has a first diameter and the second tube has a second diameter that is greater than the first diameter.

12. The specimen retrieval system of claim 1, wherein the first actuator rotates the first tube about the first tube axis in a first rotational direction and rotates the second tube about the second tube axis in a second rotational direction that is opposite to the first rotational direction.

13. The specimen retrieval system of claim 1, further comprising a housing, wherein the first tube is rotatably coupled to the housing and the second tube is rotatably coupled to the housing, and wherein the first actuator is coupled to the housing.

14. The specimen retrieval system of claim 13, wherein the first tube does not displace along the first tube axis relative to the housing and the second tube does not displace along the second tube axis relative to the housing.

15. The specimen retrieval system of claim 13, the first actuator further comprising a rack having (a) a first plurality of rack teeth configured to engage a corresponding plurality of first gear teeth disposed along a circumferential portion of the first tube to rotate the first tube about the first tube axis and (b) a second plurality of rack teeth configured to engage a corresponding plurality of second gear teeth disposed along a circumferential portion of the second tube to rotate the second tube about the second tube axis.

16. The specimen retrieval system of claim 15, wherein the first gear teeth are disposed at or adjacent to the proximal end of the first tube and the second gear teeth are disposed at or adjacent to the proximal end of the second tube.

17. The specimen retrieval system of claim 15, wherein the rack displaces linearly along a rack axis that is normal to each of the first tube axis and the second tube axis such that the linear displacement of the rack rotates the first tube about the first tube axis and the second tube about the second tube axis.

18. The specimen retrieval system of claim 17, the first actuator further comprising a throttle lever coupled to the housing and configured to be pivoted from a first portion to a second position, and wherein a portion of the throttle lever is coupled to the rack such that as the throttle lever is pivoted from the first portion to the second position, the rack is linearly displaced along the rack axis.

19. The specimen retrieval system of claim 1, wherein the first tube is coaxially aligned with the second tube, and wherein the distal end of the first tube is disposed at or adjacent to the distal end of the second tube.

20. A specimen retrieval system, comprising:
a first tube extending along a first tube axis from a proximal end to a distal end, wherein one or more cutting elements are disposed at the distal end of the first tube;
a second tube extending along a second tube axis from a proximal end to a distal end, wherein one or more cutting elements are disposed at the distal end of the second tube;
a first actuator coupled to each of the first tube and the second tube such that the first actuator rotates the first tube about the first tube axis and the second tube about the second tube axis, the first actuator comprising a rack having (a) a first plurality of rack teeth configured to engage a corresponding plurality of first gear teeth disposed along a circumferential portion of the first tube to rotate the first tube about the first tube axis and (b) a second plurality of rack teeth configured to engage a corresponding plurality of second gear teeth disposed along a circumferential portion of the second tube to rotate the second tube about the second tube axis;
a housing, wherein the first tube is rotatably coupled to the housing and the second tube is rotatably coupled to the housing, and wherein the first actuator is coupled to the housing;
a tenaculum assembly comprising a shaft extending along a shaft axis from a proximal end to a distal end, wherein at least a portion of the shaft is disposed within an interior portion of the first tube; and
a second actuator coupled to the shaft of the tenaculum assembly to linearly displace the tenaculum assembly along the shaft axis.

21. The specimen retrieval system of claim 20, wherein the first gear teeth are disposed at or adjacent to the proximal end of the first tube and the second gear teeth are disposed at or adjacent to the proximal end of the second tube, and wherein the rack displaces linearly along a rack axis that is normal to each of the first tube axis and the second tube axis such that the linear displacement of the rack rotates the first tube about the first tube axis and the second tube about the second tube axis.

22. The specimen retrieval system of claim 21, the first actuator further comprising a throttle lever coupled to the housing and configured to be pivoted from a first portion to a second position, and wherein a portion of the throttle lever is coupled to the rack such that as the throttle lever is pivoted from the first portion to the second position, the rack is linearly displaced along the rack axis.

* * * * *